United States Patent
Bash et al.

(10) Patent No.: US 11,464,845 B2
(45) Date of Patent: Oct. 11, 2022

(54) *NEISSERIA MENINGITIDIS* IMMUNOGENIC COMPOSITIONS

(71) Applicant: THE UNITED STATES OF AMERICA, as represented by the Secretary, Department of Health and Human Services, Silver Spring, MD (US)

(72) Inventors: Margaret Bash, Silver Spring, MD (US); Kathryn Matthias, Silver Spring, MD (US)

(73) Assignee: THE UNITED STATES OF AMERICA, as represented by the Secretary, Department of Health and Human Services, Silver Spring, MD (US)

( * ) Notice: Subject to any disclaimer, the term of this patent is extended or adjusted under 35 U.S.C. 154(b) by 0 days.

(21) Appl. No.: 16/632,278

(22) PCT Filed: Jul. 20, 2018

(86) PCT No.: PCT/US2018/043054
§ 371 (c)(1),
(2) Date: Jan. 17, 2020

(87) PCT Pub. No.: WO2019/018744
PCT Pub. Date: Jan. 24, 2019

(65) Prior Publication Data
US 2020/0360503 A1    Nov. 19, 2020

Related U.S. Application Data

(60) Provisional application No. 62/535,627, filed on Jul. 21, 2017.

(51) Int. Cl.
*A61K 39/095* (2006.01)
*C07K 14/22* (2006.01)
*C12N 1/20* (2006.01)

(52) U.S. Cl.
CPC ............ *A61K 39/095* (2013.01); *C07K 14/22* (2013.01); *C12N 1/20* (2013.01)

(58) Field of Classification Search
None
See application file for complete search history.

(56) References Cited

U.S. PATENT DOCUMENTS

2006/0216307 A1    9/2006   Berthet et al.
2018/0064801 A1*   3/2018   Pizza ...................... A61P 37/04

FOREIGN PATENT DOCUMENTS

WO   WO 2001/009350 A2   2/2001
WO   WO 2005/004908 A1   1/2005

OTHER PUBLICATIONS

Liu et al. Microbiology, 161: 1297-1312, 2015.*
Campbell AM. In: Monoclonal Antibody Technology. Elsevier Science Publishers, The Netherlands, Chapter 1, pp. 1-32, 1984.*
Harlow and Lane. In: Antibodies: A Laboratory Manual, Harlow E and Lane D, Cold Spring Harbor Press, New York, pp. 139-172, 1988.*
Tramont et al. J. Infect. Dis. 130: 240-247, 1974.*
Matthias et al. Mol. Microbiol. 105: 934-953, 1-34 to 34/34, Jul. 14, 2017.*
Wilson et al. J. Clin. Microbiol. 4: 214-215, 1976.*
STI Treatment Guidelines, CDC, pp. 1/3 to 3/3, 2021.*
Landy et al. Int. J. Infect. Dis. 14S: e239-e241, 2010.*
Russell et al. Front. Immunol. 10: 2417, Oct. 15, 2019, abstract.*
Edwards et al. Crit. Rev. Microbiol. 42: 928-941, published online Jan. 23, 2016.*
Jerse AE, WHO PD-VAC Meeting on Jun. 21-22, 2017, pp. 1-37.*
Zollinger et al. In: Proceedings of the 9th International Pathogenic Neisseria Conference, (eds) Evans et al., Winchester, England, Sep. 26-30, 1994.*
Acevedo et al., "Bacterial outer membrane vesicles and vaccine applications" *Frontiers in Immunology* 5(121): 6 pages (Mar. 24, 2014).
Bidmos et al., "Cross-reactive bactericidal antimeningococcal antibodies can be isolated from convalescing invasive meningococcal disease patients using reverse vaccinology 2.0," *Frontiers in Immunology* 9(1621): 9 pages (Jul. 2018).
Claassen et al., "Production, characterization and control of a *Neisseria meningitidis* hexavalent class 1 outer membrane protein causing vesicle vaccine," *Vaccine* 14(10): 1001-1008 (Nov. 10, 1996).
Dull and McIntosh, "Meningococcal vaccine development—from glycoconjugates against MenACWY to proteins against MenB—potential for broad protection against meningococcal disease," *Vaccine* 30S:B18-B25 (2012).
Fredriksen et al., "Production, characterization and control of MenB-vaccine «folkehelsa»: an outer membrane vesicle vaccine against group B meningococcal disease," *NIPH Annals* 14(2): 66-78 (Dec. 1991).
Keiser et al., "A phase 1 study of a meningococcal native outer membrane vesicle vaccine made from a group B strain with deleted 1pxL1 and synX, over-expressed factor H binding protein, two PorAs and stabilized OpcA expression," *Vaccine* 29:1413-1420 (available on-line Jan. 1, 2011).

(Continued)

*Primary Examiner* — Sarvamangala Devi
(74) *Attorney, Agent, or Firm* — Klarquist Sparkman, LLP

(57) ABSTRACT

Immunogenic compositions are disclosed that include *Neisseria meningitidis* microvesicles, such as outer membrane vesicles (OMV) and/or blebs, from PorA⁻PorB⁻ *Neisseria*, such as PorA⁻PorB⁻RmpM⁻ *Neisseria meningitidis*. These immunogenic compositions are of use to induce an immune response to *Neisseria*, including *Neisseria meningitidis* and *Neisseria gonorrhea*.

Figure 1B:
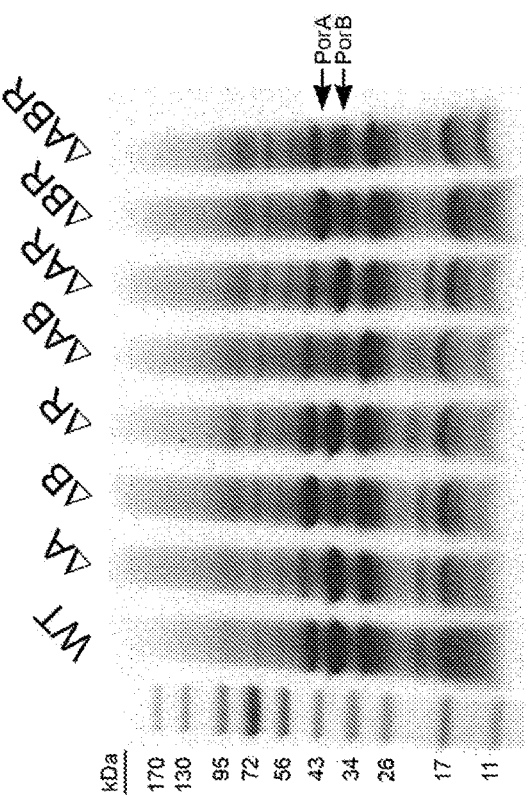

18 Claims, 18 Drawing Sheets
Specification includes a Sequence Listing.

(56) References Cited

OTHER PUBLICATIONS

Lucidarme et al., "Characterization of fHbp, nhba (gna2132), nadA, porA, and sequence type in group B meningococcal case isolates collected in England and Wales during Jan. 2008 and potential coverage of an investigational group B meningococcal vaccine," *Clinical and Vaccine Immunology* 17(6): 919-929 (E-Pub Apr. 7, 2010).

Martin et al., "The VR2 epitope on the PorA P1.7-2,4 protein is the major target for the immune response elicited by the strain-specific group B meningococcal vaccine MeNZB," *Clinical Vaccine Immunology* 13(4): 486-491 (Apr. 2006).

Matthais et al., "A cOMPlex problem: heterogeneity in non-epitope loops disrupts meningococcal PorB-specific antibody binding," *20th International Pathogenic Neisseria Conference*, one page (Sep. 4-9, 2016) (Abstract).

Matthais et al., "A cOMPlex problem: targeting meningococcal proteins for serogroup B vaccine design," *ASM*, one page (Jun. 16-20, 2016) (Abstract).

Matthias et al., "A cOMPlex problem: heterogeneity in non-epitope loops disrupts meningococcal PorB specific antibody binding," *IPNC* Poster (Jul. 29-31, 2016).

Matthias et al., "A cOMPlex problem: Targeting meningococcal proteins for serogroup B vaccine design," *ASM* Poster Presentation (Jun. 16-20, 2016).

Matthias et al., "Deletion of the major porin proteins PorA and PorB from outer membrane vesicle vaccines enhances elicitation of cross protective antibodies against serogroup B *Neisseria meningitidis*," *ASM* Poster Presentation (Jun. 9, 2018).

Matthias et al., "Immunization with porin-deficient meningococcal outer membrane vesicles enhances gonococcal clearance in a mouse model of infection," abstract, *21st International Pathogenic Neisseria Conference* one page (Sep. 23-28, 2018) (Abstract).

Matthias et al., "Interaction of Neisseria meningitidis PorB with PorA and RmpM Outer Membrane Proteins Does Not Impact Binding of PorB-Specific Antibodies," *ASM*, 2 pages (Jun. 1, 2015)(Abstract).

Matthias et al., "Meningococcal vesicle vaccines deleted for major outer membrane proteins enhance gonococcal clearance in a murine model," *STI CBER Conference* 2 pages (2019)(Abstract).

Matthias et al., "Meningococcal vesicle vaccines deleted for major outer membrane proteins enhance gonococcal clearance in a murine model," *STI CBER Conference* Presentation 18 pages (2019).

Matthias, "A cOMPlex problem: targeting meningococcal proteins for serogroup B vaccine design," *CBER Science Day* Power Point Presentation, 13 pages (2016).

Matthias, "Interaction of *Neisseria meningitidis* PorB with PorA and RmpM outer membrane proteins does not impact binding of PorB specific antibodies," *ASM* Power Point Presentation, 29 pages (2015).

Moran et al., Analysis of the bactericidal response to an experimental *Neisseria meningitidis* vesicle vaccine, *Clinical and Vaccine Immunology* 19(5): 659-665 (e-Pub Mar. 29, 2012).

Peak et al., "*Neisseria meningitidis* lacking the major porins PorA and PorB are viable and modulate apoptosis and the oxidative burst of neutrophils," *J. Proteome Res.* 15(8): 2356-2365 (Aug. 5, 2016).

Petousis-Harris and Radcliff, "Exploitation of *Neisseria meningitidis* Group B OMV vaccines against *N. gonorrhoeae* to inform the development and deployment of effective gonorrhea vaccines," *Frontiers in Immunology* 10(683): 11 pages (Apr. 9, 2019).

Price et al., "Comparison of different serogroup A immunoassays following a single dose of either MenAfriVac or quadrivalent polysaccharide vaccine in healthy Africans 2-to 29-years of age," *IPNC* one page (Oct. 12-17, 2014).

Zollinger et al., "Phase I study of *Neisseria meningitidis* liposomal vaccine containing purified outer membrane proteins and detoxified lipooligosaccharide," *Vaccine* 30: 712-721 (e-Pub Dec. 3, 2011).

Christodoulides and Heckles, "Novel approaches to Neisseria meningitidis vaccine Design," *Pathogens and Disease* 75(3): 16 pages (e-Pub Mar. 22, 2017).

International Search Report and Written Opinion from parent PCT Application No. PCT/US2018/043054, 11 pages (dated Oct. 5, 2018).

Matthias et al., "Heterogeneity in non-epitope loop sequence and outer membrane protein complexes alters antibody binding to the major porin protein PorB in serogroup B *Neisseria meningitidis*," *Molecular Microbiology* 105(6): 934-953 (e-Pub Aug. 1, 2017).

Peak et al., "*Neisseria meningitidis* lacking the major porins PorA and PorB is viable and modulates apoptosis and the oxidative burst of neutrophils," *Journal of Proteome Research* 15: 2356-2365 (Nov. 12, 2015).

Van de Waterbeemd et al., "Improved OMV vaccine against *Neisseria meningitidis* using genetically engineered strains and a detergent-free purification process," *Vaccine* 28: 4810-4816 (e-Pub May 16, 2010).

Whelan et al., "Ecologic Study of Meningococcal B Vaccine and *Neisseria gonorrhoeae* Infection, Norway," *Emerging Infectious Diseases* 22(6): 1137-1139 (Nov. 16, 2011).

Zhang et al., "Improving the immunogenicity of a trivalent *Neisseria meningitidis* native outer membrane vesicle vaccine by genetic modification," *Vaccine* 34(35):4250-4256 (e-Pub Jul. 2, 2016).

\* cited by examiner

Figure 2A:
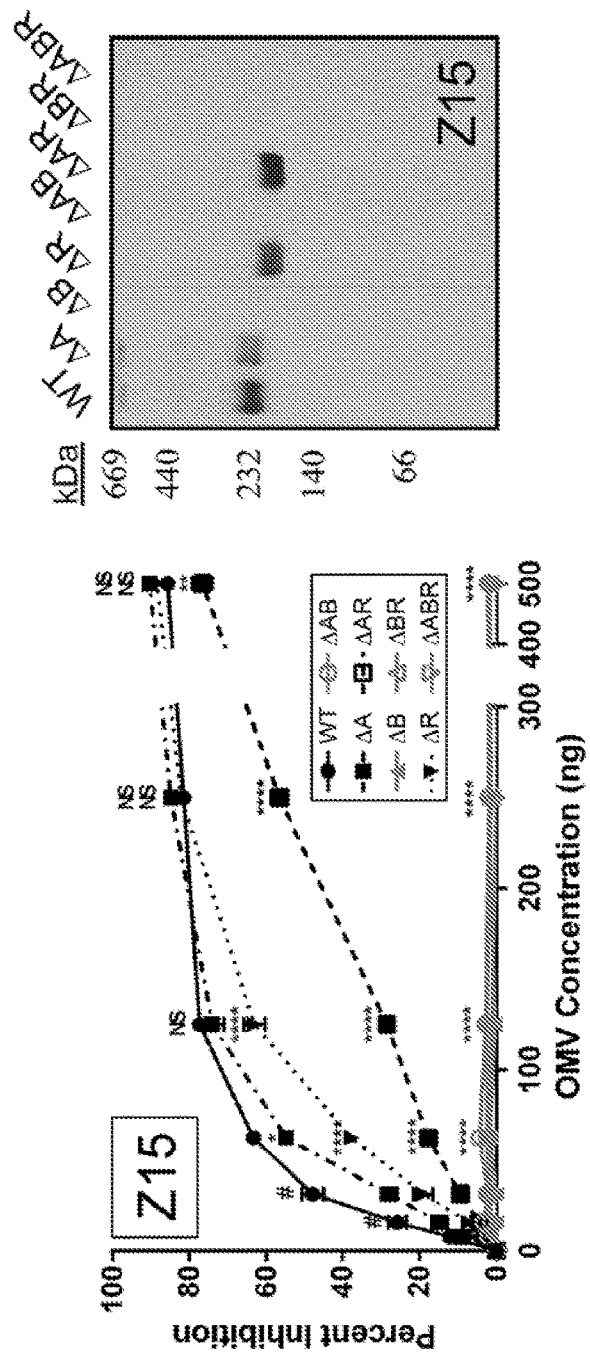

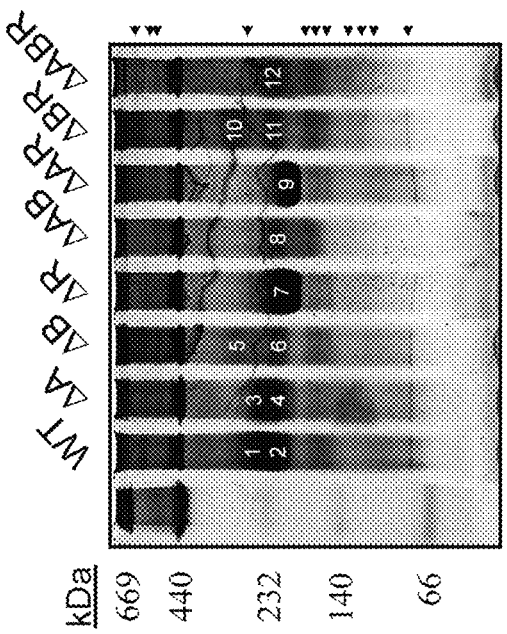
FIG. 2C
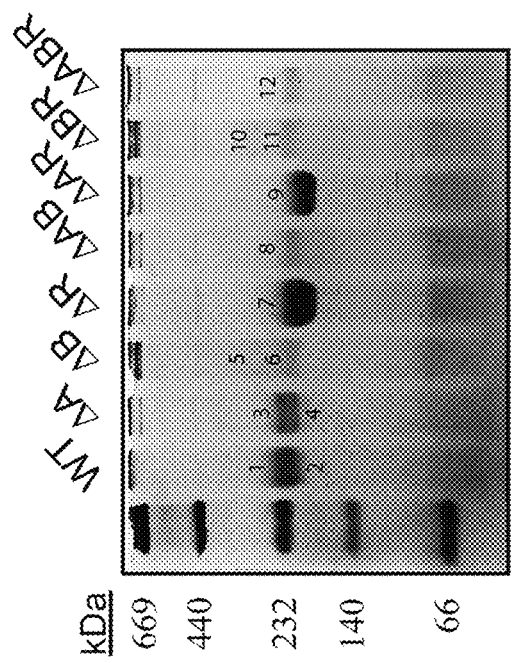

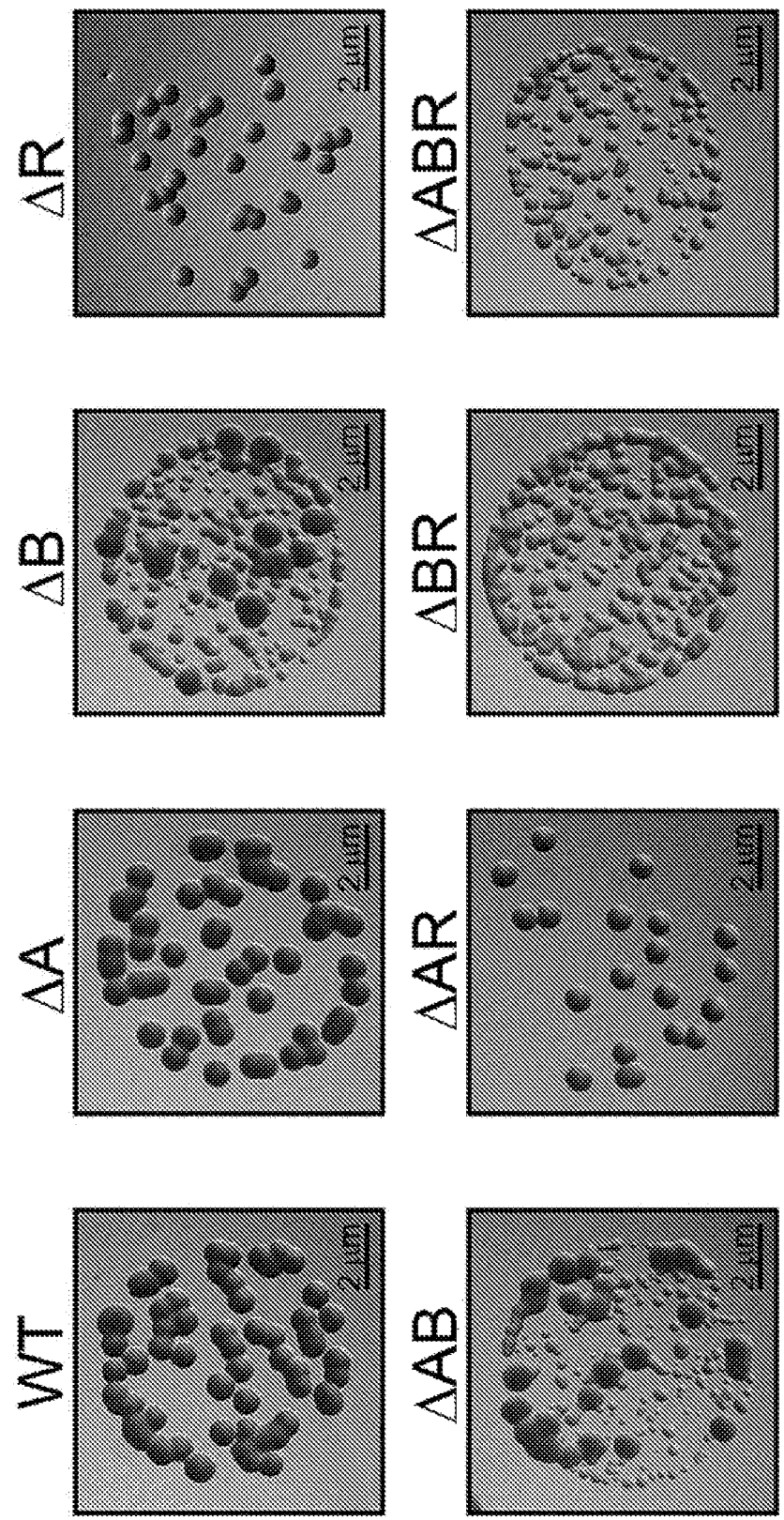

|         | n  | Percent Clearance (Day 5) | Percent Clearance (Day 7) | p-value (vs Alum) | p-value (vs Unimm.) |
|---------|----|---------------------------|---------------------------|-------------------|---------------------|
| MC58    | 18 | 33%                       | 39%                       | 0.2               | 0.09                |
| OCh     | 18 | 17%                       | 56%                       | 0.03          | 0.01            |
| ΔABR    | 17 | 24%                       | 77%                       | 0.002         | 0.0003          |
| Alum    | 18 | 0%                        | 17%                       | 0.8               |                     |
| Unimm.  | 16 | 6%                        | 19%                       |                   | 0.8                 |

MC58

ΔABR

OCh

Alum

FIG. 11A

```
                         L1
M(1-6)B(7-8)      MKKSLIALTLAALPVAAMADVTLYGTIKAGVETSRSVFHQNGQVTEVTTATGIVDLGSKI
M(1-6)C(7-8)      MKKSLIALTLAALPVAAMADVTLYGTIKAGVETSRSVFHQNGQVTEVTTATGIVDLGSKI
B(1-4)M(5-6)B(7-8) MKKSLIALTLAALPVAAMADVTLYGTIKAGVETSRSVFHNGGQVVSVETGTGIVDLGSKI
C(1-4)M(5-6)C(7-8) MKKSLIALTLAALPVAAMADVTLYGTIKAGVETSRSVFHNGGQVVSVETGTGIVDLGSKI
B(1-4)M(5-8)      MKKSLIALTLAALPVAAMADVTLYGTIKAGVETSRSVFHNGGQVVSVETGTGIVDLGSKI
C(1-4)M(5-8)      MKKSLIALTLAALPVAAMADVTLYGTIKAGVETSRSVFHNGGQVVSVETGTGIVDLGSKI
C(1-6)M(7-8)      MKKSLIALTLAALPVAAMADVTLYGTIKAGVETSRSVFHNGGQVVSVETGTGIVDLGSKI
B(1-6)M(7-8)      MKKSLIALTLAALPVAAMADVTLYGTIKAGVETSRSVFHNGGQVVSVETGTGIVDLGSKI
M(1-4)C(5-6)M(7-8) MKKSLIALTLAALPVAAMADVTLYGTIKAGVETSRSVFHQNGQVTEVTTATGIVDLGSKI
M(1-4)B(5-6)M(7-8) MKKSLIALTLAALPVAAMADVTLYGTIKAGVETSRSVFHQNGQVTEVTTATGIVDLGSKI
M(1-4)B(5-8)      MKKSLIALTLAALPVAAMADVTLYGTIKAGVETSRSVFHQNGQVTEVTTATGIVDLGSKI
M(1-4)C(5-8)      MKKSLIALTLAALPVAAMADVTLYGTIKAGVETSRSVFHQNGQVTEVTTATGIVDLGSKI
OCh               MKKSLIALTLAALPVAAMADVTLYGTIKAGVETSRSVFHQNGQVTEVTTATGIVDLGSKI
                  *****************************       *  *** *  * ***********

L2
M(1-6)B(7-8)      GFKGQEDLGNGLKAIWQVEQRASIAGTDSGWGNRQSFIGLKGGFGKLRVGRLNSVLKDTG
M(1-6)C(7-8)      GFKGQEDLGNGLKAIWQVEQRASIAGTDSGWGNRQSFIGLKGGFGKLRVGRLNSVLKDTG
B(1-4)M(5-6)B(7-8) GFKGQEDLGNGLKAIWQVEQRASIAGTDSGWGNRQSFIGLKGGFGKLRVGRLNSVLKDTG
C(1-4)M(5-6)C(7-8) GFKGQEDLGNGLKAIWQVEQRASIAGTDSGWGNRQSFIGLKGGFGKLRVGRLNSVLKDTG
B(1-4)M(5-8)      GFKGQEDLGNGLKAIWQVEQRASIAGTDSGWGNRQSFIGLKGGFGKLRVGRLNSVLKDTG
C(1-4)M(5-8)      GFKGQEDLGNGLKAIWQVEQRASIAGTDSGWGNRQSFIGLKGGFGKLRVGRLNSVLKDTG
C(1-6)M(7-8)      GFKGQEDLGNGLKAIWQVEQRASIAGTDSGWGNRQSFIGLKGGFGKLRVGRLNSVLKDTG
B(1-6)M(7-8)      GFKGQEDLGNGLKAIWQVEQRASIAGTDSGWGNRQSFIGLKGGFGKLRVGRLNSVLKDTG
M(1-4)C(5-6)M(7-8) GFKGQEDLGNGLKAIWQVEQRASIAGTDSGWGNRQSFIGLKGGFGKLRVGRLNSVLKDTG
M(1-4)B(5-6)M(7-8) GFKGQEDLGNGLKAIWQVEQRASIAGTDSGWGNRQSFIGLKGGFGKLRVGRLNSVLKDTG
M(1-4)B(5-8)      GFKGQEDLGNGLKAIWQVEQRASIAGTDSGWGNRQSFIGLKGGFGKLRVGRLNSVLKDTG
M(1-4)C(5-8)      GFKGQEDLGNGLKAIWQVEQRASIAGTDSGWGNRQSFIGLKGGFGKLRVGRLNSVLKDTG
OCh               GFKGQEDLGNGLKAIWQVEQRASIAGTDSGWGNRQSFIGLKGGFGKLRVGRLNSVLKDTG
                  ************************************************************

L3                          L4
M(1-6)B(7-8)      DINPWDSKSDYLGVNKIAEPEARLISVRYDSPEFAGLSGSVQYALNDNAGRHNSESYHAG
M(1-6)C(7-8)      DINPWDSKSDYLGVNKIAEPEARLISVRYDSPEFAGLSGSVQYALNDNAGRHNSESYHAG
B(1-4)M(5-6)B(7-8) DINPWDSKSDYLGVNKIAEPEARLISVRYDSPEFAGLSGSVQYALNDNAGKYNSESYHAG
C(1-4)M(5-6)C(7-8) DINPWDSKSDYLGVNKIAEPEARLISVRYDSPEFAGLSGSVQYALNDNAGKYNSESYHAG
B(1-4)M(5-8)      DINPWDSKSDYLGVNKIAEPEARLISVRYDSPEFAGLSGSVQYALNDNAGRHNSESYHAG
C(1-4)M(5-8)      DINPWDSKSDYLGVNKIAEPEARLISVRYDSPEFAGLSGSVQYALNDNAGKYNSESYHAG
C(1-6)M(7-8)      DINPWDSKSDYLGVNKIAEPEARLISVRYDSPEFAGLSGSVQYALNDNAGKYNSESYHAG
B(1-6)M(7-8)      DINPWDSKSDYLGVNKIAEPEARLISVRYDSPEFAGLSGSVQYALNDNAGRHNSESYHAG
M(1-4)C(5-6)M(7-8) DINPWDSKSDYLGVNKIAEPEARLISVRYDSPEFAGLSGSVQYALNDNAGRHNSESYHAG
M(1-4)B(5-6)M(7-8) DINPWDSKSDYLGVNKIAEPEARLISVRYDSPEFAGLSGSVQYALNDNAGRHNSESYHAG
M(1-4)B(5-8)      DINPWDSKSDYLGVNKIAEPEARLISVRYDSPEFAGLSGSVQYALNDNAGRHNSESYHAG
M(1-4)C(5-8)      DINPWDSKSDYLGVNKIAEPEARLISVRYDSPEFAGLSGSVQYALNDNAGRHNSESYHAG
OCh               DINPWDSKSDYLGVNKIAEPEARLISVRYDSPEFAGLSGSVQYALNDNAGKYNSESYHAG
                  ********************************************** *  **
```

FIG. 11B

NEISSERIA MENINGITIDIS IMMUNOGENIC COMPOSITIONS

CROSS REFERENCE TO RELATED APPLICATION

This is a § 371 U.S. national stage of International Application No. PCT/US2018/043054, filed Jul. 20, 2018, which claims the benefit of U.S. Provisional Application No. 62/535,627, filed Jul. 21, 2017, which is incorporated herein by reference.

FIELD OF THE DISCLOSURE

This relates to immunogenic compositions comprising outer membrane microvesicles, which include outer membrane vesicles (OMVs) and/or blebs, from PorA$^-$PorB$^-$ Neisseria, such as PorA$^-$PorB$^-$RmpM$^-$ Neisseria (N.) meningitidis, that are of use to induce an immune response to Neisseria, including N. meningitidis and N. gonorrhoeae.

BACKGROUND

Neisseria is a genus of Gram-negative bacteria that colonize the mucosal surfaces of many animals. There are eleven species that colonize human, of which two, N. meningitidis and N. gonorrhoeae, are pathogenic. N. meningitidis is the causative agent of meningitis and meningococcal septicemia. N. gonorrhoeae is the causative agent of gonorrhea. The genomes of at least ten of the Neisseria species have been completely sequenced.

Diseases caused by N. meningitidis and N. gonorrhoeae are significant health problems worldwide; control of these diseases by developing meningococcal and gonococcal vaccines is a public health priority. However, development of vaccines has been challenging.

N. meningitidis remains a significant cause of global morbidity and mortality, despite the availability of serogroup A-, C-, W-, and Y-specific capsular polysaccharide (Ps) vaccines. Disease can be caused by meningococcal serogroup B (MenB) strains, which in the United States account for one-third of all invasive N. meningitidis infections and 60% of those in infants (Prevention, C.f.D.C.a., (2015) Meningococcal Disease. In: Epidemiology and Prevention of Vaccine-Preventable Diseases. J. Hamborsky, A. Kroger & C. Wolfe (eds). Washington, D.C.: Public Health Foundation, pp. 231-246). Unlike the other meningococcal serogroups, the capsule of MenB is poorly immunogenic (Wyle et al. (1972). J Infect Dis 126: 514-521), a result of its resemblance to a polysialylated Ps moiety present on human neural cells (Finne et al. (1987) J Immunol 138: 4402-4407). Efforts for vaccine design have focused on identification of subcapsular antigens, including surface-expressed outer membrane proteins (OMPs). However, a need remains for additional vaccines. In addition, N. gonorrhoeae is an unencapsulated bacterium and currently no effective gonococcal vaccines exist. A need remains for additional compositions that can be used to induce an immune response to N. meningitidis and N. gonorrhoeae.

SUMMARY OF THE DISCLOSURE

Disclosed are isolated PorA$^-$PorB$^-$RmpM$^-$ Neisseria (N.) meningitidis (also called ΔPorAΔPorBΔRmpM) and compositions including an effective amount of outer membrane microvesicles (such as OMVs and blebs) produced from these PorA$^-$PorB$^-$RmpM$^-$ N. meningitidis. Also disclosed are methods for using these compositions to induce an immune response to *Neisseria*, such as *N. meningitidis* and *N. gonorrhoeae*.

Also disclosed are methods for inducing an immune response to *N. gonorrhoeae* in a mammalian subject. These methods include administering to the mammalian subject an immunogenic composition comprising an effective amount of microvesicles from $PorA^{-}PorB^{-}$ *N. meningitidis* and a pharmaceutically acceptable carrier, thereby inducing the immune response to *N. gonorrhoeae*.

The foregoing and other features and advantages of the invention will become more apparent from the following detailed description of several embodiments which proceeds with reference to the accompanying figures.

BRIEF DESCRIPTION OF THE FIGURES

FIGS. 1A-1B. Construction of outer membrane protein (OMP) deletion mutants. A. Proper deletion of major meningococcal porins PorB and PorA in isogenic OMP deletion strains as confirmed by dot blot with PorB-specific Z15 and PorA-specific P7 monoclonal antibodies (mAbs), respectively (upper panel). rmpM deletion is confirmed by PCR (lower panel). rmpM (arrow) indicates the presence of the ~1.35 kb gene product and chl (arrow), the ~1.5 kb chloramphenicol resistance cassette introduced during double homologous recombination. B. COOMASSIE®-stained SDS-PAGE gel of OMVs confirms PorA and PorB deletion and reveals no large disruption in unrelated protein expression. An increase in PorA for the PorB single deletion ΔB and the PorB/RmpM double deletion ΔBR is detectable. ΔA, ΔB, and ΔR are indicative of PorA, PorB, and RmpM deletion, respectively, where multiple letters indicate multiple deletions. Data are representative of two independent experiments.

FIGS. 2A-2C. OMP deletion diminishes PorB-specific antibody binding and alters the formation of PorB-containing OMP complexes. A. Deletion of PorA and RmpM decreases the ability of OMVs to inhibit binding of PorB-specific mAb Z15 to MC58 recombinant PorB (rPorB) in a competitive ELISA (left panel). When fractionated by blue native gel electrophoresis (BNGE) and transferred to a polyvinylidene difluoride (PVDF) membrane, Z15 binds all PorB-containing OMVs, though deletion of rmpM singly (ΔR) or in combination with porA (ΔAR) induces formation of a single dominant PorB-containing complex that is of lower molecular weight (MW) than the wild type (WT) (right panel). B. Of the PorA-containing OMVs, only ΔR exhibits decreased binding of the PorA-specific P7 mAb in rPorA competitive ELISAs (left panel). ΔB and ΔBR are characterized by formation of four large MW PorA-containing complexes (right panel). C. Fractionation of OMVs, followed by visualization with either COOMASSIE® stain (upper panel) or silver stain (lower panel), demonstrates the presence of unique dominant bands representative of OMP complexes for each of the deletion mutants. The four porB deletion mutants (ΔB, ΔAB, ΔBR, ΔABR) exhibit the largest alteration in OMP complex banding profile. Numbers correlate with complexes analyzed by mass spectrometry in Table 2. Bands visualized by silver stain that are observed in OMVs obtained from multiple OMV types are indicated by arrows. For ELISAs in A and B, data represent the mean±SEM of duplicates of ≥3 independent experiments. * above each point represents statistical significance relative to WT OMVs, where #indicates $P<0.0001$ for binding to all other OMVs relative to WT. *$P<0.05$, $P<0.01$, *$P<0.001$, ****$P<0.0001$ by two-way ANOVA with Tukey's multiple comparisons post-test. NS=not significant. Gels and immunoblots are representative of at least 2 independent experiments.

Figure 3A:
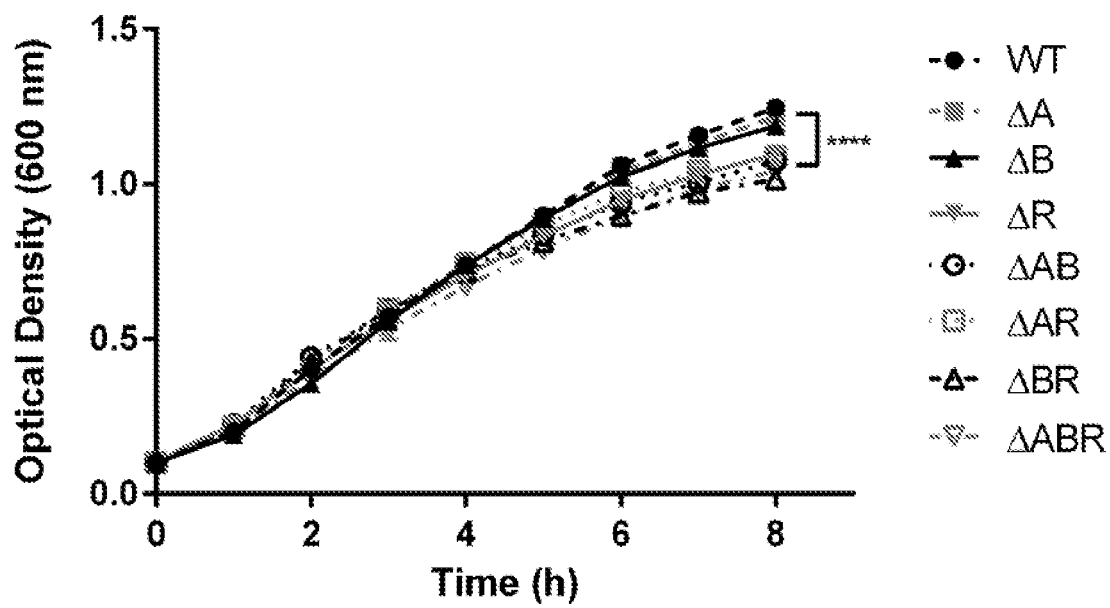
Figure 3B:
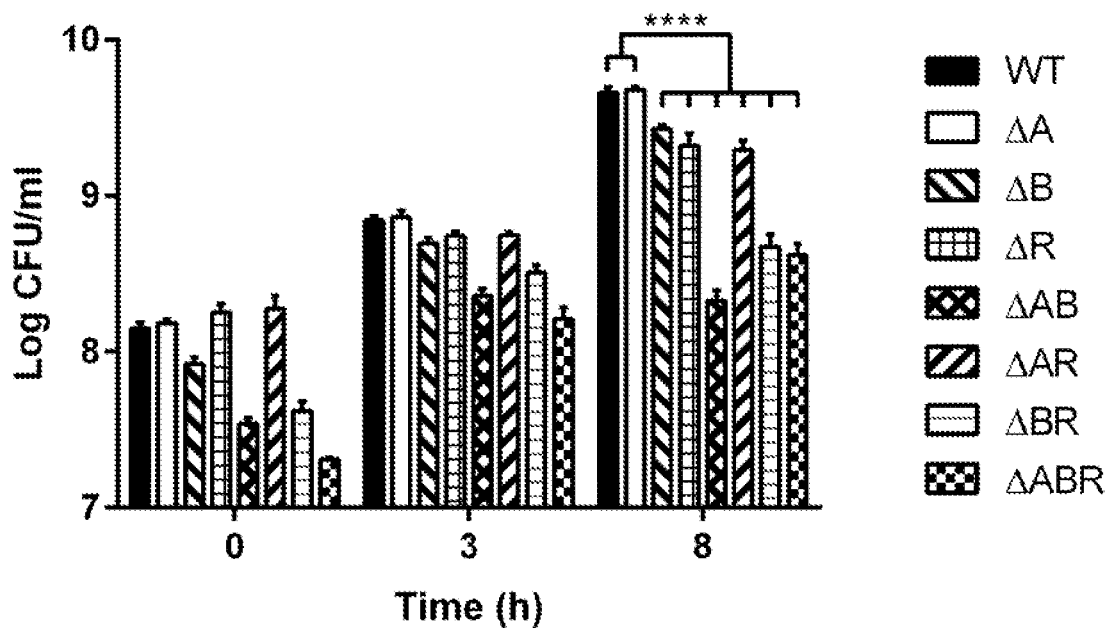

FIGS. 3A-3C. PorB deletion strains exhibit defects in growth. A. Growth curve of MC58 OMP deletion strains. ΔA and ΔB grow at a rate equivalent to the WT in TSB broth. All other strains exhibit a slight but statistically significant defect in growth relative to the others. Strains deleted for porB expression produce fewer (B) and smaller (C) colony forming units (CFUs) relative to the other strains. The difference in CFU counts is not significant until late exponential/stationary phase (8 h of growth). Data represent the mean±SEM of duplicates of >3 independent experiments. ****$P<0.0001$ by two-way ANOVA with Tukey's multiple comparisons post-test. C is representative of two independent experiments.

Figure 4:
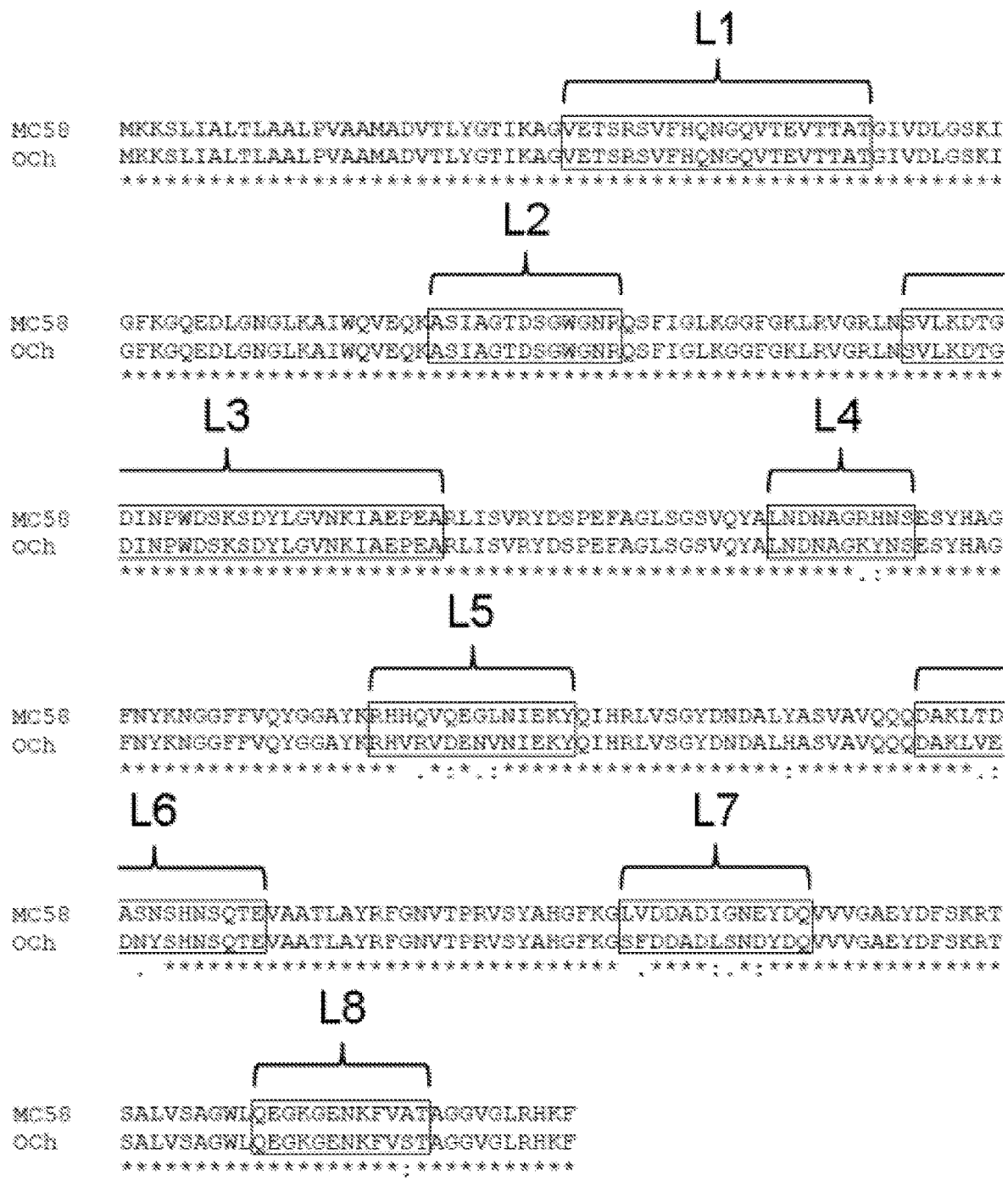

FIG. 4. ClustalW (MUSCLE, EMBL-EBI) alignment of the PorB types of the WT MC58 strain (SEQ ID NO: 38) and the isogenic PorA-deficient OCh strain (SEQ ID NO: 39). MC58 and OCh PorB types exhibit amino acid sequence homology in variable L1 and structural L2-L3. Variable L4-L8 are heterologous. L1-L8 represent the eight surface-exposed PorB loops.

FIGS. 5A-5D. All OMV antigens induce serum IgG antibodies capable of binding multiple meningococcal strains. A. Rabbit immunization scheme for PorA-deficient OMV vaccine study. Pre-immune blood samples were drawn on the first day of immunization (Day 0) and two weeks following the second (Day 28) and third (Day 56) immunization. Samples were also taken at the termination of the experiment (Day 84) and assessed for the presence of meningococcal-specific antibodies relative to pre-immune samples in whole cell ELISAs (B-D). For B-D, label above the graph indicates strain used to coat whole cell ELISAs. Numeric label (B1-B16) represents the serum sample obtained from each of the 16 immunized rabbits. Label beneath the bar indicates the immunizing antigen for each of the sera. BEXSERO® and PBS with aluminum hydroxide adjuvant alone were used as positive and negative controls, respectively. Data represent the mean±SEM of duplicates of ≥3 independent experiments. *$P<0.0001$ by two-way ANOVA with Tukey's multiple comparisons post-test.

Figure 6:
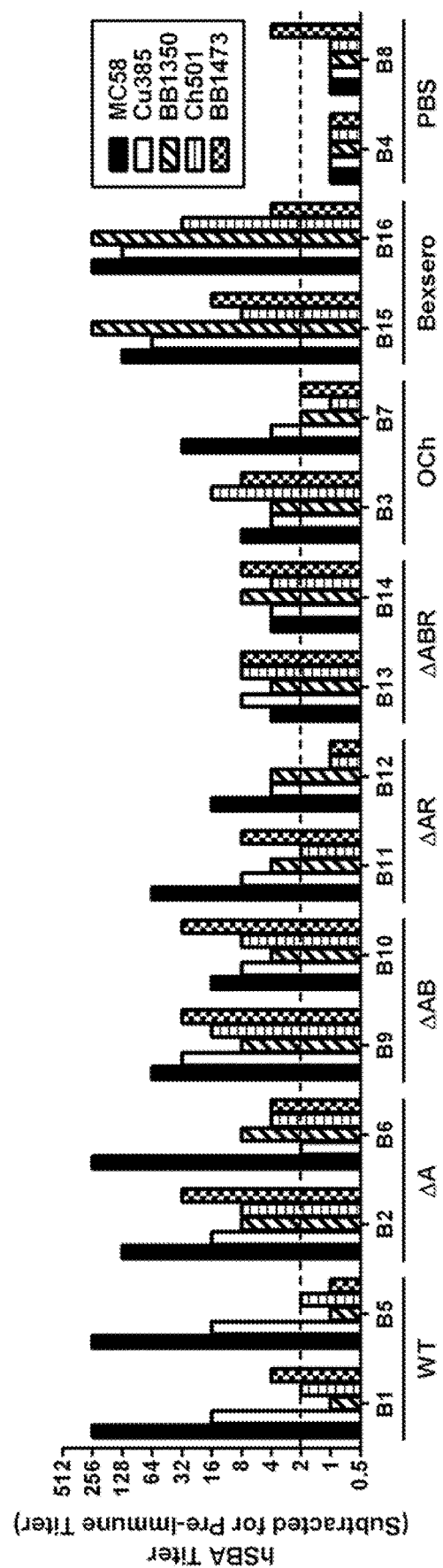

FIG. 6. Selective OMP deletion enhances cross-protective antibody responses. Sera obtained from each of the rabbits immunized with one of the six OMV antigens (WT, ΔA, ΔAB, ΔAR, ΔABR, OCh) or the positive (BEXSERO®) or negative (PBS) control antigens were heat-inactivated and assessed for the ability to kill wild type meningococcal strains MC58 (black bar), Cu385 (white bar), BB1350 (diagonal bar), Ch501 (horizontal bar), and BB1473 (checkered bar) in the presence of human serum (complement source). The only two antigens that were able to induce bactericidal antibody responses from both of the immunized rabbits that were capable of killing all five strains tested were those deleted for both PorA and PorB expression (ΔAB and ΔABR). Numeric label (B1-B16) represents the serum sample obtained from each of the 16 immunized rabbits. Label beneath the bar indicates the immunizing antigen for each of the sera. Hashed line represents threshold of killing (equivalent to 2-fold titers), where titers ≥4-fold (those rising above the hashed line) correlate with protective vaccine responses. Titers depicted represent titers of serum antibodies from final bleed serum subtracted for titers of pre-immune serum.

Figure 7A:
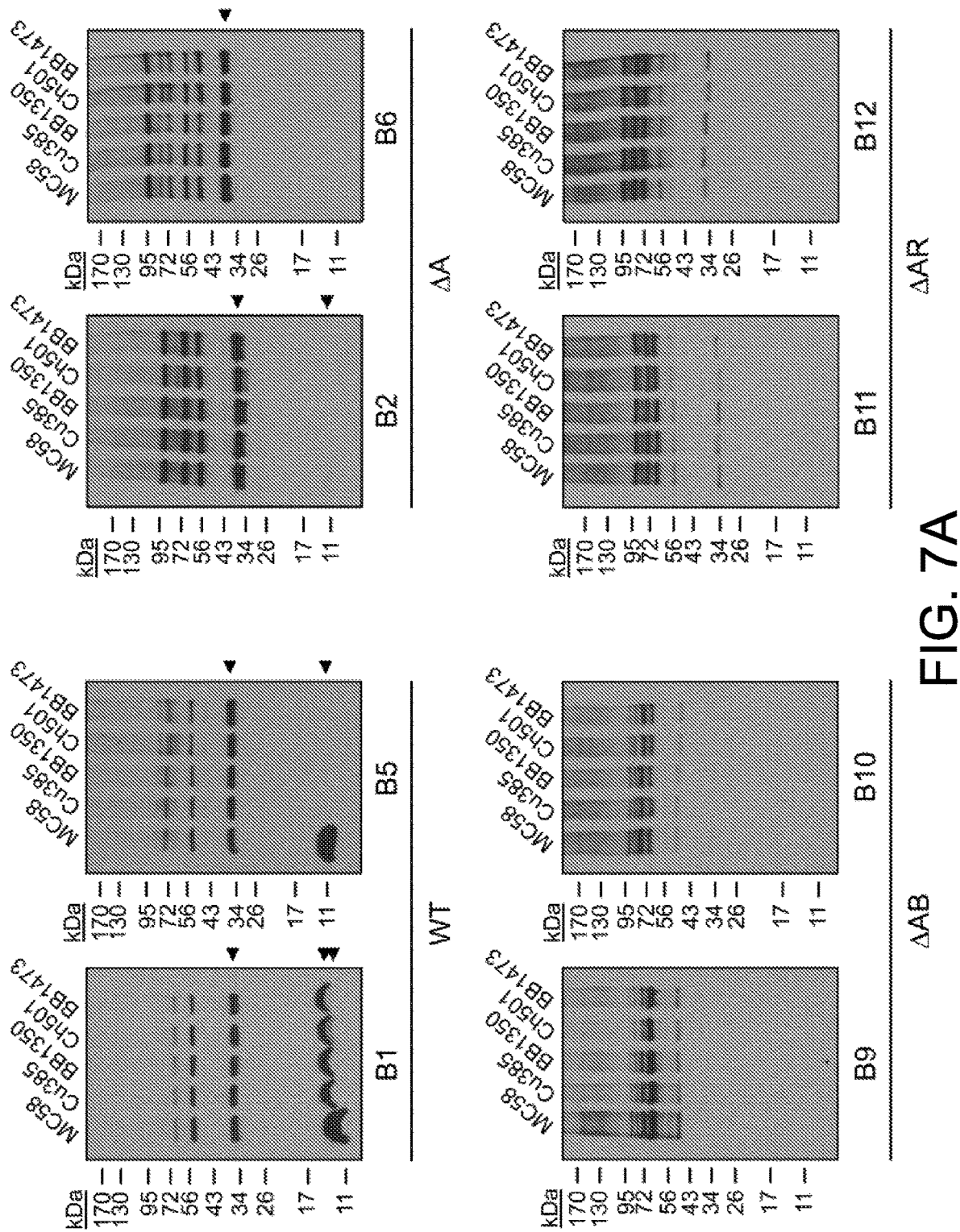
Figure 7B:
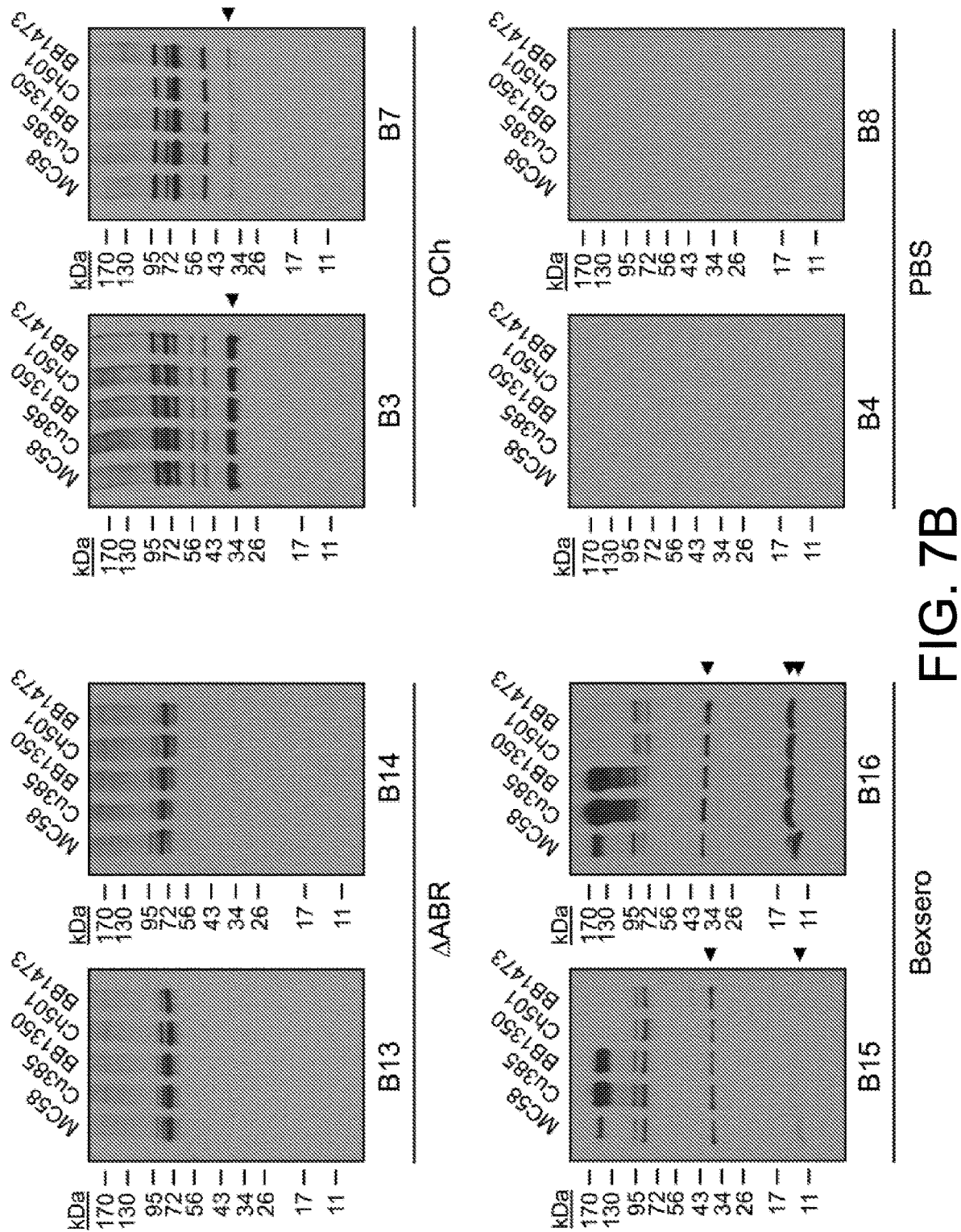

FIGS. 7A-7B. Cross-protective antibody responses correlate with immunogenicity of high MW proteins. Whole cell lysates of MenB strains MC58, Cu385, BB1350, Ch501, and BB1473 were fractionated via SDS-PAGE and blotted to nitrocellulose membranes. Lysates were then probed with terminal sera obtained from each of the 16 immunized rabbits to identify immunogenic meningococcal proteins. Dominant antigens in WT OMV preparations (arrows) are also observed to be strongly immunogenic in PorA single mutant antigens (ΔA and OCh) and the BEXSERO® positive control, which, like the WT, expresses PorA, PorB, and RmpM. Serum antibodies that are capable of killing all meningococcal strains tested in bactericidal assays (ΔAB and ΔABR) lack binding to these bands and instead exhibit binding of high MW bands.

Figure 8:
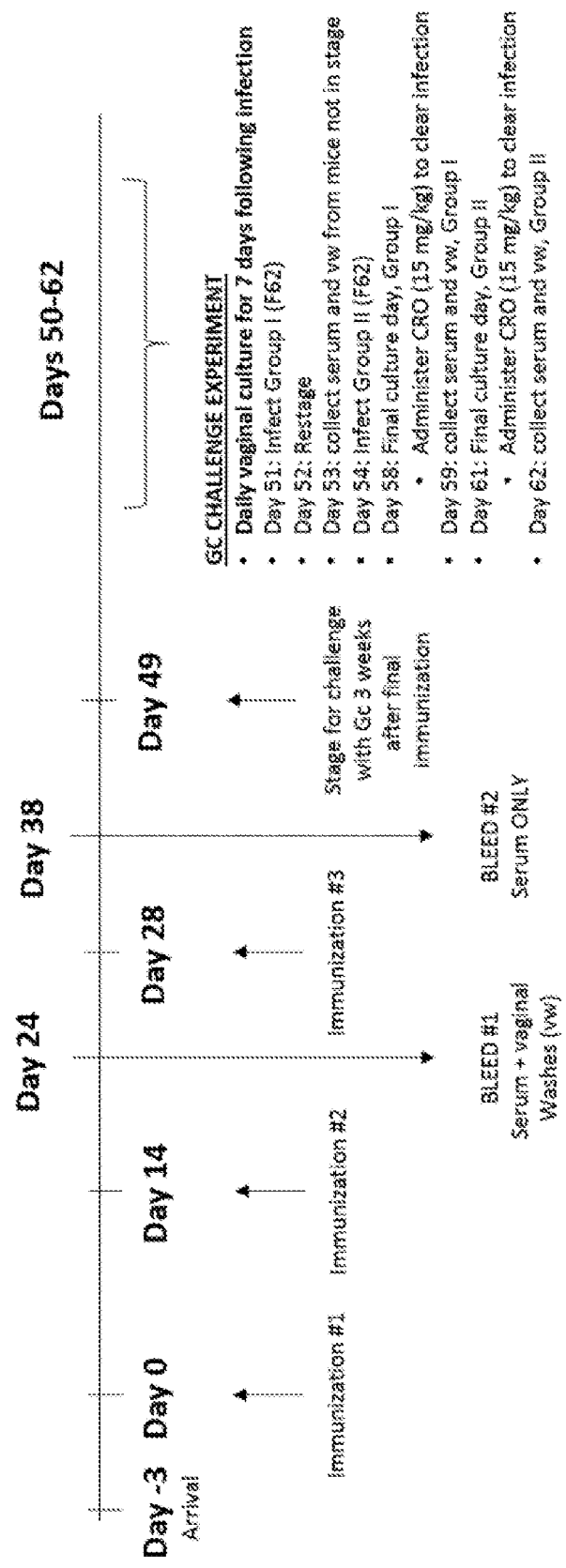

FIG. 8. Mouse immunization/colonization scheme. Mice were immunized with 12.5 µg OMVs/aluminum hydroxide at three fourteen day intervals. Three weeks after the third immunization, mice were administered a cocktail of antibiotics to deplete natural flora and β-estradiol to facilitate staging of the estrous cycle. Animals were then intravaginally inoculated with ~1.5×10$^6$ CFUs of gonococcal strain F62. Vaginal washes were collected at days 1, 3, 5, and 7 post-inoculation to monitor CFU counts and vaginal antibodies.

Figure 9A:
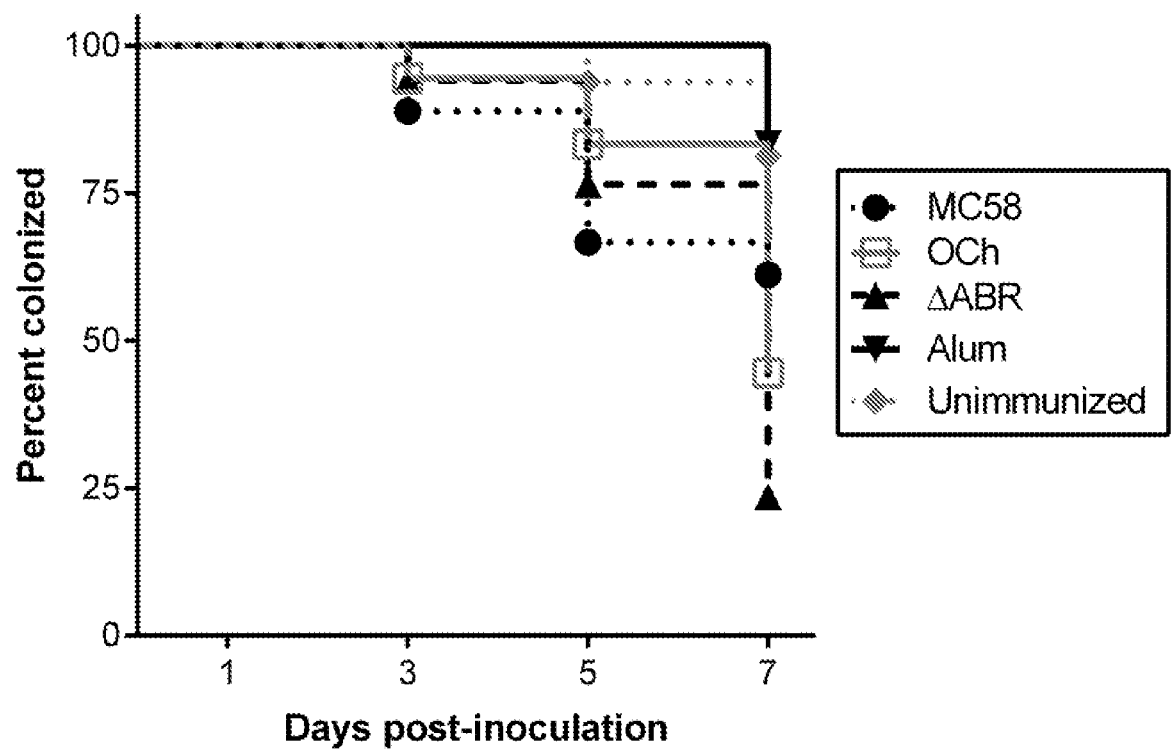
Figure 9B:
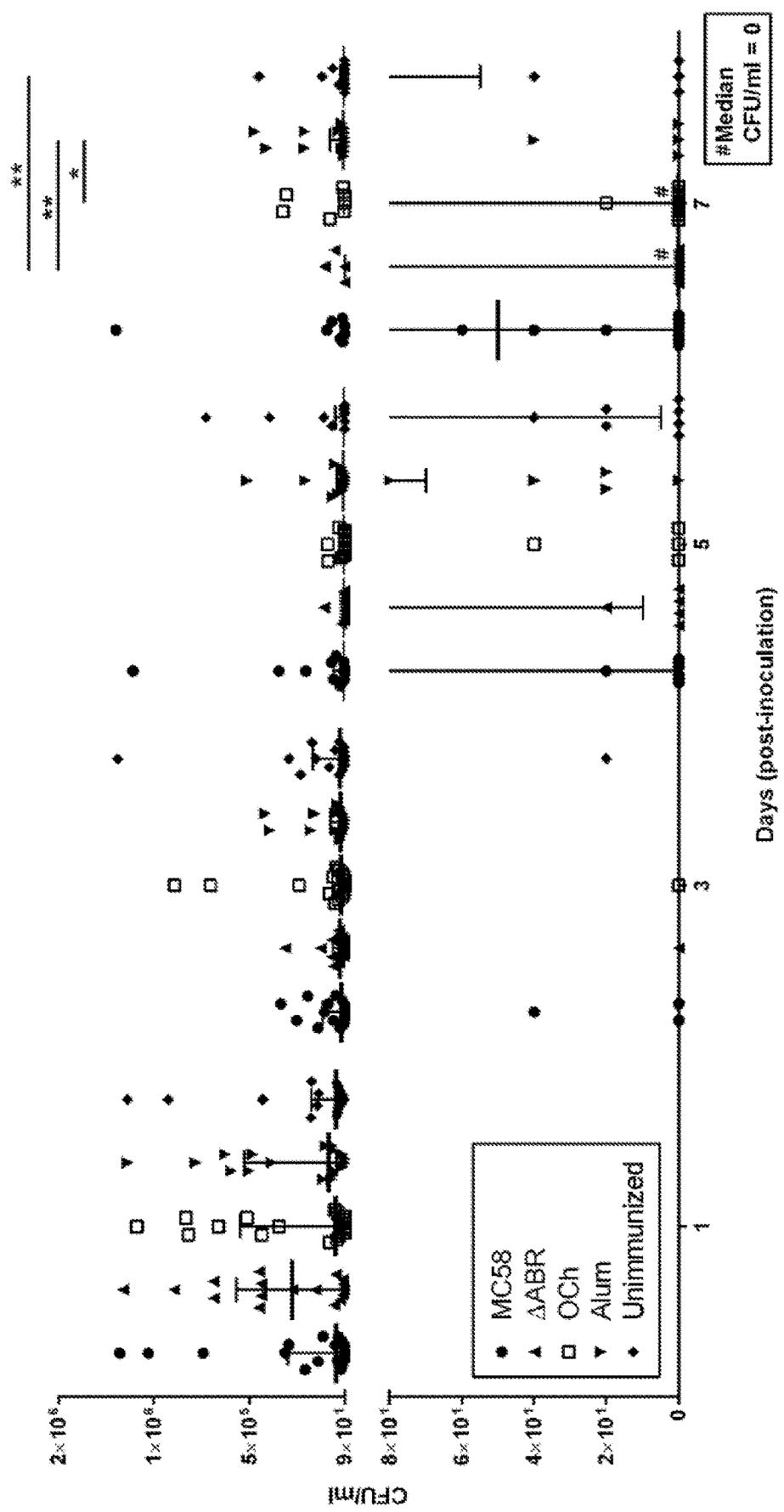

FIGS. 9A-9B. OMV immunization enhances gonococcal clearance in vivo. A. Following immunization, mice were inoculated with gonococcal strain F62 and monitored over a period of one week for clearance of colonization. Mice immunized with OCh (open squares) or ΔABR OMVs (closed upward triangles) exhibited a statistically significant decrease in colonization density by 7 days post-infection (d.p.i.) as assessed by 2-way ANOVA (bold text in table, where $P<0.05$). n represents sample size per group, where uncolonized animals of the initial twenty inoculated were not included in the study. B. F62 colonization densities for individual mice throughout the course of the study. By 7 d.p.i., the median density of colonization for OCh OMV- and ΔABR OMV-immunized mice is equivalent to 0 CFU/ml, while median density for MC58 OMV-immunized animals is 60 CFU/ml. Alum-immunized and unimmunized controls remain largely colonized. Bars represent median±interquartile range of colonization density. *$P<0.05$ and **$P<0.01$ by Mann-Whitney U test.

Figure 10:
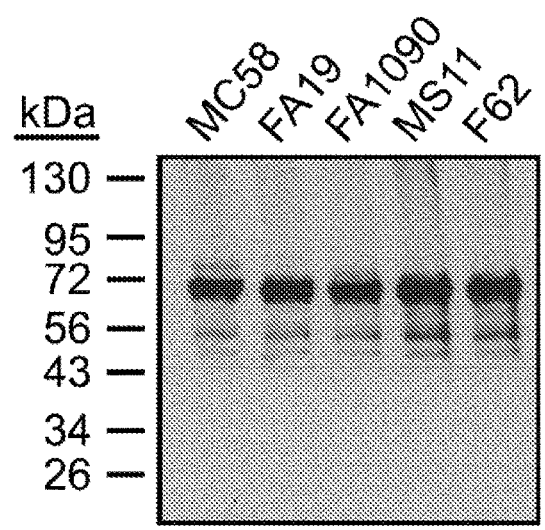
Figure 10:
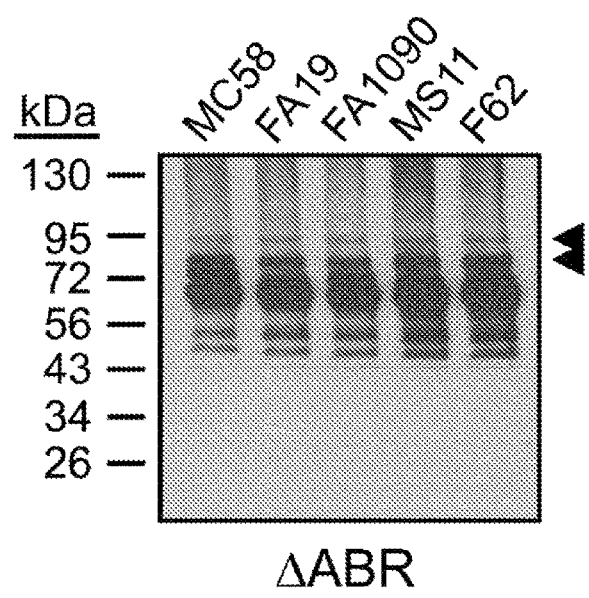
Figure 10:
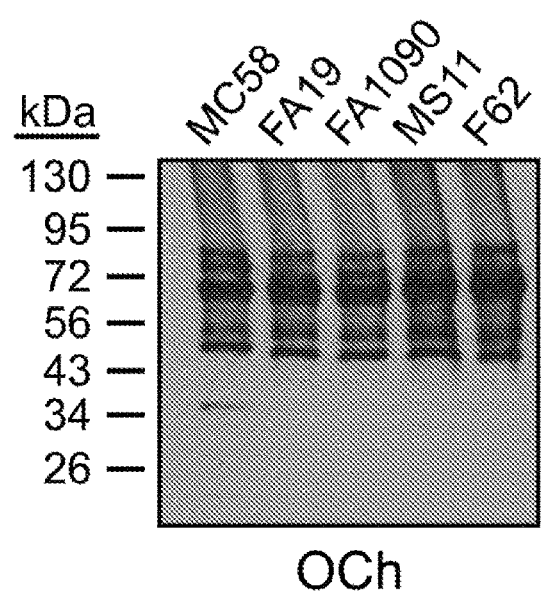
Figure 10:
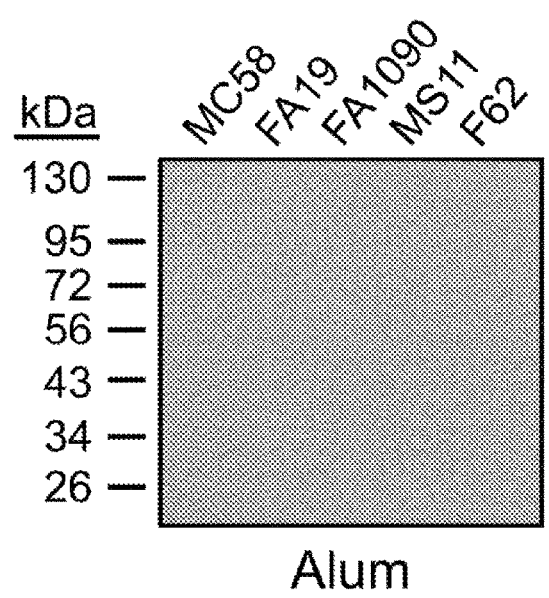

FIG. 10. Antibodies present in pooled sera from OCh OMV- and ΔABR OMV-immunized mice bind to unique high MW proteins that are not bound by serum antibodies from MC58 OMV-immunized mice. Whole cell lysates of gonococcal strains FA19, FA1090, MS11, and F62 were fractionated by SDS-PAGE and blotted to nitrocellulose. Lysates of the parental meningococcal strain used to create the OMV antigens, MC58, was also fractionated as a control. Sera were pooled from all twenty animals in each group following the third immunization and were used to probe the lysates for binding of serum antibodies. Serum antibodies from OCh OMV- and ΔABR OMV-immunized animals bound unique ~70 kDa and ~90 kDa proteins that were not bound by sera from MC58 OMV-immunized animals (arrows). Serum antibodies from aluminum hydroxide-immunized control mice exhibited no binding.

Figure 11B:
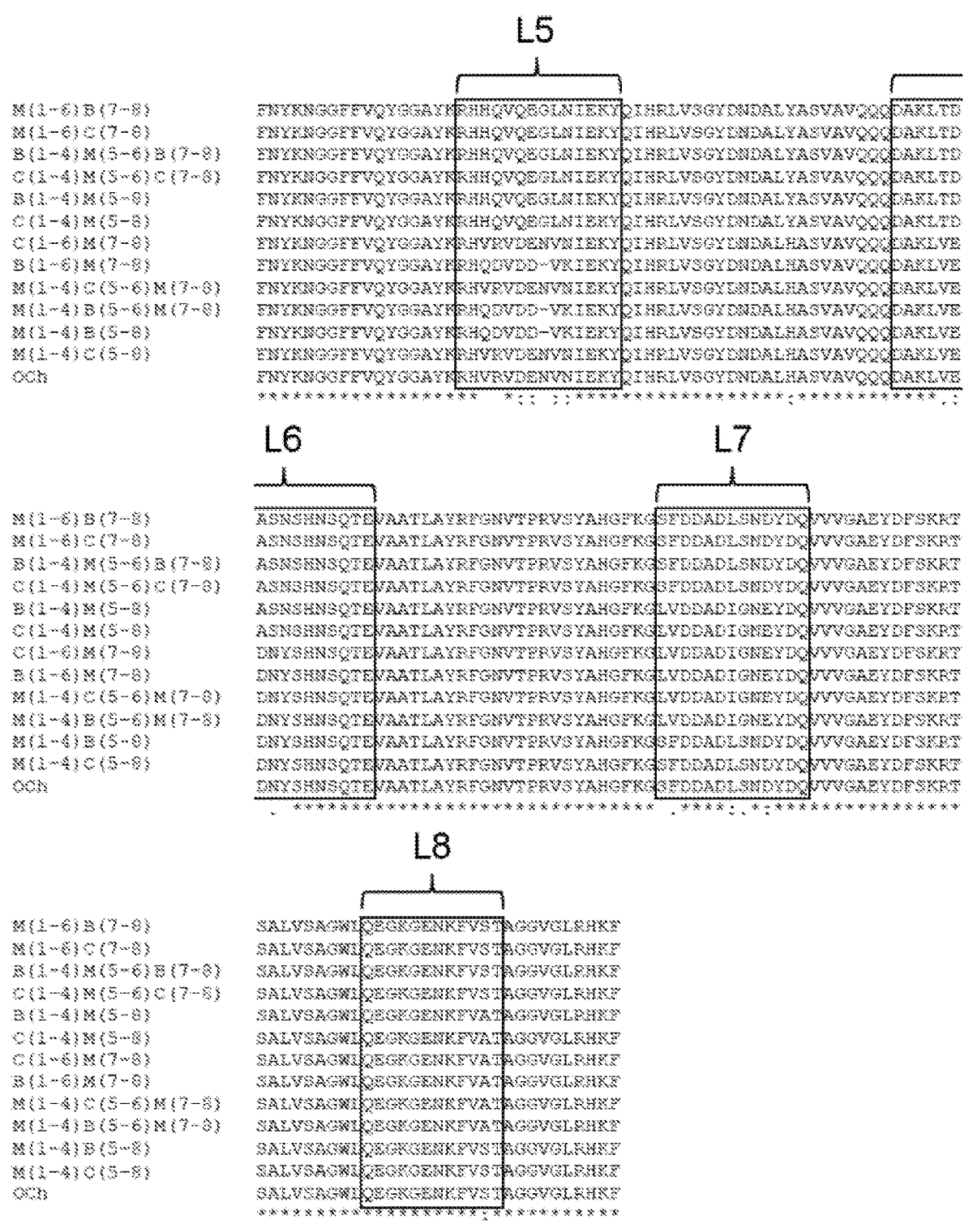

FIGS. 11A-11B. ClustalW (MUSCLE, EMBL-EBI) analysis of the produced chimeric PorB types. L1-L8 represent surface-expressed loops. Shown are OCh (SEQ ID NO: 39), M(1-4)C(5-8)(SEQ ID NO: 40), M(1-6)C(7-8) (SEQ ID NO: 41), M(1-4)C(5-6)M(7-8) (SEQ ID NO: 42), C(1-4)M(5-8) (SEQ ID NO: 43), C(1-6)M(7-8)(SEQ ID NO: 44), C(1-4)M(5-6)C(7-8) (SEQ ID NO: 45), M(1-4)B (5-8) (SEQ ID NO: 46), M(1-6)B(7-8) (SEQ ID NO: 47), M(1-4)B(5-6)M(7-8) (SEQ ID NO: 48), B(1-4)M(5-8) (SEQ ID NO: 49), B(1-6)M(7-8) (SEQ ID NO: 50), and B(1-4)

M(5-6)B(7-8) (SEQ ID NO: 51). The N-terminal portion of each sequence is shown in panel A, and the C-terminal portion of the sequence is shown in panel B.

SEQUENCE LISTING

The nucleic and amino acid sequences listed herein are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "9531-100847-05 Sequence.txt" 46.9 KB, which was created on Jan. 14, 2020, which is incorporated by reference herein. In the accompanying sequence listing:

SEQ ID NOS: 1-37 are the nucleic acid sequence of primers.

SEQ ID NOS: 38-51 are the amino acid sequences of PorB proteins.

DETAILED DESCRIPTION OF SEVERAL EMBODIMENTS

*N. meningitidis* is a Gram-negative bacterium and the causative agent of meningococcal meningitis and septicemia. Its only known host is the human, and it may be carried asymptomatically by approximately 10% of the population (Caugant et al, 1994, J. Clin. Microbiol. 32 323). *N. meningitidis* can express a polysaccharide capsule, and this allows classification of the bacteria according to the nature of the capsule expressed. There are at least twelve serogroups of *N. meningitidis*: A, B, C, 29-E, H, I, K, L, W135, X, Y, and Z, of which serogroups A, B, C, Y, and W cause 90% of meningococcal disease (Poolman et al. (1983) *Infect Immun* 40: 398-406, Infect. Agents and Dis. 4 13). Capsular polysaccharide vaccines directed against serogroups A, C, Y, and W are available; subcapsular vaccines for prevention of serogroup B disease are available but do not target all serotypes and do not provide cross-protection against *N. gonorrhoeae*.

Disclosed herein are compositions that include isolated PorA$^-$PorB$^-$RmpM$^-$ *N. meningitidis*. The isolated PorA$^-$PorB$^-$RmpM$^-$ *N. meningitidis* can be serogroup A, B, or C, or any other serotype Immunogenic compositions can be produced that include outer membrane microvesicles from these PorA$^-$PorB$^-$RmpM$^-$ *N. meningitidis*, such as blebs and/or OMVs, and a pharmaceutically acceptable carrier. Optionally, these pharmaceutical carriers can also include an adjuvant. Optionally, the microvesicles can include a heterologous protein.

It is also disclosed herein that pharmaceutical compositions including a PorA$^-$PorB$^-$ *Neisseria meningitidis*, such as a PorA$^-$PorB$^-$RmpM$^-$ *N. meningitidis*, are of use in inducing an immune response in a subject. The immune response can be a protective immune response or a therapeutic immune response.

In some embodiments, the subject has a *N. meningitidis* infection, and administration of the immunogenic composition increases clearance of the *Neisseria meningitidis*. In other embodiments, the subject has a *N. gonorrhoeae* infection, and administration of the immunogenic composition increases clearance of *N. gonorrhoeae*. In further embodiments, the mammalian subject is a healthy subject. In additional embodiments, the mammalian subject is a human. In some embodiments, the immune response is a protective immune response. In other embodiments, the immune response is a therapeutic response.

In more embodiments, methods are disclosed for including an immune response to *Neisseria gonorrhoeae* in a mammalian subject. These methods include administering to the mammalian subject an immunogenic composition comprising an effective amount of outer membrane microvesicles from PorA$^-$PorB$^-$ *N. meningitidis* and a pharmaceutically acceptable carrier, thereby inducing the immune response to *Neisseria gonorrhoeae*. In some embodiments, the PorA$^-$PorB$^-$ *N. meningitidis* is RmpM$^-$. The microvesicles can be outer membrane vesicles, blebs, or a combination thereof. In specific non-limiting examples, the *N. meningitidis* is serogroup A, B, or C. Optionally, the immunogenic composition further includes an adjuvant.

In some non-limiting examples, the subject has a *Neisseria gonorrhoeae* infection, and administration of the immunogenic composition increases clearance of the *Neisseria gonorrhoeae*. In other non-limiting examples, the mammalian subject does not have an infection with *Neisseria gonorrhoeae* or *Neisseria meningitidis*. In any of the disclosed methods, the mammalian subject can be human.

In other embodiments, compositions are disclosed herein that include genetically modified PorB that are chimeric recombinant combinations of two or more PorB from *N. meningitidis*. Exemplary chimeric recombinant PorB amino acid sequences are shown in FIGS. 11A-11B. Nucleic acid molecules can be produced that encode these chimeric recombinant PorB. An isolated *N. meningitidis* that includes one or more of these proteins is PorB$^+$. An isolated PorA$^-$PorB$^-$ *N. meningitidis* does not include one of these chimeric recombinant PorB proteins.

Summary of Terms

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references. As used herein, the singular forms "a," "an," and "the," refer to both the singular as well as plural, unless the context indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

Administration: The introduction of a composition into a subject by a chosen route. Administration can be local or systemic. For example, if the chosen route is intranasal, the composition is administered by introducing the composition into the nasal passages of the subject. Similarly, if the chosen route is intramuscular, the composition is administered by introducing the composition into a muscle of the subject. If the chosen route is oral, the composition is administered by introducing the subject ingesting the composition. Exemplary routes of administration of use in the methods disclosed herein include, but are not limited to, oral, injection (such as subcutaneous, intramuscular, intradermal, intraperitoneal, and intravenous), sublingual, rectal, transdermal (for example, topical), intranasal, vaginal, and inhalation routes.

Amino acid substitution: The replacement of an amino acid in a polypeptide with one or more different amino acids. In the context of a protein sequence, an amino acid substitution is also referred to as a mutation.

Antibody: An immunoglobulin, antigen-binding fragment, or derivative thereof, that specifically binds and recognizes an analyte (antigen) such as an antigen on a microvesicle (such as an outer membrane vesicle (OMV) or bleb) of Neisseria meningitidis. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity. Non-limiting examples of antibodies include, for example, intact immunoglobulins and variants and fragments thereof that retain binding affinity for the antigen. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, $2^{nd}$ Ed., Springer Press, 2010).

Chimeric Protein: A chimeric protein, also called a hybrid protein, that includes portions of the protein from two different sources. A chimeric PorB includes portions of the PorB from two different sources, such as a portion from N. meningitidis and a portion from N. gonorrhoeae, or a portion from two different serogroups, such as serogroup A, B, C, Y, and W-135. In one embodiment, the different portions can be N-terminal and C-terminal. In other embodiments, specific domains, such as loops, are substituted by the protein from a different source.

Control: A reference standard. In some embodiments, the control is a negative control sample obtained from a healthy patient. In other embodiments, the control is a positive control sample obtained from a patient immunized with a microvesicle (such as an outer membrane vesicle (OMV) or bleb) of Neisseria meningitidis. In still other embodiments, the control is a historical control or standard reference value or range of values (such as a previously tested control sample, such as a group of patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Degenerate variant: In the context of the present disclosure, a "degenerate variant" refers to a polynucleotide encoding a polypeptide that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Effective amount: An amount of agent, such as an immunogen, such as a N. meningitidis microvesicle, that is sufficient to elicit a desired response, such as an immune response in a subject. It is understood that to obtain a protective immune response against an organism of interest can require multiple administrations of a disclosed immunogen, and/or administration of a disclosed immunogen as the "prime" in a prime boost protocol wherein the boost immunogen can be different from the prime immunogen. Accordingly, an effective amount of a disclosed immunogen can be the amount of the immunogen sufficient to elicit a priming immune response in a subject that can be subsequently boosted with the same or a different immunogen to elicit a protective immune response.

In one example, a desired response is to inhibit or reduce or prevent a Neisseria gonorrhoeae or Neisseria meningitidis infection. The Neisseria gonorrhoeae or N. meningitidis infection does not need to be completely eliminated or reduced or prevented for the method to be effective. For example, administration of an effective amount of the agent can decrease the Neisseria gonorrhoeae or N. meningitidis infection (for example, as measured by bacteria number or by number or percentage of subjects infected by Neisseria gonorrhoeae or Neisseria meningitidis) by a desired amount, for example by at least 50%, at least 60%, at least 70%, at least 80%, at least 90%, at least 95%, at least 98%, or even at least 100% (elimination or prevention of detectable hPIV infection), as compared to a suitable control.

Epitope: An antigenic determinant. These are particular chemical groups or peptide sequences on a molecule that are antigenic, such that they elicit a specific immune response, for example, an epitope is the region of an antigen to which B and/or T cells respond. An antibody can bind to a particular antigenic epitope, such as an epitope presented on a microvesicle of Neisseria gonorrhoeae or Neisseria meningitidis. Epitopes can be formed both from contiguous amino acids or noncontiguous amino acids juxtaposed by tertiary folding of a protein.

Heterologous: Originating from a different genetic source, so that the biological components that are not found together in nature. The components may be host cells, genes, or regulatory regions, such as promoters. Although the heterologous components are not found together in nature, they can function together, as when a promoter heterologous to a gene is operably linked to the gene. Another example is where a Neisserial sequence is heterologous to a Neisserial host of a different strain. "Heterologous" as used herein in the context of proteins expressed in two different bacterial strains, e.g., "heterologous PorA."

Immune response: A response of a cell of the immune system, such as a B cell, T cell, or monocyte, to a stimulus, such as Neisseria. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies. A "protective immune response" is an immune response that confers protection against a disease caused by a member of *Neisseria*, such as *N. meningitidis* serogroups, particularly serogroups A, B, C, Y, and W-135, and/or *Neisseria gonorrhoeae*. A "therapeutic immune response" treats an existing infection with *Neisseria*. In some embodiments, the subject has a *N. meningitidis* infection, and administration of the immunogenic composition increases clearance of the *Neisseria meningitidis*. In other embodiments, the subject has a *Neisseria gonorrhoeae* infection, and administration of the immunogenic composition increases clearance of *Neisseria gonorrhoeae*.

Immunogen: A compound, composition, or substance (for example, a composition including outer membrane microvesicles from $PorA^-PorB^-$*Neisseria meningitidis*) that can elicit an immune response in an animal, including compositions that are injected or absorbed into an animal. Administration of an immunogen to a subject can lead to immunity against a pathogen of interest, such as *Neisseria gonorrhoeae* and/or *Neisseria meningitidis*.

Immunogenic composition: A composition comprising outer membrane microvesicles from $PorA^-PorB^-$ *N. meningitidis* that induces a measurable CTL response against *Neisseria gonorrhoeae* and/or *Neisseria meningitidis*, or induces a measurable B cell response (such as production of antibodies) against *Neisseria gonorrhoeae* and/or *Neisseria meningitidis*, when administered to a subject. For in vivo use, the immunogenic composition will typically include outer membrane microvesicles from $PorA^-PorB^-$ *N. meningitidis* in a pharmaceutically acceptable carrier and optionally may also include other agents, such as an adjuvant. The phrase "in an effective amount to elicit an immune response" means that there is a detectable difference between an immune response indicator measured before and after administration of a particular immunogenic composition. Immune response indicators include but are not limited to: antibody titer or specificity, as detected by an assay such as enzyme-linked immunosorbent assay (ELISA), bactericidal assay, flow cytometry, immunoprecipitation, Ouchterlony immunodiffusion; binding detection assays of, for example, spot, western blot or antigen arrays; cytotoxicity assays, etc.

Inhibiting or treating a disease: Inhibiting the full development of a disease or condition, for example, in a subject who is at risk for a disease such as a *Neisseria gonorrhoeae* and/or *N. meningitidis* infection. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. Inhibiting a disease can include preventing or reducing the risk of the disease, such as preventing or reducing the risk of bacterial infection. The beneficial effect can be evidenced, for example, by a delayed onset of clinical symptoms of the disease in a susceptible subject, a reduction in severity of some or all clinical symptoms of the disease, a slower progression of the disease, a reduction in the bacterial load, an improvement in the overall health or well-being of the subject, or by other parameters that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component has been substantially separated or purified away from other biological components, such as other biological components in which the component naturally occurs, such as other chromosomal and extrachromosomal DNA, RNA, membranes, cells and proteins. Microvesicles that have been "isolated" include those purified by standard purification methods. Isolated does not require absolute purity, and can include microvesicles that are at least 50% isolated, such as at least 75%, 80%, 90%, 95%, 98%, 99%, or even 99.9% isolated from other components of the bacteria that product them.

Microvesicles: Outer membrane microvesicles are produced from the outer membrane of *Neisseria*, and include both outer membrane vesicles (OMVs) and blebs. OMVs are produced by solubilizing *Neisseria* in a process wherein the outer membranes form vesicles. Blebs are produced by budding from living *Neisseria*. Methods from the production of outer membrane microvesicles are known in the art, see for example, van de Waterbeemd et al., PLOS One, doi.org/10.1371/journal.pone.0065157, May 31, 2013). OMV and blebs can be purified from intact *Neisseria*, and are generally 100 to 300 nm.

Outer Membrane Protein Reduction Modifiable Protein (Rmp)M: A periplasmic protein from *N. meningitidis* that comprises an N-terminal domain (residues 1-47) and a separate globular C-terminal domain (residues 65-219) responsible for binding to peptidoglycan. The N-terminal fragment of RmpM binds to both the major outer membrane porins, PorA and PorB. Analysis by semi-native SDS-PAGE established that both recombinant full-length RmpM and an N-terminal fragment were sufficient to stabilize the PorA and PorB oligomeric complexes. The meso-diaminopimelate moiety plays a role in peptidoglycan recognition by RmpM. Site-directed mutagenesis showed that two highly conserved residues, Asp120 and Arg135, play a role in peptidoglycan binding, see Maharjan et al., Microbiology 162: 364-375, 2016. See also Li et al., PLOS Biology, doi.org/10.1371/journal.pone.0090525, Mar. 4, 2014 and GENBANK Accession No. X05105.1, as available on Jun. 30, 2018, incorporated herein by reference. The yield of OMV is higher in a *N. meningitidis* strain expressing a truncated N-terminal fragment of RmpM (ΔC-term RmpM) than in a wild-type strain. This strain is also RpmM− as it does not produce funcational RmpM protein. Generally, a $RmpM^-$ *Neisseria* (also called "ΔR") does not produce functional RmpM protein.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the disclosed immunogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol, or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions (such as immunogenic compositions) to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example, an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

Porin (Por)A: PorA is a *Neisseria* porn. PorA monomer topology shows eight extracellular loops (Derrick et al., 1999, Infect. Immun 67 2406-13; van der Ley et al., 1991, Infect. Immun 59 2963) in the protein. The longest loops (1 and 4) are the most variable, hence are referred to as Variable Region 1 (VR1) and Variable Region 2 (VR2). Less variability is seen in loops 5 and 6 (also called semi-variable SVR1 and 2, or variable region 3 and 4, respectively), with essentially no variability in the remaining loops. Loop 3 is predicted to form a "plug" in the pore formed by each subunit of the PorA trimer. Even within VR1 and VR2, most of the variability is confined to residues predicted to form the tip of each loop. Indeed, in both mice and in immunized human volunteers, epitope mapping showed that the majority of the antibody response is directed at the "top" of loops 1 and 4, the region that is variable between strains (van der Voort, et al., 1997, FEMS Immunol. Med. Microbiol. 17 139-48).

This protein generates an immune response in both patients and asymptomatic carriers, to the extent that it has been used as a marker for strain identification, representing the serosubtype system (McGuinness et al., 1990, J Exp Med. 171 1871-82). PorA has been used in effective and registered vaccine formulations and elicits effective bactericidal antibodies. However, strain-to-strain variability in surface loops results in a variable target, and vaccines are typically PorA type-specific. Efforts have been made to generate multivalent PorA vaccines covering up to six different PorA types (van der Voort et al., 1996, Infect Immun. 64 2745-51). A PorA⁻ *Neisseria* (also called ΔA) does not produce functional PorA protein.

Porin B (PorB): A 16-pass transmembrane protein from *Neisseria* that is a porin and forms a β-barrel structure with eight surface-exposed loops (L1-L8) (Tanabe et al. (2010) *Proc Natl Acad Sci USA* 107: 6811-6816). Two of these, L2 and L3, are structural and do not vary considerably in amino acid sequence among different MenB strains. The remaining six, L1 and L4-L8, undergo antigenic variation; it is the binding of antibodies to these loops that forms the basis for meningococcal serotyping (Frasch et al. (1985) *Rev Infect Dis* 7: 504-510). A PorB⁻ *Neisseria* (also called ΔB) does not produce functional PorB protein.

Prime-boost vaccination: An immunotherapy including administration of a first immunogenic composition (the primer vaccine) followed by administration of another immunogenic composition (the booster vaccine) to a subject to induce an immune response. The primer vaccine and/or the booster vaccine are immunogens to which the immune response is directed. The booster vaccine is administered to the subject after the primer vaccine; a suitable time interval between administration of the primer vaccine and the booster vaccine, and examples of such timeframes are disclosed herein. In some embodiments, the primer vaccine, the booster vaccine, or both primer vaccine and the booster vaccine additionally include an adjuvant Recombinant: A recombinant nucleic acid molecule is one that has a sequence that is not naturally occurring, for example, includes one or more nucleic acid substitutions, deletions or insertions, and/or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques.

A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell, or into the genome of a recombinant virus.

Sequence identity: The similarity between amino acid sequences is expressed in terms of the similarity between the sequences, otherwise referred to as sequence identity. Sequence identity is frequently measured in terms of percentage identity; the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. In the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Variants of a polypeptide are typically characterized by possession of at least about 75%, for example, at least about 80%, 85%, 90%, 91%, 92%, 93%, 94%, 95%, 96%, 97%, 98% or 99% sequence identity counted over the full-length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet.

As used herein, reference to "at least 90% identity" (or similar language) refers to "at least 90%, at least 91%, at least 92%, at least 93%, at least 94%, at least 95%, at least 96%, at least 97%, at least 98%, at least 99%, or even 100% identity" to a specified reference sequence.

Serogroup: Classification, such as of *Neisseria meningitidis* by virtue of immunologically detectable variations in the capsular polysaccharide. About 12 serogroups are known: A, B, C, X, Y, Z, 29-E, W-135, H, I, K, and L. Any one serogroup can encompass multiple serotypes and multiple serosubtypes. A serotype is classification of *Neisseria meningitidis* strains based on monoclonal antibody-defined antigenic differences in the outer membrane protein porn PorB, or upon VR typing of amino acid sequences deduced from DNA sequencing. A single serotype can be found in multiple serogroups and multiple serosubtypes. "Serosubtype" is classification of *Neisseria meningitidis* strains based on antibody-defined antigenic variations on the outer membrane protein porin PorA, or upon VR typing of amino acid sequences deduced from DNA sequencing (Sacchi et al., 2000, *J. Infect. Dis.* 182:1169; see also the Multi Locus Sequence Typing web site). Most variability between PorA proteins occurs in two (loops I and IV) of eight putative, surface-exposed loops. The variable loops I and IV have been designated VR1 and VR2, respectively. A single serosubtype can be found in multiple serogroups and multiple serotypes.

Subject: Living multi-cellular vertebrate organisms, a category that includes human and non-human mammals. In an example, a subject is a human. In an additional example, a subject is selected that is in need of inhibiting of a *Neisseria* infection. For example, the subject is either uninfected and at risk for infection, or is infected in need of treatment.

Under conditions sufficient for: A phrase that is used to describe any environment that permits a desired activity.

Vaccine: A preparation of immunogenic material capable of stimulating an immune response, administered for the prevention, amelioration, or treatment of infectious or other types of disease. The immunogenic material may include attenuated or killed microorganisms (such as bacteria or viruses), or antigenic proteins, peptides, or DNA derived from them. A vaccine may include a disclosed immunogen, such as outer membrane microvesicles from PorA$^-$PorB$^-$ *Neisseria meningitidis*, such as a PorA$^-$PorB$^-$ RmpM$^-$ *Neisseria meningitidis*. Vaccines can elicit both prophylactic (preventative or protective) and therapeutic responses. Methods of administration vary according to the vaccine, but may include inoculation, ingestion, inhalation, or other forms of administration. Vaccines may be administered with an adjuvant to boost the immune response. In one specific, non-limiting example, a vaccine prevents and/or reduces the severity of the symptoms associated with hPIV infection and/or decreases the viral load compared to a control.

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

*Neisseria* Strains and Outer Membrane Microvesicles

In some embodiments, isolated PorA$^-$PorB$^-$RmpM$^-$ *N. meningitidis* are disclosed herein. These *N. meningitidis* are not naturally occurring, as PorB$^-$ *N. meningitidis* do not occur in nature. Isolated PorA$^-$PorB$^-$ *N. meningitidis*, such as isolated PorA$^-$PorB$^-$RmpM$^-$ *Neisseria meningitidis*, are of use in the disclosed methods.

Generally, PorA$^-$PorB$^-$RmpM$^-$ *N. meningitidis* are deficient from the production of PorA, PorB, and RmpM. Thus, these PorA, PorB, and RmpM subcapsular proteins cannot be detected in the surface of these *N. meningitidis*. Thus, PorA, PorB, and Rpm do not function in these *N. meningitidis*.

In some embodiments, there is a deletion in the PorA, PorB, and/or RmpM genes in these *N. meningitidis*, so that the corresponding protein is not produced. In other embodiments, there is a stop codon inserted in the PorA, PorB, and/or RmpM gene(s), so that the corresponding protein is not produced. In other embodiments, the genes include a mutation such that the protein is not functional or immunogenic, e.g., the protein not present on the outer membrane of the *N. meningitidis*.

In some embodiments, production of these surface proteins is decreased by at least 80%, 85%, 90%, 95%, 98%, 99% or is complete absent. Generally, in the strains of use in the methods disclosed herein, PorA, PorB, and RmpM is not detectable on the bacterial surface. Suitable methods for detecting PorA, PorB, and RmpM on the cell surface include whole cell ELISA using monoclonal and polyclonal protein-specific antibodies.

Modified strains can be generated by recombination techniques, and by non-recombinant techniques such as, for example, exposure to chemicals, radiation, or other DNA modifying or damaging agent, and the like. Modified strains having a desired protein expression profile, specifically wherein PorA, PorB, and/or RmpM is not detectable at the cell surface, can be identified through screening.

The *N. meningitidis* can be any type. *N. meningitidis* strains can be divided into serologic groups, serotypes, and subtypes on the basis of reactions with polyclonal (Frasch et al. (1985) *Rev Infect Dis* 7: 504-510, C. E. and Chapman, 1973, *J. Infect. Dis.* 127: 149-154) or monoclonal antibodies that interact with different surface antigens. Serogroup is based on immunologically detectable variations in the capsular polysaccharide. About 12 serogroups (A, B, C, X, Y, Z, 29-E, and W-135) are known. In some embodiments, the PorA$^-$PorB$^-$RmpM$^-$ *N. meningitidis* are serogroup A, B, or C.

*N. meningitidis* also can be divided into clonal groups or subgroups, using various techniques that directly or indirectly characterize the bacterial genome. These techniques include multilocus enzyme electrophoresis (MLEE), based on electrophoretic mobility variation of an enzyme, which reflects the underlying polymorphisms at a particular genetic locus. By characterizing the variants of a number of such proteins, genetic "distance" between two strains can be inferred from the proportion of mismatches. Similarly, clonality between two isolates can be inferred if the two have identical patterns of electrophoretic variants at a number of loci. Multilocus sequence typing (MLST) can also be used to characterize the microorganisms. Using MLST, the genetic distance between two isolates, or clonality, is inferred from the proportion of mismatches in the DNA sequences of 11 housekeeping genes in *N. meningitidis* strains (Maiden et al., 1998, *Proc. Natl. Acad. Sci. USA* 95:3140). Any strain can be selected and used to produce a PorA$^-$PorB$^-$ *N. meningitidis*, such as a PorA$^-$PorB$^-$RmpM$^-$ *N. meningitidis*.

Isolated *N. meningitidis* can be transformed to express a heterologous protein. These recombinant *N. meningitidis* are also of use in the methods disclosed herein, provided they are PorA$^-$PorB$^-$RmpM$^-$. The isolated *N. meningitidis* can be transformed to express additional antigens such as those exemplified in PCT Publication Nos. WO 99/24578, WO 99/36544; WO 99/57280, WO 00/22430, and WO 00/66791, as well as antigenic fragments of such proteins.

In some embodiments, outer membrane microvesicles are produced from PorA⁻PorB⁻ RmpM⁻ *N. meningitidis*. It is disclosed herein that an effective amount of microvesicles from a PorA⁻PorB⁻ *N. meningitidis*, such as an effective amount of microvesicles from a $PorA^-PorB^-$ $RmpM^-$ *N. meningitidis* can be used to induce an immune response to *Neisseria*, such as to *N. meningitidis* and/or *N. gonorrhoeae* Immunogenic compositions can be produced including an effective amount of microvesicles from a $PorA^-PorB^-$ $RmpM^-$ *N. meningitidis* and a pharmaceutically acceptable carrier. In some embodiments, outer membrane microvesicles from the $PorA^-PorB^-RmpM^-$ *N. meningitidis* that expresses a heterologous protein. These vesicles do not include the PorA, PorB, or RmpM, but include the heterologous protein.

The microvesicles can be outer membrane vesicles, blebs, or a combination thereof. Blebs are budded from living *N. meningitidis*. Methods for isolating blebs are also known in the art, see for example, Post et al., J. Biological Chem. 280: 38383-38394, 2005, incorporated herein by reference. OMV are produced by solubilizing *Neisseria*. Methods of producing OMV are disclosed, for example, in U.S. Published Patent Application No. 2012/0328643, incorporated herein by reference. Methods for the preparation of OMVs also are disclosed in Claassen et al. (*Vaccine* (1996) 14:1001-1008); Cartwright et al. (*Vaccine* (1999) 17:2612-2619); Peeters et al. (*Vaccine* (1996) 14:1009-1015); Fu et al. (*Biotechnology NY* (1995) 12:170-74); Davies et al. (*J. Immunol. Meth.* (1990) 134:215-225); Saunders et al. (*Infect. Immun.* (1999) 67:113-119); Draabick et al. (*Vaccine* (2000) 18:160-172); Moreno et al. (*Infect. Immun.* (1985) 47:527-533); Milagres et al. (*Infect. Immun.* (1994) 62:4419-4424); Naess et al. (*Infect. Immun.* (1998) 66:959-965]; Rosenqvist et al. [*Dev. Biol. Stand.* (1998) 92:323-333]; Haneberg et al. [*Infect. Immunn.* (1998) 66:1334-41); Andersen et al. (*Vaccine* (1997) 15:1225-34); and Bjune et al. (*Lancet* (1991) 338: 1093-96).

In some embodiments, OMVs are prepared by deoxycholate extraction. An extraction protocol is disclosed in Fredriksen et al., (1991) *NIPH Ann.* 14(2):67-79. Additional methods are disclosed, for example, in, Bjune et al. (*Lancet* (1991) 338(8775):1093-96), Fredriksen et al. (1991) *NIPH Annals* 14: 67-79, Pages 818-824 of *Pathobiology and immunobiology of Neisseriaceae* (eds. Conde-Glez et al.) ISBN 968-6502-13-0). The OMV (for example, as obtained by deoxycholate extraction) can be treated to remove certain components. For instance, pyrogens or toxic components may be removed (e.g. LOS).

Immunogenic Compositions and Methods of Use

Immunogenic Compositions of use in the disclosed method include outer membrane microvesicles from $PorA^-$ $PorB^-$ *N. meningitidis*, such as $PorA^-PorB^-RmpM^-$ *N. meningitidis*. The microvesicles can be OMV and/or blebs. The immunogenic compositions of use in the disclosed methods can include a mixture of microvesicles (e.g., OMV and blebs), which microvesicles can be from the same or different strains. In another embodiment, the immunogenic compositions can comprise a mixture of vesicles from 2, 3, 4, 5 or more $PorA^-PorB^-$ *N. meningitidis* strains, such as $PorA^-PorB^-RmpM^-$ strains, where the vesicles can be OMV, blebs or both.

Optionally, an immunogenic composition can include an adjuvant. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity Immunostimulatory oligonucleotides (such as those including a CpG motif) can also be used as adjuvants (for example, see U.S. Pat. Nos. 6,194,388; 6,207, 646; 6,214,806; 6,218,371; 6,239,116; 6,339,068; 6,406, 705; and 6,429,199). Adjuvants also include biological molecules, such as costimulatory molecules. Exemplary biological adjuvants include interleukin (IL)-2, IL-12, RANTES, granulocyte macrophage colony stimulating factor (GM-CSF), tumor necrosis factor (TNF)-α, and interferon (IFN)-γ.

In one embodiment, the microvesicles, such as the OMV and/or blebs, can used with an aluminum hydroxide adjuvant. One protein:adjuvant ratio is 1:67 (wt/wt). However, other ratios can be used, such as 1:20, 1:30, 1:40, 1:50, 1:33, 1;60, 1:65, 1:70, 1:75, 1:80 or 1:85).

Additional adjuvants include Complete Freund's Adjuvant, Incomplete Freund's Adjuvant, Gerbu adjuvant (GMDP; C.C. Biotech Corp.), RIBI fowl adjuvant (MPL; RIBI Immunochemical Research, Inc.), potassium alum, aluminum phosphate, QS21 (Cambridge Biotech), Titer Max adjuvant (CytRx), and Quil A adjuvant. Exogenous lipopolysaccharide (LPS) can also be used as an adjuvant.

The immunogenic compositions also can also include other agents, such as binders. Binders include, but are not limited to, carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent. The compositions can also include gum arabic, syrup, lanolin, starch, etc., that forms a vehicle for delivery. Included are substances that, in the presence of sufficient liquid, impart to a composition the adhesive quality needed for the preparation of pills or tablets.

Exemplary "pharmaceutically acceptable carriers" include liquid carriers (such as water, saline, culture medium, aqueous dextrose, and glycols) and solid carriers (such as carbohydrates exemplified by starch, glucose, lactose, sucrose, and dextrans, anti-oxidants exemplified by ascorbic acid and glutathione, and hydrolyzed proteins). Exemplary diluents include water, physiological saline solution, human serum albumin, oils, polyethylene glycols, glycerine, propylene glycol, or other synthetic solvents. The compositions can also include antibacterial agents such as benzyl alcohol, antioxidants such as ascorbic acid or sodium bisulphite, chelating agents such as ethylene diamine-tetraacetic acid, buffers such as acetates, citrates or phosphates, and agents for adjusting the osmolarity, such as sodium chloride or dextrose.

In some embodiments, the immunogenic composition can be formulated for administration by injection via the intramuscular, intraperitoneal, intradermal, or subcutaneous routes; or via mucosal administration to the oral/alimentary, respiratory (e.g., intranasal administration), genitourinary tracts. Although the immunogenic composition can be administered as a single dose, components thereof can also be co-administered together at the same time or at different times. In addition to a single route of administration, two or more different routes of administration can be used.

Immunogenic compositions can be lyophilized or be in aqueous form, e.g., solutions or suspensions. Liquid formulations allow the compositions to be administered directly from their packaged form, without the need for reconstitution in an aqueous medium. Compositions can be presented in vials, or they can be presented in ready-filled syringes. The syringes can be supplied with or without needles. A syringe will include a single dose of the composition, whereas a vial can include a single dose or multiple doses (e.g. 2, 3, 4, 5, 6, 7, 8, 9, or 10 doses). In one embodiment, the dose is for use in a human. In a further embodiment, the dose is for an adult, adolescent, toddler, infant, or less than one year old human, and can be administered by injection. Kits can include a measured dose for administration to a subject.

An immunogenic composition can be lyophilized. When an immunogenic composition requires reconstitution, it can be provided in the form of a kit which can comprise two vials, or can comprise one ready-filled syringe and one vial, with the contents of the syringe being used to reconstitute the contents of the vial prior to injection.

The OMVs can be used in conjunction with other agents, such as another vaccine or therapeutic agent. In some embodiments, the vaccine can be a meningococcal vaccine, such as a conjugate vaccine or a polysaccharide vaccine. In specific non-limiting examples, the vaccine is MPSV4 (MENOMUNE®), MCV4 (MENACTRA®, MENHIBRIX®, MENVEO®) or a serogroup B meningococcal vaccine (TRUMENBA® and BEXSERO®). Additional vaccines are MENCEVAX®, a purified polysaccharide vaccine, such as NmVac4-A/C/Y/W-135, and NIMENTRIX®.

Methods are disclosed herein for inducing an immune response to *Neisseria* in a mammalian subject using any of the disclosed immunogenic compositions including an effective amount of outer membrane microvesicles (for example, OMV and/or blebs) from PorA$^-$PorB$^-$ *N. meningitidis*, such as a PorA$^-$PorB$^-$rmpM$^-$ *N. meningitidis*. The immune response can be a protective immune response or a therapeutic immune response. The subject can be a human or veterinary subject. The subject can be an adult or a juvenile subject. In some embodiments, the subject is a human of two weeks, one month, 2, 3, 4, 5, 6, 7, 8, 9, 10, or 11 months, or one year or 15, 18, or 21 months of age, or a child of 2, 3, 4, 5, 6, 7, 8, 9, 10, 11, 12, or 13 years of age. The subject can be an adult, such as a human subject 18 or more years of age. The method can include administering 1, 2, 3, 4, 5, 6, 7, 8, 9 or 10 doses of an effective amount of outer membrane microvesicles (for example, OMV and/or blebs) from $PorA^-PorB^-$ *N. meningitidis*, such as a $PorA^-PorB^-RmpM^-$ *N. meningitidis*. In some embodiments, a single dose is used. In other embodiments, multiple doses are used, such as in a prime boost protocol. Exemplary non-limiting protocols are shown in the examples section. An initial dose and an additional dose can be administered within days, weeks, or months of each other.

In some embodiments, the subject has a *N. meningitidis* infection, and administration of the immunogenic composition increases clearance of the *N. meningitidis*. The *N. meningitidis* in the immunogenic composition can be any serogroup, such as serogroup A, B, or C. The *N. meningitidis* infection can be of any serogroup, such as serogroup A, B, and C. Optionally, the *N. meningitidis* in the immunogenic composition and the *N. meningitidis* infection are the same serogroup.

In other embodiments, the subject has a *N. gonorrhoeae* infection, and administration of the immunogenic composition increases clearance of the *N. gonorrhoeae*. In further embodiments, the subject is a healthy subject, and does not have a *N. meningitidis* or a *N. gonorrhoeae* infection. In some embodiments, methods are provided for inducing an immune response to *N. gonorrhoeae* in a mammalian subject, comprising administering to the mammalian subject an immunogenic composition comprising an effective amount of outer membrane microvesicles, such as blebs and/or OMVs, from $PorA^-PorB^-$ *N. meningitidis* and a pharmaceutically acceptable carrier. The $PorA^-PorB^-$ *N. meningitidis* can be $RmpM^-$. The *N. meningitidis* can be serogroup A, B or C, or any other serogroup (W, Y, etc.). The *N. gonorrhoeae* can be of any serotype.

The methods of the invention provide for administration of one or more antigenic compositions to a mammalian subject (e.g., a human) to elicit an immune response. The immune response can be against more than one strain of *Neisseria* species bacteria, and thus protection against disease caused by such bacteria. The disclosed methods can provide for an immunoprotective immune response against a 1, 2, 3, 4, 5 or more strains of *N. meningitidis* species, where the strains differ in at least one of serogroup, serotype, or serosubtype. See U.S. Published Patent Application No. US 20170065699, incorporated herein by reference, which discloses methods for immunizing against multiple strains, such as 2, 3, 4, 5, or more strains.

Optionally, the immunogenic composition can include an adjuvant. Suitable adjuvants are disclosed above.

The immunogenic composition can be administered by any route. This includes via injection for the intramuscular, intraperitoneal, intradermal, or subcutaneous routes; or via mucosal administration to the oral/alimentary, respiratory (e.g., intranasal administration), genitourinary tracts. Although the immunogenic composition can be administered as a single dose, additional doses can be co-administered together at the same time or at different times. In addition to a single route of administration, two or more different routes of administration can be used.

Administration can be accomplished by single or multiple doses. The dose administered to a subject in the context of the present disclosure should be sufficient to induce a beneficial therapeutic response in a subject over time, or to inhibit or prevent infection. The dose required will vary from subject to subject depending on the species, age, weight, and general condition of the subject, the severity of the infection being treated, the particular composition being used, and its mode of administration. An appropriate dose can be determined by one of ordinary skill in the art using only routine experimentation.

In some embodiments, an immunogenic composition can be administered orally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions are described in such publications as Remington's Pharmaceutical Science, 15th ed., Mack Publishing Company, Easton, Pa. (1980).

For oral administration, the compositions may need to be protected from digestion. This is typically accomplished either by association of the composition with an agent that renders it resistant to acidic and enzymatic hydrolysis or by packaging the composition in an appropriately resistant carrier. Means of protecting from digestion are well known in the art.

The immunogenic compositions are administered to an animal that has or is at risk for acquiring a *Neisseria* infection, to prevent or at least partially arrest the development of disease and its complications. An amount adequate to accomplish this is defined as an "effective dose" or an "immunogenically effective amount." Amounts effective for use will depend on, e.g., the antigenic composition, the manner of administration, the weight and general state of health of the subject, and the judgment of the prescribing physician. Single or multiple doses of the antigenic compositions may be administered depending on the dosage and frequency required and tolerated by the patient, and route of administration. A prime boost strategy can be utilized.

The amount of outer membrane microvesicles included in the immunogenic composition is sufficient to elicit an immune response, such as a humoral immune response and/or a cellular immune response, in the subject. Amounts for the immunization of the mixture generally range from about 0.001 mg to about 1.0 mg per 70 kilogram patient, more commonly from about 0.001 mg to about 0.2 mg per 70 kilogram patient. Dosages from 0.001 up to about 10 mg per patient per day may be used, particularly when the antigen is administered to a secluded site and not into the bloodstream, such as into a body cavity or into a lumen of an organ. Substantially higher dosages (e.g. 10 to 100 mg or more) are possible in oral, nasal, or topical administration. The initial administration of the mixture can be followed by booster immunization of the same of different mixture, with at least one booster, such as two boosters.

In some embodiments, administration is initiated prior to the first sign of disease symptoms, or at the first sign of possible or actual exposure to pathogenic *Neisseria*. Without being bound by theory, immunoprotective antibodies for *N. meningitidis* and/or *N. gonorrhoeae* can be generated by immunization with an immunogenic composition.

Immunoprotective antibodies for *N. meningitidis* and/or *N. gonorrhoeae* can be administered to an individual (e.g., a human patient) to provide for passive immunity, either to prevent infection or disease from occurring, or as a therapy to improve the clinical outcome in patients with established disease (e.g. decreased complication rate such as shock, decreased mortality rate, or decreased morbidity, such as deafness). Antibodies administered to a subject that is of a species other than the species in which they are raised are often immunogenic. Thus, for example, murine or porcine antibodies administered to a human often induce an immunologic response against the antibody. The immunogenic properties of the antibody are reduced by altering portions, or all, of the antibody into characteristically human sequences thereby producing chimeric or human antibodies, respectively.

Chimeric antibodies are immunoglobulin molecules comprising a human and non-human portion. More specifically, the antigen combining region (or variable region) of a humanized chimeric antibody is derived from a non-human source (e.g. murine), and the constant region of the chimeric antibody (which confers biological effector function to the immunoglobulin) is derived from a human source. The chimeric antibody should have the antigen binding specificity of the non-human antibody molecule and the effector function conferred by the human antibody molecule. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431 and 4,975,369). An alternative approach is the generation of humanized antibodies by linking the CDR regions of non-human antibodies to human constant regions by recombinant DNA techniques. See Queen et al., *Proc. Natl. Acad. Sci. USA* 86: 10029-10033 (1989) and WO 90/07861.

Fully human antibodies are also of use. Human antibodies consist entirely of characteristically human polypeptide sequences. The human antibodies of this invention can be produced by a wide variety of methods (see, e.g., Larrick et al., U.S. Pat. No. 5,001,065). In one embodiment, the human antibodies of the present invention are produced initially in trioma cells (descended from three cells, two human and one mouse). Genes encoding the antibodies are then cloned and expressed in other cells, particularly non-human mammalian cells. The general approach for producing human antibodies by trioma technology has been described by Ostberg et al. (1983), *Hybridoma* 2: 361-367, Ostberg, U.S. Pat. No. 4,634,664, and Engelman et al., U.S. Pat. No. 4,634,666. Triomas have been found to produce antibody more stably than ordinary hybridomas made from human cells.

Methods for producing and formulating antibodies suitable for administration to a subject (e.g., a human subject) are well known in the art. For example, antibodies can be provided in a pharmaceutical composition comprising an effective amount of an antibody and a pharmaceutical excipient (e.g., saline). The pharmaceutical composition may optionally include other additives (e.g., buffers, stabilizers, preservatives, and the like). An effective amount of antibody is generally an amount effective to provide for protection against Neisserial disease or symptoms for a desired period, e.g., a period of at least about 2 days to 10 days or 1 month to 2 months).

Chimeric Recombinant PorB

Chimeric recombinant PorB polypeptides are shown in FIGS. 11A-11B and SEQ ID NOs; 39-51. These PorB sequences are not naturally occurring. These chimeric recombinant PorB polypeptide can be included in a *Neisseria*. A *Neisseria* strain expressing the chimeric recombinant PorB is PorB$^+$. Polypeptides can be produced that are at least 95%, 96%, 97%, 98% or 99% identical to these proteins.

Nucleic acid molecules, such as DNA and RNA, can be produced encoding these chimeric recombinant PorB polypeptides. These polynucleotides include DNA, cDNA, and RNA sequences which encode the polypeptide of interest. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, Biochemistry, 3.sup.rd Edition, W.H. 5 Freeman and Co., NY). Nucleic acid molecules can readily be produced by one of skill in the art, using the amino acid sequences provided herein, and the genetic code.

A nucleic acid molecule can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, N Y, 1989).

A nucleic acid sequence that encodes a chimeric recombinant PorB polypeptide can be incorporated into a vector capable of expression in a host cell, using established molecular biology procedures. For example nucleic acids, such as cDNAs, that encode the chimeric recombinant PorB polypeptide can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR or other in vitro amplification.

Exemplary procedures sufficient to guide one of ordinary skill in the art through the production of vector capable of expression in a host cell (such as an adenoviral vector) that includes a polynucleotide sequence that encodes a chimeric recombinant PorB polypeptide can be found for example in Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2003); and Ausubel et al., *Short Protocols in Molecular Biology: A Compendium of Methods from Current Protocols in Molecular Biology*, 4th ed., Wiley & Sons, 1999.

Typically, a polynucleotide sequence encoding a chimeric recombinant PorB polypeptide is operably linked to transcriptional control sequences including, for example a promoter. A promoter is a polynucleotide sequence recognized by the transcriptional machinery of the host cell (or introduced synthetic machinery) that is involved in the initiation of transcription.

Exemplary promoters include viral promoters, such as cytomegalovirus immediate early gene promoter ("CMV"), herpes simplex virus thymidine kinase ("tk"), SV40 early transcription unit, polyoma, retroviruses, papilloma virus, hepatitis B virus, and human and simian immunodeficiency viruses. Other promoters are isolated from mammalian genes, including the immunoglobulin heavy chain, immunoglobulin light chain, T-cell receptor, HLA DQ α and DQ β, β-interferon, interleukin-2, interleukin-2 receptor, MHC class II, HLA-DRα, β-actin, muscle creatine kinase, prealbumin (transthyretin), elastase I, metallothionein, collagenase, albumin, fetoprotein, β-globin, c-fos, c-HA-ras, insulin, neural cell adhesion molecule (NCAM), α1-antitrypsin, H2B (TH2B) histone, type I collagen, glucose-regulated proteins (GRP94 and GRP78), rat growth hormone, human serum amyloid A (SAA), troponin I (TNI), platelet-derived growth factor, and dystrophin, and promoters specific for keratinocytes, and epithelial cells.

The promoter can be either inducible or constitutive. An inducible promoter is a promoter which is inactive or exhibits low activity except in the presence of an inducer substance. Examples of inducible promoters include, but are not limited to, MT II, MMTV, collagenase, stromelysin, SV40, murine MX gene, α-2-macroglobulin, MHC class I gene h-2 kb, HSP70, proliferin, tumor necrosis factor, or thyroid stimulating hormone gene promoter.

Typically, the promoter is a constitutive promoter that results in high levels of transcription upon introduction into a host cell in the absence of additional factors. Optionally, the transcription control sequences include one or more enhancer elements, which are binding recognition sites for one or more transcription factors that increase transcription above that observed for the minimal promoter alone.

It may be desirable to include a polyadenylation signal to effect proper termination and polyadenylation of the gene transcript. Exemplary polyadenylation signals have been isolated from bovine growth hormone, SV40 and the herpes simplex virus thymidine kinase genes. Any of these or other polyadenylation signals can be utilized in the context of the adenovirus vectors described herein.

The polynucleotides encoding a chimeric recombinant PorB polypeptide include a recombinant DNA which is incorporated into a vector in an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

Viral vectors can also be prepared encoding the chimeric recombinant PorB polypeptide. A number of viral vectors have been constructed, including polyoma, SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,2217,879), alphaviruses (S. Schlesinger, 1993, Trends Biotechnol. 11:18-22; I. Frolov et al., 1996, Proc. Natl. Acad. Sci. USA 93:11371-11377) and retroviruses of avian (Brandyopadhyay et al., 1984, Mol. Cell Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.). Thus, in one embodiment, the polynucleotide encoding a chimeric recombinant PorB polypeptide is included in a viral vector. Suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus, yeast and the like.

The chimeric recombinant PorB polypeptide, or a polynucleotide encoding the chimeric recombinant PorB polypeptide, as disclosed herein can be formulated in a variety of ways. Pharmaceutical compositions can include the chimeric recombinant PorB polypeptide, and pharmaceutically acceptable carrier, and optionally an adjuvant. Pharmaceutically acceptable carriers and adjuvants are disclosed above and are of use with a disclosed chimeric recombinant PorB polypeptide, or a polynucleotide encoding the chimeric recombinant PorB polypeptide.

EXAMPLES

The porin protein PorB is the dominant outer membrane protein (OMP) on the meningococcal surface and has been proposed as a MenB vaccine candidate. Expressed in all known clinical isolates, it is believed to be essential for in vivo meningococcal survival and is not subject to phase variation (Abad et al. (2006) *Clin Vaccine Immunol* 13: 1087-1091). Both native and recombinant PorB elicit the production of bactericidal antibodies (Poolman et al. (1983) *Infect Immun* 40: 398-406, Wright et al. (2002) *Infect Immun* 70: 4028-4034), and PorB-specific antibodies are generated in response to immunization with *N. meningitidis* outer membrane vesicle (OMV) vaccines (Bash et al. (2000) *FEMS Immunol Med Microbiol* 29: 169-176, Marzoa et al. (2012) *Vaccine* 30: 2387-2395, Norheim et al. (2012) *Scand J. Immunol* 76: 99-107), highlighting the direct interaction of PorB with the host immune system.

PorB-induced antibody responses are directed against six variable surface-exposed loops that differ in sequence depending on serotype. Although *N. meningitidis* is naturally competent and porB genetic mosaicism provides evidence for horizontal genetic exchange and strong positive selection, the sequences of some PorB serotypes commonly associated with invasive disease are often conserved, calling into question the interaction of specific PorB loop sequences in immune engagement.

Example 1

Chimeric Recombinant PorB (rPorB) Proteins and Isogenic PorB-Expressing Strains

In this example, it was demonstrated that antibody binding to a PorB epitope can be altered by sequence mutations in non-epitope loops. Through the construction of chimeric PorB types (see FIGS. 11A-11B) and PorB molecular dynamics simulations, it was demonstrated that loops both adjacent and non-adjacent to the epitope loop can enhance or diminish antibody binding, a phenotype that correlates with serum bactericidal activity.

PorB can self-assemble into homotrimers and is known to interact with other OMPs to form larger protein complexes. A panel of selective OMP deletion mutant strains (FIG. 1) was engineered to analyze the impact of complex formation on PorB-specific antibody binding (FIG. 2). Deletion of PorA and RmpM resulted in decreased antibody binding to PorB and lower bactericidal titers in a PorB-dependent killing assay.

Example 2

Serum Bactericidal Assays

Z15 is a bactericidal mAb; serum bactericidal assays (SBAs) were performed to assess complement-mediated killing. Although titers were low, the only strains in the isogenic hybrid strains expressing chimeric PorB that were consistently killed were those that were bound by Z15 most efficiently in whole cell dot blot assays, namely the MC58 PorB-expressing strain and the two $L5_4$-$L6_4$ mutants, M(1-4)C(5-6)M(7-8) and M(1-4)B(5-6)M(7-8). Thus, decreases in mAb binding associated with changes to non-epitope sequences correlated with a reduction in antibody-dependent killing activity.

Example 3

OMV from PorA(−) Isogenic Strains with Various PorB

In the following tables, the immunizing antigen used to generate the immune sera is listed in the far left column and the strain that is being tested (killed) in the bactericidal assay is shown in the first row at the top of each column. The numbers are the reciprocal of the highest dilution that kills at least 50% of the bacteria. Hence, a higher number means that there is more potent killing i.e. a higher concentration of functional (protective) antibodies.

Table A below is from the experiments with OMV from PorA(−) isogenic strains (MC58 background) but with different PorB. The antisera generated killed all 4 wild type strains tested. The high titers against the MC58 strain for all can be explained because that strain is homologous to the parental strain from which the OMV were derived, except for expression of a heterologous PorB type and the lack of PorA expression. Overall, the greatest cross-protection is that induced by the OCh OMV (FIGS. 11A-11B) immunogen in which the PorB is a constructed chimeric PorB not found in nature that was not immunogenic.

TABLE A

| MC58ΔporA::porB OMV | MC58 WT | Cu385 WT | Ch501 WT | BB1350 WT |
|---|---|---|---|---|
| Mc58 PorB Rabbit 1 | 64 | 8 | 32 | 128 |
| Mc58 PorB Rabbit 2 | 512 | 4 | 32 | 16 |
| Bb1350 PorB Rabbit 1 | 256 | 16 | 16 | 16 |
| Bb1350 PorB Rabbit 2 | 256 | 16 | 16 | 512 |
| Ch501 PorB Rabbit 1 | 512 | 16 | 32 | 128 |
| Ch501PorB Rabbit 2 | 512 | 8 | 64 | 16 |
| Och PorB Rabbit 1 | 512 | 64 | 128 | 256 |
| Och PorB Rabbit 2 | 512 | 64 | 256 | 256 |
| Cu385 rabbit 1 | 1024 | 128 | 64 | 16 |
| Cu385 Rabbit 2 | 512 | 128 | 64 | 16 |

Table B is from Bash et al. FEMS Immunol Med Microbiol. 2000 November; 29(3):169-76) wherein the OMV are from wild type strains and the antisera tested against the same wild type strains (nomenclature following strain in top column shows serogroup (capsule); serotype (PorB); subserotype (PorA). The M1.2 strain is PorA and class 5 negative. Importantly H355 is a similar to MC58 and has the same PorA as Cu385. In this experiment, the Cu385 antisera has lowered bactericidal activity, but the H355 antisera is bactericidal—but only against the two strains sharing the same type of PorA. Table B illustrates the PorA specificity of immune responses to OMV containing PorA.

TABLE B

| OMV | Ch501 (B:4,15; nss) | Cu385 (B:4:P1.15) | M1.2 (B:4:P1-:P5-) | H355 (B:15:P1.15) |
|---|---|---|---|---|
| Ch501 Rabbit 1 | 6 to 12 | 12 to 48 | 6 to 12 | 6 to 12 |
| Ch501 Rabbit 2 | 12 to 48 | 12 to 48 | 12 to 48 | 6 to 12 |
| Ch501 Rabbit 3 | 12 to 48 | 12 to 48 | 12 to 48 | — |
| Cu385 Rabbit 1 | — | — | — | — |
| Cu385 Rabbit 2 | — | 6 to 12 | — | — |
| H355 Rabbit 1 | — | >48 | — | >48 |
| H355 Rabbit 2 | — | >48 | — | >48 |

Example 7

Single, Double, or Triple Deletions of the Genes Encoding the Outer Membrane Proteins PorA (ΔA), PorB (ΔB), and the OMP Stabilizing Protein RmpM (ΔR)

In this example, mutants were generated with single, double, or triple deletions of the genes encoding PorA (PorA⁻, or ΔA), PorB (PorB⁻, or ΔB), and the OMP stabilizing protein RmpM (RmpM⁻, or ΔR) in the MC58 background.

Figure 1A:
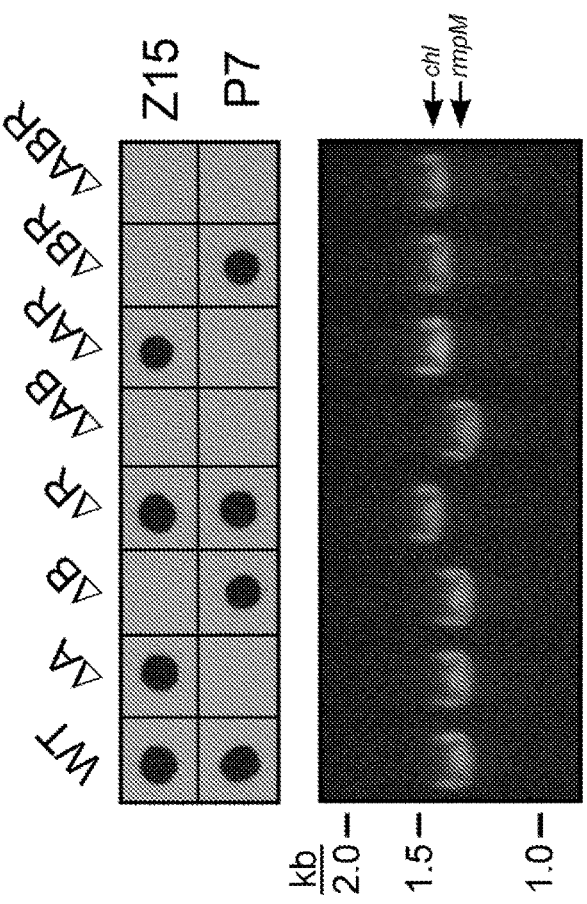
Figure 2B:
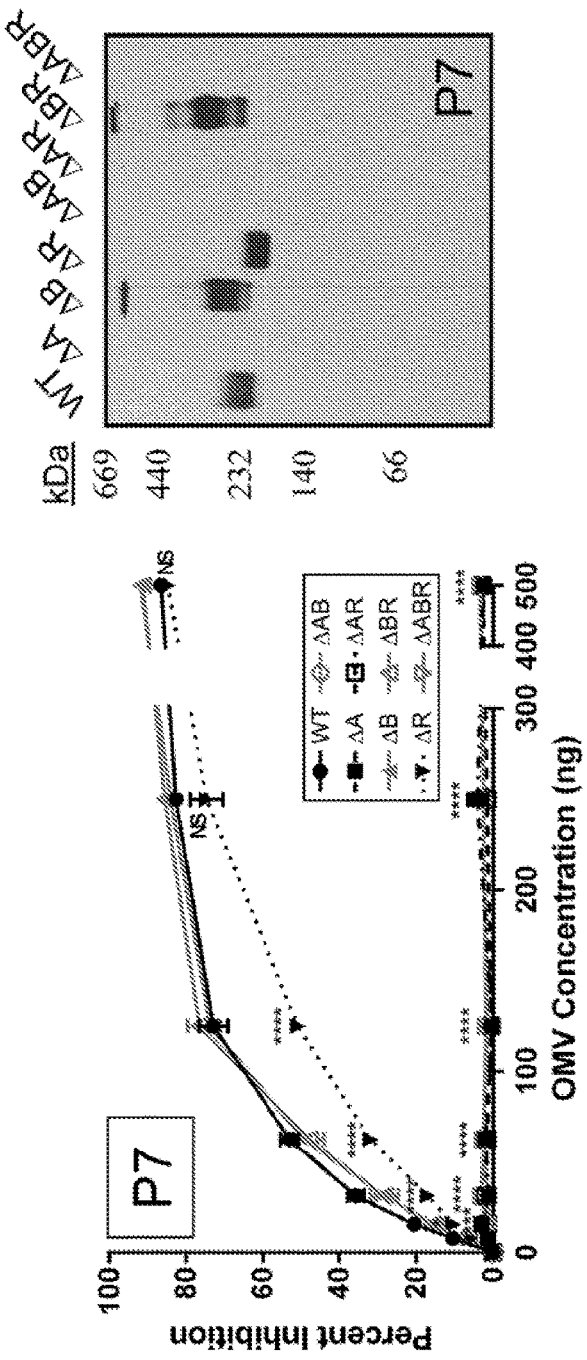

Development and Characterization: Because PorB is most often found in the context of a homotrimer or in association with PorA in heterotrimers (Sánchez et al. (2009) *Vaccine* 27: 5338-5343, Marzoa et al. (2009) *Proteomics* 9: 648-656), the possibility was explored that differences in the expression of PorB-interacting OMPs can alter the binding of PorB-specific antibodies. A series of mutants were generated with single, double, or triple deletions of the genes encoding PorA (ΔA), PorB (ΔB), and RmpM (ΔR) in the MC58 background. Proper deletion was confirmed by dot blot, PCR, and sequencing analyses (FIG. 1A). OMVs obtained from each of the strains exhibited no difference in size or purity when assessed by OptiPrep density centrifugation and transmission electron microscopy, though both the ΔAB and ΔABR OMVs and their respective strains expressed approximately ~2-fold less capsule relative to the other OMVs/strains when probed with anti-capsular SEAM12 in a dot blot. When analyzed via SDS-PAGE (FIG. 1B), there were no major differences in banding patterns observed, except for the expected loss of expression of PorA and PorB in the respective deletion strains and elevated PorA levels in ΔB and ΔBR, a phenomenon that has been previously described for the porB single mutant (Peak et al., 2015). Accordingly, ΔB exhibited an increase in porA transcript levels (fold change of 2.83±0.09 relative to WT) when examined by quantitative real time PCR (qPCR), though porB levels in ΔA were unaltered. Despite similar PorB and capsule expression, all of the PorA- and RmpM-deficient OMVs exhibited diminished binding profiles relative to the wild type (WT) when used to competitively inhibit Z15 binding to rMC58 (FIG. 2A, left panel), a phenotype consistent with lower bactericidal titers in a Z15-dependent SBA (Table 1). Binding of P7 to PorA was only decreased in ΔR compared to the other strains (FIG. 2B, left panel).

TABLE 1

Z15 PorB monoclonal antibody-dependent bactericidal activity of human sera against MC58 WT strain and isogenic OMP single, double, and triple deletion mutants. Titers are depicted as the reciprocal of the highest dilution resulting in >50% killing relative to heat-inactivated control wells lacking Z15. Results shown were the same for two independent assays.

| Strain | Titer |
|---|---|
| WT | >1024 |
| ΔA | 32 |
| ΔB | <4 |
| ΔR | 256 |
| ΔAB | <4 |
| ΔAR | 128 |
| ΔBR | <4 |
| ΔABR | <4 |

When the OMVs were fractionated by blue native gel electrophoresis (BNGE) and probed with the same antibodies to examine OMP complex formation, differences in banding patterns emerged. Whereas ΔA exhibited a phenotype similar to the WT after probing with Z15 (FIG. 2A, right panel) and ΔB adsorbed polyclonal sera MB1 and MB2, ΔR and ΔAR were characterized by only one large band that was of lower molecular weight (MW). This same band in ΔR also tested positive for the presence of PorA (FIG. 2B, right panel). When porB was deleted singly or in combination with rmpM, probing with P7 demonstrated the presence of one band that was roughly of the same MW found in the WT and three that were of higher MW (FIG. 2B, right panel). The largest of these (~700 kDa) has been confirmed previously as a high MW complex consisting of PorA by mass spectrometry (Marzoa et al. (2009) *Proteomics* 9: 648-656).

porA, porB, and rmpM gene knockouts: The differences observed via immunoblot suggested that OMP deletion led to formation of atypical PorA- and PorB-containing complexes. To assess their composition, BNGE was performed on OMVs. Post-staining with COOMASSIE® R-250 revealed the same dominant bands observed in the western blot (FIG. 2C, upper panel), though multiple higher and lower MW bands were visible by silver stain (FIG. 2D, lower panel). The dominant bands were cut out and in-gel digestion performed, followed by mass spectrometry for identification. Analysis of the recovered peptides revealed the absence of PorA, PorB, and RmpM in the complexes of the respective knockout strains and the presence of multiple proteins that were not detected in the WT complexes, including those involved in protein refolding (GroEL and DsbD), amino acid synthesis (IlvC), glycolysis (GapA, AceE), and electron transport chain-dependent metabolism (FixN, NqrA) (Table 2). In addition to expressing many of these same proteins, the probable TonB-dependent receptor TdfH was also found in the dominant complexes of the ΔBR and ΔABR strains, suggesting that deletion of PorB and RmpM in tandem diminishes nutrient acquisition and can lead to alterations in meningococcal gene expression and metabolism. Viability assays were used to support this study, which showed decreased growth for the strains relative to the WT over a time course of 8 h (FIG. 3A), including a significant reduction in the number of colony forming units (CFUs) (FIG. 3B) and production of smaller colonies as assessed by growth on BHI solid medium (FIG. 3C). While the ΔB and the ΔAB mutants were also characterized by a small colony phenotype (FIG. 3C), this effect was heterogeneous and maintained over repeated culturing, suggesting the presence of a non-PorA-specific protein that could compensate for small colony morphology in the presence of RmpM.

TABLE 2

List of proteins identified from dominant complexes of OMP deletion mutant OMVs. OMVs were fractionated via blue native gel electrophoresis, visualized with Coomassie staining, and cut out from the gel. Following SDS removal and trypsinization, peptides were extracted from the gel fragments and identified using reverse phase one-dimensional liquid chromatography mass spectrometry (1D LC-MS/MS). The complex from which each protein is derived is noted and corresponds to the bands observed in FIG. 2C. Proteins listed in bold indicate those not identified in WT complexes. Uniprot Accession numbers are provided and are incorporated by reference as available on Jul. 21, 2017.

| Strain | Components | Function | UnitProt ID | Complex |
|---|---|---|---|---|
| WT | PorB | Class 3 OMP; porin | Q6LD38 | 1, 2 |
|  | PorA | Class 1 OMP; porin | P0DH58 | 1, 2 |
|  | RmpM | Class 4 OMP; membrane integrity protein | P0A0V3 | 1, 2 |
|  | Opa | Opacity protein | O30755 | 1, 2 |
|  | Opc | Class 5 OMP; adhesin | Q9AE79 | 1, 2 |
|  | NMB0378 | Inorganic phosphate transporter | Q7DDQ8 | 1, 2 |
|  | MtrE | Multidrug efflux pump channel protein | Q9JY68 | 1 |
|  | TbpA | Transferrin-binding protein | Q9JPJ0 | 1, 2 |
|  | NMA1697 | Probable lipoprotein | A0A0H5QU | 1, 2 |
|  | LpdA2 | Dihydrolipoyl dehydrogenase | W8 | 1, 2 |
|  | LptD | LPS-assembly protein | Q9JZ09 | 1, 2 |
|  | NMB1964 | Uncharacterized protein | Q9K187 | 1 |
|  | AniA | Copper-containing nitrite reductase | Q7DD60 | 1, 2 |
|  | NorB | Nitric oxide reductase | Q9JYE1 | 1 |
|  | Pnp | Polyribonucleotide nucleotidyltransferase | Q9JYE2 | 1, 2 |
|  | PetB | Cytochrome b | Q9K062 | 2 |
|  | PetC | Ubiquinol--cytochrome c reductase, cytochrome c1 | Q9JXH0 | 2 |
|  | NMB1805 | Cytochrome c4 | Q9JXH1 | 2 |
|  | NMB1677 | Cytochrome c5 | Q7DD79 | 1 |
|  | FixO | Cytochrome c oxidase subunit II | Q9JYA2 | 1, 2 |
|  | FixP | Cytochrome c oxidase subunit III | Q9JY59 | 2 |
|  |  |  | E1AA24 |  |
| ΔA | PorB | Class 3 OMP; porin | Q6LD38 | 3, 4 |
|  | RmpM | Class 4 OMP; membrane integrity protein | P0A0V3 | 3, 4 |
|  | Opa | Opacity protein | O30755 | 3, 4 |
|  | Opc | Class 5 OMP; adhesin | Q9AE79 | 3, 4 |
|  | TbpA | Transferrin-binding protein | Q9JPJ0 | 3, 4 |
|  | NMA1697 | Probable lipoprotein | A0A0H5QU | 4 |
|  | LpdA2 | Dihydrolipoyl dehydrogenase | W8 | 3, 4 |
|  | LptD | LPS-assembly protein | Q9JZ09 | 4 |
|  | AniA | Copper-containing nitrite reductase | Q9K187 | 3, 4 |
|  | NorB | Nitric oxide reductase | Q9JYE1 | 4 |
|  | Pnp | Polyribonucleotide nucleotidyltransferase | Q9JYE2 | 3, 4 |
|  | PetC | Ubiquinol--cytochrome c reductase, cytochrome c1 | Q9K062 | 3, 4 |
|  | NMB1805 | Cytochrome c4 | Q9JXH1 | 3, 4 |
|  | FixO | Cytochrome c oxidase subunit II | Q7DD79 | 3, 4 |
|  | FixP | Cytochrome c oxidase subunit III | Q9JY59 | 3, 4 |
|  | GroEL | 60 kDa chaperonin | E1AA24 | 3 |
|  | GapA | Glyceraldehyde-3-phosphate dehydrogenase | X5EPF8 | 3 |
|  | DsbD | Thiol:disulfide interchange protein | C6SEX6 | 4 |
|  |  |  | Q9JYM0 |  |
| ΔB | PorA | Class 1 OMP; porin | P0DH58 | 5, 6 |
|  | RmpM | Class 4 OMP; membrane integrity protein | P0A0V3 | 5 |
|  | Opa | Opacity protein | O30755 | 5, 6 |
|  | NMB0378 | Inorganic phosphate transporter | Q7DDQ8 | 6 |
|  | MtrE | Multidrug efflux pump channel protein | Q9JY68 | 5 |
|  | TbpA | Transferrin-binding protein | Q9JPJ0 | 5 |
|  | LpdA2 | Dihydrolipoyl dehydrogenase | Q9JZ09 | 5 |
|  | LptD | LPS-assembly protein | Q9K187 | 5, 6 |
|  | NMB1964 | Uncharacterized protein | Q7DD60 | 5 |
|  | AniA | Copper-containing nitrite reductase | Q9JYE1 | 5, 6 |
|  | Pnp | Polyribonucleotide nucleotidyltransferase | Q9K062 | 5, 6 |
|  | PetC | Ubiquinol--cytochrome c reductase, cytochrome c1 | Q9JXH1 | 6 |
|  | NMB1805 | Cytochrome c4 | Q7DD79 | 6 |
|  | FixN | Cytochrome c oxidase subunit I | Q7DD90 | 6 |
|  | FixO | Cytochrome c oxidase subunit II | Q9JY59 | 5, 6 |
|  | DsbD | Thiol:disulfide interchange protein | Q9JYM0 | 5 |
| ΔR | PorB | Class 3 OMP; porin | Q6LD38 | 7 |
|  | PorA | Class 1 OMP; porin | P0DH58 | 7 |
|  | Opa | Opacity protein | O30755 | 7 |
|  | Opc | Class 5 OMP; adhesin | Q9AE79 | 7 |
|  | PilE | Fimbrial (pilin) protein | P05431 | 7 |
|  | TbpA | Transferrin-binding protein | Q9JPJ0 | 7 |
|  | NMA1697 | Probable lipoprotein | A0A0H5QU | 7 |
|  | LptD | LPS-assembly protein | W8 | 7 |
|  | AniA | Copper-containing nitrite reductase | Q9K187 | 7 |

TABLE 2-continued

List of proteins identified from dominant complexes of OMP deletion mutant OMVs.
OMVs were fractionated via blue native gel electrophoresis, visualized with Coomassie
staining, and cut out from the gel. Following SDS removal and trypsinization, peptides
were extracted from the gel fragments and identified using reverse phase one-dimensional
liquid chromatography mass spectrometry (1D LC-MS/MS). The complex from which each protein
is derived is noted and corresponds to the bands observed in FIG. 2C. Proteins listed in
bold indicate those not identified in WT complexes. Uniprot Accession numbers are provided
and are incorporated by reference as available on Jul. 21, 2017.

| Strain | Components | Function | UnitProt ID | Complex |
|---|---|---|---|---|
| | AceE | Pyruvate dehydrogenase subunit E1 | Q9JYE1 | 7 |
| | SucB | Dihydrolipoyllysine-residue succinyltransferase component of 2-oxoglutarate dehydrogenase complex | Q9JZ12 Q9JZP6 | 7 |
| | NMB1677 | | | 7 |
| | FixN | Cytochrome c5 | Q9JYA2 | 7 |
| | FixO | Cytochrome c oxidase subunit I | Q7DD90 | 7 |
| | FixP | Cytochrome c oxidase subunit II | Q9JY59 | 7 |
| | NqrA | Cytochrome c oxidase subunit III | E1AA24 | 7 |
| | GroEL | Na(+)-translocating NADH-quinone reductase subunit A | Q9K0M3 | 7 |
| | Fhs | 60 kDa chaperonin | X5EPF8 | 7 |
| | | Formate--tetrahydrofolate ligase | Q9JXY2 | |
| ΔAB | Opa | Opacity protein | O30755 | 8 |
| | NMB0378 | Inorganic phosphate transporter | Q7DDQ8 | 8 |
| | TbpA | Transferrin-binding protein | Q9JPJ0 | 8 |
| | AniA | Copper-containing nitrite reductase | Q9JYE1 | 8 |
| | PetC | Ubiquinol-cytochrome c reductase, cytochrome c1 | Q9JXH1 | 8 |
| | NMB1805 | Cytochrome c4 | Q7DD79 | 8 |
| | FixN | Cytochrome c oxidase subunit I | Q7DD90 | 8 |
| | FixO | Cytochrome c oxidase subunit II | Q9JY59 | 8 |
| AAR | TbpA | Transferrin-binding protein | Q9JPJ0 | 9 |
| | AniA | Copper-containing nitrite reductase | Q9JYE1 | 9 |
| | FixO | Cytochrome c oxidase subunit II | Q9JY59 | 9 |
| ABR | PorA | Class 1 OMP; porin | P0DH58 | 10 |
| | Opa | Opacity protein | O30755 | 10, 11 |
| | NMB0378 | Inorganic phosphate transporter | Q7DDQ8 | 11 |
| | MtrE | Multidrug efflux pump channel protein | Q9JY68 | 10 |
| | NMA1697 | Probable lipoprotein | A0A0H5QU W8 | 11 |
| | LpdA2 | Dihydrolipoyl dehydrogenase | | 10, 11 |
| | LptD | LPS-assembly protein | Q9JZ09 | 11 |
| | TdfH | Probable TonB-dependent receptor | Q9K187 | 11 |
| | AniA | Copper-containing nitrite reductase | Q7DDB6 | 10, 11 |
| | Pnp | Polyribonucleotide nucleotidyltransferase | Q9JYE1 | 10, 11 |
| | AceE | Pyruvate dehydrogenase subunit E1 | Q9K062 | 11 |
| | PetB | Cytochrome b | Q9JZ12 | 11 |
| | PetC | Ubiquinol--cytochrome c reductase, cytochrome c1 | Q9JXH0 | 11 |
| | NMB1805 | Cytochrome c4 | Q9JXH1 | 11 |
| | FixN | Cytochrome c oxidase subunit I | Q7DD79 | 11 |
| | FixO | Cytochrome c oxidase subunit II | Q7DD90 | 11 |
| | FixP | Cytochrome c oxidase subunit III | Q9JY59 | 11 |
| | GroEL | 60 kDa chaperonin | E1AA24 | 11 |
| | GapA | Glyceraldehyde-3-phosphate dehydrogenase | X5EPF8 | 11 |
| | DsbD | Thiol:disulfide interchange protein | C6SEX6 | 11 |
| | Fhs | Formate--tetrahydrofolate ligase | Q9JYM0 Q9JXY2 | 11 |
| ΔABR | Opa | Opacity protein | O30755 | 12 |
| | NMB0378 | Inorganic phosphate transporter | Q7DDQ8 | 12 |
| | TbpA | Transferrin-binding protein | Q9JPJ0 | 12 |
| | LptD | LPS-assembly protein | Q9K187 | 12 |
| | TdfH | Probable TonB-dependent receptor | Q7DDB6 | 12 |
| | AniA | Copper-containing nitrite reductase | Q9JYE1 | 12 |
| | PetC | Ubiquinol--cytochrome c reductase, cytochrome c1 | Q9JXH1 | 12 |
| | NMB1805 | Cytochrome c4 | Q7DD79 | 12 |
| | FixN | Cytochrome c oxidase subunit I | Q7DD90 | 12 |
| | FixO | Cytochrome c oxidase subunit II | Q9JY59 | 12 |
| | IlvC | Ketol-acid reductoisomerase | Q9JYI2 | 12 |

TABLE 3

Oligonucleotides used in this study.

| Primer Name | Sequence (5' → 3') | SEQ ID NO: | Description |
|---|---|---|---|
| *Strain construction: Immunizing OMV PorB antigens* | | | |
| porBNdeIF | GACT<u>CATATG</u>TTCAGACATGGAATCGCC | 1 | Forward primer, amplifies full porB ORF; contains NdeI restriction site. |
| porBBamHIR | ATAT<u>GGATCC</u>TTCAGACGGCGCATTTTTATG | 2 | Reverse primer, amplifies full porB ORF; contains BamHI restriction site and DUS. |
| *Strain construction: OMP deletion mutants* | | | |
| porBUPBamHIF | ATAT<u>GGATCC</u>TGCAATGCCCTCCAATAC | 3 | Forward primer, amplifies ~290 bp 5' MC58 porB upstream region; contains BamHI restriction site. |
| porBUPXbaIR | CGCG<u>TCTAGA</u>TGCTGTATTCCTTTTTTGGTTAA | 4 | Reverse primer, amplifies ~290 bp 5' MC58 porB upstream region; contains XbaI restriction site. |
| porBDOWNSphIF | ATAT<u>GCATGC</u>TCTGCAAAGATTGGTATCAACA | 5 | Forward primer, amplifies 310 bp 3' MC58 porB downstream region; contains SphI restriction site. |
| porBDOWNHindIIIR | ATATA<u>AGCTT</u>CAGACGGCTGAAACTCAACG | 6 | Reverse primer, amplifies 310 bp 3' MC58 porB downstream region; contains HindIII restriction site and DUS. |
| eryXbaIF | ATAT<u>TCTAGA</u>CACCATAGGCTTTAGAGAAGTATTTGAATGC | 7 | Forward primer, amplifies 1.1 kb ermB cassette; contains XbaI restriction site. |
| erySphIR | CCGA<u>GCATGC</u>TTATTATTATTTCCTCCCGTTAAATAATAG | 8 | Reverse primer, amplifies 1.1 kb ermB cassette; contains SphI restriction site. |
| porAUPBamHIF | ATAT<u>GGATCC</u>AAGCCGAGACTGCATC | 9 | Forward primer, amplifies ~260 bp 5' MC58 porA upstream region; contains BamHI restriction site. |
| porAUPXbaIR | CGCG<u>TCTAGA</u>ATCGGCTTCCTTTTGTAAAT | 10 | Reverse primer, amplifies ~260 bp 5' MC58 porA upstream region; contains XbaI restriction site. |
| porADOWNSphIF | ATAT<u>GCATGC</u>ATATCGGGGCGG | 11 | Forward primer, amplifies ~250 bp 3' MC58 porA downstream region; contains SphI restriction site. |
| porADOWNHindIIIR | ATATA<u>AGCTT</u>CAGACGGCGCATTTTTATGC | 12 | Reverse primer, amplifies ~250 bp 3' MC58 porA downstream region; contains HindIII restriction site and DUS. |
| kanXbaIF | ATAT<u>TCTAGA</u>GGGAAAGCCACTTTGTGTCTCA | 13 | Forward primer, amplifies ~950 bp aph3A cassette; contains XbaI restriction site. |

TABLE 3-continued

Oligonucleotides used in this study.

| Primer Name | Sequence (5' → 3') | SEQ ID NO: | Description |
|---|---|---|---|
| kanSphIR | GTATGCATGCTTATTATTAGAAAAACTCATCGAGCATC | 14 | Reverse primer, amplifies ~950 bp aph3A cassette; contains SphI restriction site. |
| rmpMUPBamHIF | TAGTGGATCCAATCGTGCGATATGGAA | 15 | Forward primer, amplifies ~250 bp 5' MC58 rmpM upstream region; contains BamHI restriction site. |
| rmpMUPXbaIR | CGCGTCTAGATTTATTCCCTCATTAAATTTGTACAGC | 16 | Reverse primer, amplifies ~250 bp 5' MC58 rmpM upstream region; contains XbaI restriction site. |
| rmpMDOWNSphIF | GTATGCATGCGGCTAGGCAATATCTTG | 17 | Forward primer, amplifies ~260 bp 3' MC58 rmpM downstream region; contains SphI restriction site. |
| rmpMDOWNHindIIIR | ATATAAGCTTCAGACGGCGTTAATCCACTATAAAGC | 18 | Reverse primer, amplifies ~260 bp 3' MC58 rmpM downstream region; contains HindIII restriction site and DUS. |
| chlXbaIF | GTATTCTAGACGCCGAATAAATACCTGTGACGG | 19 | Forward primer, amplifies ~870 bp cat cassette; contains XbaI restriction site. |
| chlSphIR | ATATGCATGCTTATTATTACGCCCCGCC | 20 | Reverse primer, amplifies ~870 bp cat cassette; contains SphI restriction site. |
| Strain construction: Hybrid PorB types* | | | |
| porBORFXbaIF | ATATTCTAGAATGAAAAAATCCCTGATTGCCCTGAC | 21 | Forward primer, porB amino acid position M1; contains XbaI restriction site. |
| porBF189R | GAAGAAGCCACCGTTTTTGTAGTTGAAGC | 22 | Reverse primer, porB amino acid position F189; contains 15 bp overlapping with porBN185F. |
| porBN185F | AACGGTGGCTTCTTCGTGCAATATG | 23 | Forward primer, porB amino acid position N185; contains 15 bp overlapping with porBF189R. |
| porBS267R | AGAAACTCGGGGCGTTACGTTG | 24 | Reverse primer, porB amino acid position S267; contains 15 bp overlapping with porBT263F. |
| porBT263F | ACGCCCCGAGTTTCTTACGC | 25 | Forward primer, porB amino acid position T263; contains 15 bp overlapping with porBS267R. |
| porBORFSphIR | ATATGCATGCTTAGAATTTGTGGCGCAG | 26 | Reverse primer, porB amino acid position F331; contains SphI restriction site. |

TABLE 3-continued

Oligonucleotides used in this study.

| Primer Name | Sequence (5' → 3') | SEQ ID NO: | Description |
|---|---|---|---|
| kanSphIF | ATATGCATGCGAAAGCCACTTTGTGTCT | 27 | Forward primer, used with kanSphIR to amplify ~950 bp aph3A cassette; contains SphI restriction site. |
| rPorB/rPorA synthesis | | | |
| porBNdeIF2 | ATATCATATGGACGTTACCCTGTACGGCA | 28 | Forward primer, amplifies porB ORF starting at amino acid D20; contains NdeI restriction site. |
| porBBlpIR | ATATGCTCAGCTTAGAATTTGTGGCGC | 29 | Reverse primer, amplifies porB ORF starting at amino acid D20; contains BlpI restriction site. |
| porANdeIF | ATATCATATGGATGTCAGCCTATACGGCGA | 30 | Forward primer, amplifies porA ORF starting at amino acid D20; contains NdeI restriction site. |
| porABlpIR | ATATCTCGAGGAATTTGTGGCGCAAAC | 31 | Forward primer, amplifies porA ORF starting at amino acid D20; contains BlpI restriction site. |
| qPCR analysis | | | |
| porAF | TGTCGGACGTAATGCTTTTG | 32 | Forward primer, amplifies 199 bp porA transcript. |
| porAR | GGCAATTTCGGTCGTACTGT | 33 | Reverse primer, amplifies 199 bp porA transcript. |
| porBF | CAATACGCGCTTAACGACAA | 34 | Forward primer, amplifies 200 bp porB transcript. |
| porBR | GAAGCGTACAGGGCATCATT | 35 | Reverse primer, amplifies 200 bp porB transcript. |
| 16SF | GCGCAACCCTTGTCATTAGT | 36 | Forward primer, amplifies 198 bp 16S rRNA transcript. |
| 16SR | CGGACTACGATCGGTTTTGT | 37 | Reverse primer, amplifies 198 bp 16S rRNA transcript. |

Restriction endonuclease sites and DNA uptake sequence (DUS) are depicted as underlined and in bold, respectively.
*Primer residues numbered relative to MC58 sequence.

Example 8

Materials and Methods for Examples 1-7

Bacterial growth conditions: N. meningitidis strains were routinely incubated overnight at 37 degrees Celsius in the presence of 5 percent $CO_2$ on BBL Brain Heart Infusion (BHI) Agar plates (Becton Dickinson, Sparks, Md.) supplemented with heat inactivated 5 percent HyClone Donor Equine Serum (ThermoFisher Scientific, Waltham, Mass.). For growth in culture, Bacto Tryptic Soy Broth (TSB) (Becton Dickinson) was used with shaking at 250 rpm. Escherichia coli strains were grown in Difco Luria Bertani Miller Broth or on LB Agar plates (Becton Dickinson). Antibiotics were added as needed at the following concentrations: N. meningitidis, erythromycin (3 microgram $ml^{-1}$), kanamycin (50 microgram $ml^{-1}$), chloramphenicol (5 microgram $ml^{-1}$); E. coli, erythromycin (300 microgram $ml^{-1}$), kanamycin (50 microgram $ml^{-1}$), chloramphenicol (50 microgram $ml^{-1}$), ampicillin (100 microgram $ml^{-1}$).

Construction of OMV antigens and rabbit immunizations: Primer pair porBNdeIF/porBBamHIR (Table 3) was used to amplify the porB gene of WT strains MC58, Cu385, BB1350, and Ch501; gene products were digested with NdeIF and BamHI and ligated into pUC18. Plasmids were verified by sequencing and transformed into MC58 porA::kan (generous gift of D. M. Granoff). Transformants were selected and PorB expression confirmed via dot blot with serotype 15 and 4 mAbs, Z15 (8B5-5-G9) and Z4 (5DC4C8G8) (National Institute for Biological Standards and Control (NIBSC), South Mimms, Hertfordshire, England).

During confirmatory meningococcal strain sequencing, it was discovered that transformation with pUC18-Cu385 had resulted in a crossover event in one of the isolates between the native MC58 gene and the Cu385 porB at the end of L1 (FIG. 4). This strain, designated MC58 porA::kan-OCh (also known as OCh), and the isogenic strains expressing the WT porB genes were incubated in TSB broth and detoxified OMVs were obtained as previously described by incubation in 5 percent deoxycholate (Bash et al. (2000) *FEMS Immunol Med Microbiol* 29: 169-176). Protein content and endotoxin levels were estimated using the Pierce BCA Protein Assay Kit (ThermoFisher) and LAL Chromogenic Endotoxin Quantitation Kit (ThermoFisher), respectively, according to the manufacturer's protocols.

Rabbits were immunized with an equivalent mixture of 25 micrograms OMVs/Imject Alum Adjuvant (ThermoFisher) via intramuscular injection of the hind limb. Two additional immunizations were administered at three-week intervals, and blood samples were collected one week prior to the first immunization and two weeks following the second and third immunization.

Generation of OMP deletion mutants: Primer pairs porBUPBamHIF/porBUPXbaIR, porAUPBamHIF/porAUPXbaIR, and rmpMUPBamHIF/rmpMUPXbaIR were used to PCR amplify the promoter region of porB, porA, and rmpM, respectively. Each product was digested with BamHI and XbaI and inserted into pGEM-3Z (PROMEGA™, Madison, Wis.). The downstream region of each gene was then amplified using porBDOWNSphIF/porBDOWNHindIIIR, porADOWNSphIF/porADOWNHindIIIR, and rmpMDOWNSphIF/rmpMDOWNHindIIIR; products were digested with SphI and HindIII and inserted into the gene-matched vector. The ermB, aph3A, and cat cassettes encoding resistance to erythromycin, kanamycin, and chloramphenicol, respectively, were amplified using eryXbaIF/erySphIR, kanXbaIF/kanSphIR, and chlXbaIF/chlSphIR. Digestion with XbaI/SphI and insertion into vectors resulted in formation of the plasmids pKAM53, pKAM60, and pKAM106. Plasmids were linearized and used to transform MenB strain MC58. Colonies were screened for double homologous recombination via growth on antibiotics and PCR. Deletion of PorB and PorA proteins was confirmed via dot blot with mAbs Z15 and P7 (MN14C11.6; NIBSC). Gene deletion was confirmed in all mutants via sequencing analysis.

Construction of hybrid PorB strains: To generate chimeric porB genes (FIGS. 11A-11B), a series of overlapping PCR amplifications was performed. For M(1-4)C(5-8) and M(1-4)B(5-8), primer pairs porBORFXbaIF/porBF189R and porBN185F/porBORFSphIR were used to amplify L1-L4 of MC58 porB and L5-L8 of Cu385/BB1350 porB, respectively; to generate M(1-6)C(7-8) and M(1-6)B(7-8), primer pairs porBORFXbaIF/porBS267R and porBT263F/porBORFSphIR were used to amplify the gene portions of the same strains. The products of each reaction were then gel purified and a second PCR amplification was conducted using the primer pair porBORFXbaIF/porBSphIR. The product of the overlapping PCR was digested with XbaI and SphI and inserted into pKAM53. Proper porB insertion and ermB removal were verified by assessing colonies for ampicillin resistance and erythromycin sensitivity.

For M(1-4)C(5-6)M(7-8) and M(1-4)B(5-6)M(7-8), the same procedure was used except that two overlapping PCR amplifications were performed. In the first, porBORFXbaIF/porBF189R was used to amplify MC58 L1-L4; L5-L6 of Cu385 or BB1350 was amplified with porBN185F/porB267R. Hybrid L1-L6 were joined together by amplification using porBORFXbaIF/porB267R. MC58 L7-L8 was then obtained by PCR with porBT263F/porBORFSphIR.

The final chimeric gene product was generated by PCR amplification using porBORFXbaIF/porBORFSphIR. Reciprocal mutant porB vectors (those bearing serotype 4 sequence in the 5' end of the gene) for all chimeric types were created using the same primer pairs described above, but the strains from which the porB loop sequences were amplified were switched. Vectors expressing the four WT PorB types and the OCh type were also amplified using the porBORFXbaIF/porBORFSphIR primer pair and template genomic DNA isolated from the immunizing strains.

Following insertion of the WT and chimeric porB genes into their respective vectors, the aph3A cassette was PCR amplified with kanSphIF/kanSphIR and was then digested with SphI and inserted into each plasmid. Plasmids were linearized and used to transform the OMP deletion strain ΔB. Isolates exhibiting an erythromycin-sensitive, kanamycin-resistant phenotype indicative of a double homologous recombination event were screened via PCR and dot blot for PorB expression.

Recombinant PorB and PorA synthesis: Primer pair porBNdeIF2/porBBlpIR was used to amplify each of the WT and chimeric PorB types from the pGEM-3Z-porB-kan plasmid constructs described in the section above. Each of the products were gel purified, digested with NdeI and BlpI, and inserted into pET-28a(+) (PROMEGA™). The rPorB vectors were then transformed into *E. coli* expression strain BL21(DE3) ΔompA, the construction of which was described previously (Qi et al. (1994) *Infect Immun* 62: 2432-2439). Following screening and sequencing, plasmid-bearing strains were induced for His-tagged rPorB expression with 0.5 mM isopropyl beta-D-1-thiogalactopyranoside (IPTG). Cultures were centrifuged, and the pellet was suspended in 1× BUGBUSTER®Protein Extraction Reagent (EMD Millipore, Temecula, Calif.) in Tris buffer (30 mM Tris, 300 mM sodium chloride, pH 8.0), supplemented with rLysozyme (EMD Millipore). Inclusion bodies were purified via centrifugation and lysed with 8 M urea in Tris buffer. Lysates were run through QIAGEN®Ni-NTA Superflow resin (Valencia, Calif.), and rPorB was refolded on the column with 0.1 percent ZWITTERGENT® 3-14 detergent in Tris buffer. Proteins were eluted with imidazole and dialyzed, and protein concentration was estimated by BCA. Recombinant PorA (serosubtype P1.7) was also produced from WT MC58 using the same method. porA amplification was achieved with primer pair porANdeIF/porABlpIR.

OMV purification: The OMP deletion mutant strains and those expressing the chimeric (hybrid) PorB types were grown in TSB for 6 h with shaking (130 rpm), at which time cells were used to inoculate a large batch TSB culture grown for 16 h with shaking. Bacteria were heat killed for 1 h at 65 degrees Celsius, centrifuged for 30 min at 50,000×g, and suspended in distilled water. The cells were then broken open via French press as previously described (Marzoa et al. (2009) *Proteomics* 9: 648-656). Large debris was removed with centrifugation at 10,000×g for 15 min, and the supernatant was ultracentrifuged at 40,000×g for 30 min to purify OMVs. OMVs were suspended at a concentration of 1 mg/ml in distilled water and stored at −80 degrees Celsius until further use. For animal immunizations, LOS-detoxified OMVs were obtained as previously described (Bash et al., 2000).

Immunoblots/dot blots: 500 ng of WT and chimeric (hybrid) rPorB were fractionated via SDS-PAGE and transferred to IBLOT™ nitrocellulose membranes (ThermoFisher). Alternatively, 20 micrograms of OMVs from the OMP deletion mutants were fractionated by blue native gel electrophoresis (BNGE) (Marzoa et al. (2009) *Proteomics* 9:

648-656), and OMP complexes were transferred to IBLOT™ polyvinylidene difluoride (PVDF) membranes (ThermoFisher). For dot blots, OMP deletion strains were grown on BHI plates overnight and suspended to an optical density of $OD_{600\ nm}$=1.0 in PBS. Following incubation for 1 h at 65 degrees Celsius to heat kill the bacteria, lysates were spotted in 5 microliter volumes onto nitrocellulose membranes. All membranes were blocked with 10 percent (%) skim milk and probed with mAbs or polyclonal antibody sera. Membranes were washed, incubated with appropriate secondary antibody (horseradish peroxidase (HRP)-conjugated goat anti-mouse or goat anti-rabbit IgG, Bio-Rad Laboratories, Hercules, Calif.), and developed with Pierce ECL Western Blotting Substrate (ThermoFisher).

Competitive ELISAs: For competitive ELISAs, Immulon 4 HBX plates (ThermoFisher) were coated with 500 ng of rPorB or rPorA in carbonate buffer (15 mM sodium carbonate, 35 mM sodium bicarbonate, pH 9.6) overnight at 4 degrees Celsius. Plates were washed in PBS TWEEN® (0.05 percent), blocked in one percent bovine serum albumin (BSA), and probed for binding with a mixture of either the Z15 PorB-specific or the P7 PorA-specific mAbs pre-incubated (overnight at 4 degrees Celsius) with increasing concentrations of OMVs (0-50 µg) Following overnight incubation at 4 degrees Celsius, plates were washed and incubated with HRP-conjugated goat anti-mouse antibody at 37 degrees Celsius for 2 h. Plates were developed with o-phenylenediamine dihydrochloride (Sigma Aldrich, St. Louis, Mo.) and read at 490 nm. Percent inhibition was determined by the calculation: ((optical density of sample– optical density of control)/optical density of control)*100, where control=binding of antibody to rPorB in the absence of OMVs.

Viability tests: OMP deletion strains were streaked from overnight growth on plates and suspended in TSB broth at a density of $OD_{600}$=0.1. Bacteria were grown with shaking (250 rpm) and were assessed every hour for $OD_{600}$ value for a period of 8 h. At t=0, 3, and 8 h, times corresponding with lag phase, log phase, and early stationary phase, respectively, aliquots were obtained and serially diluted to enumerate CFUs; samples were also obtained at 8 h to obtain mRNA (see below). Representative images of CFUs at t=8 h were obtained on an Olympus SZX16 stereomicroscope.

For examination of porA and porB transcripts by qPCR, mRNA was extracted from aliquots of the WT, ΔA, and ΔB bacterial strains using the TRIzol Max Bacterial RNA Isolation Kit (ThermoFisher) according to the manufacturer's protocol. The High Capacity cDNA Reverse Transcriptase Kit (ThermoFisher) was used to synthesize cDNA, and 50 ng of each sample was assayed using SYBR Green PCR MasterMix (ThermoFisher). Transcript levels were normalized to 16S rRNA (primers shown in the Table 3), and fold change was determined relative to WT using the ΔΔCt method (Livak and Schmittgen, 2001).

Serum bactericidal assay: The exogenous complement SBA assay was performed in 96-well plates as previously described (Bash et al. (2014) *Clin Vaccine Immunol* 21: 755-761) with slight modifications. Briefly, OMP deletion strains were incubated at 37 degrees Celsius with shaking (65 rpm) in the presence of 2-fold dilutions of Z15 mAb (in 0.5 percent BSA in Hank's Buffered Saline Solution) and pooled human sera that had been pre-screened for lack of endogenous killing activity. After 1 h, an overlay of TSB with 0.7 percent noble agar was added, and plates were incubated overnight. The following morning, CFUs were enumerated, and the SBA titer was recorded as the reciprocal of the highest dilution resulting in 50 percent killing relative to the average of the negative controls (bacteria that were incubated with heat inactivated sera in the absence of Z15).

Molecular dynamics simulations: The PorB trimer structure of wild type strain MC58 was taken from the crystal structure (PDB:3WI4), and a PorB trimer model for strain Cu385 was built by mutating the side chains of the MC58 PorB structure to the Cu385 sequence. Each protein was then embedded in asymmetric bilayers of L3 immunotype LOS in the outer leaflet and phospholipids in the inner leaflet, which mimics the *N. meningitidis* outer membrane. Building, assembly, and initial CHARMM-based equilibrations of these systems (MC58 and Cu385) were achieved by CHARMM-GUI based step-by-step protocol (Jo et al. (2008). *J Comput Chem* 29: 1859-1865, Wu et al. (2013) *Biophys J* 105: 1444-1455), Wu et al. (2014a) CHARMM-GUI *J Comput Chem* 35: 1997-2004, Wu et al. (2014b) *Biophys J* 106: 2493-2502., Patel et al. (2016) *Biophysical J* 110: 930-938). 450-ns NPT (constant particle number, pressure, and temperature) production runs were performed for both systems using NAMD (Phillips et al. (2005) *J Comput Chem* 26: 1781-1802) with a temperature of 310.15 K and a pressure of 1 bar. A 2-fs time-step together with the SHAKE algorithm (Ryckaert et al. (1977) *J Comput Phys* 23: 327-341) was used, and the van der Waals interactions were smoothly switched off at 10-12 Angstrom (Å) by a force-switching function (Steinbach and Brooks (1994) *J Comput Chem* 15: 667-683), while the long-range electrostatic interactions were calculated using the particle-mesh Ewald method (Essmann et al. (1995) *J Chem Phys* 103: 8577-8593). In NAMD production run, Langevin dynamics was used to maintain constant temperature with a Langevin coupling coefficient of 1 $ps^{-1}$, and a Nosé-Hoover Langevin piston (Feller et al. (1995) *J Chem Phys* 103: 4613-4621, Martyna et al., (1994) *J Chem Phys* 101: 4177-418) was used to maintain constant pressure with a piston period of 50 fs and a piston decay time of 25 fs. All the simulations were performed using C36 force field for lipids (Klauda et al. (2010) *J Phys Chem B* 114: 7830-7843), carbohydrates (Guvench et al. (2008) *J Comput Chem* 29: 2543-2564, Guvench et al. (2009) *J Chem Theory Comput* 5: 2353-2370, Guvench et al. (2011) *J Chem Theory Comput* 7: 3162-3180), and the TIP3P water model (Jorgensen et al. (1983) *J Chem Phys* 79: 926-935).

Mass spectrometry analysis: 20 micrograms of OMVs from OMP deletion strains were fractionated by BNGE and stained with COOMASSIE® R-250. Dominant bands were cut from the gel, and in-gel digestion was performed as previously described (Jensen et al. (1999) In: Methods in Molecular Biology. A. J. Link (ed). Totowa, N.J.: Humana Press, pp. 513-53). Briefly, SDS was removed from the gel pieces with sequential washes of acetonitrile and water, followed by drying in a speed vacuum. Samples were rehydrated with ammonium bicarbonate, reduced with 40 mM dithiothreitol, and alkylated with 100 mM iodoacetamide. After washing, peptides were digested overnight at room temperature with 150 ng trypsin and extracted from the gel pieces with formic acid.

Extracted peptides for each gel band were analyzed using reverse phase one-dimensional liquid chromatography mass spectrometry (1D LC-MS/MS) with an EASY NLC™II Proxeon nanoflow HPLC system that was coupled online to a Q-Exactive Orbitrap mass spectrometer (ThermoFisher). The survey scans were acquired in the Orbitrap analyzer at a resolution of 70.000, and the fragment ions were acquired with a resolution of 17.000. MS data files were searched against the UniProtKB/Swiss-Prot *N. meningitidis* database (2015) supplemented with the porcine trypsin sequence using the Mascot search engine (Matrix Sciences; version 2.4.0). The Mascot output files were analyzed using the software Scaffold 4.2.0 (Proteome Software Inc.). Protein identifications were accepted if they could be established at greater than a 99.9 percent probability and contained at least 2 identified peptides (Table 2). Protein probabilities were assigned by the Protein Prophet algorithm (Nesvizhskii et al. (2003) *Anal Chem* 75: 4646-4658), and those that contained similar peptides and could not be differentiated based on an MS/MS analysis alone were grouped to satisfy the principles of parsimony.

Statistical analysis: Significance of all data was determined with two-way ANOVA, followed by Tukey's multiple comparisons post-test. Analysis was performed using GraphPad Prism 6 software (La Jolla, Calif.). *$P<0.05$, $P<0.01$, *$P<0.001$, ***$P<0.0001$.

Example 9

Results in Animal Model Demonstrating Immune Response to *Neisseria meningitidis*

Deletion of the outer membrane proteins (OMPs) PorA and RmpM results in diminished PorB-specific antibody binding to the PorB molecule, an effect that correlates with the decreased capacity of PorB-specific antibody to induce bacteriolysis in antibody-dependent complement-mediated killing assays. Deletion of dominant OMPs could impact immunogenicity and/or adjuvanticity of the meningococcal membrane surface. This effect was directly evaluated in an animal study.

Figure 5A:
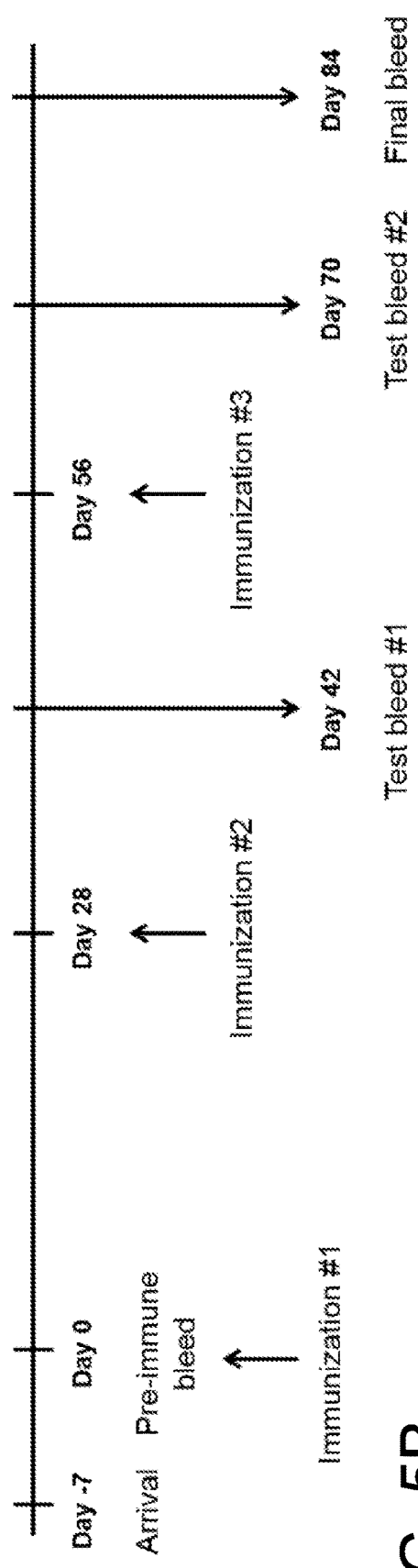

Outer membrane vesicles (OMVs) were isolated from the wild type (WT) parental MC58 strain and PorA deletion mutant strains ($\Delta A$, $\Delta AB$, $\Delta AR$, $\Delta ABR$, OCh) (Table 4). Two rabbits per group were immunized at three four-week intervals with 25 μg OMVs/aluminum hydroxide (FIG. 5A). Rabbits were also immunized with equivalent concentrations of the meningococcal BEXSERO® vaccine and phosphate buffered saline (PBS)/aluminum hydroxide alone as positive and negative controls, respectively. Following termination of the study, sera were obtained from each rabbit and assessed for the presence of antibodies capable of binding to and killing bacteria in a series of ELISAs, immunoblots, and serum bactericidal assays (SBAs).

Figure 5B:
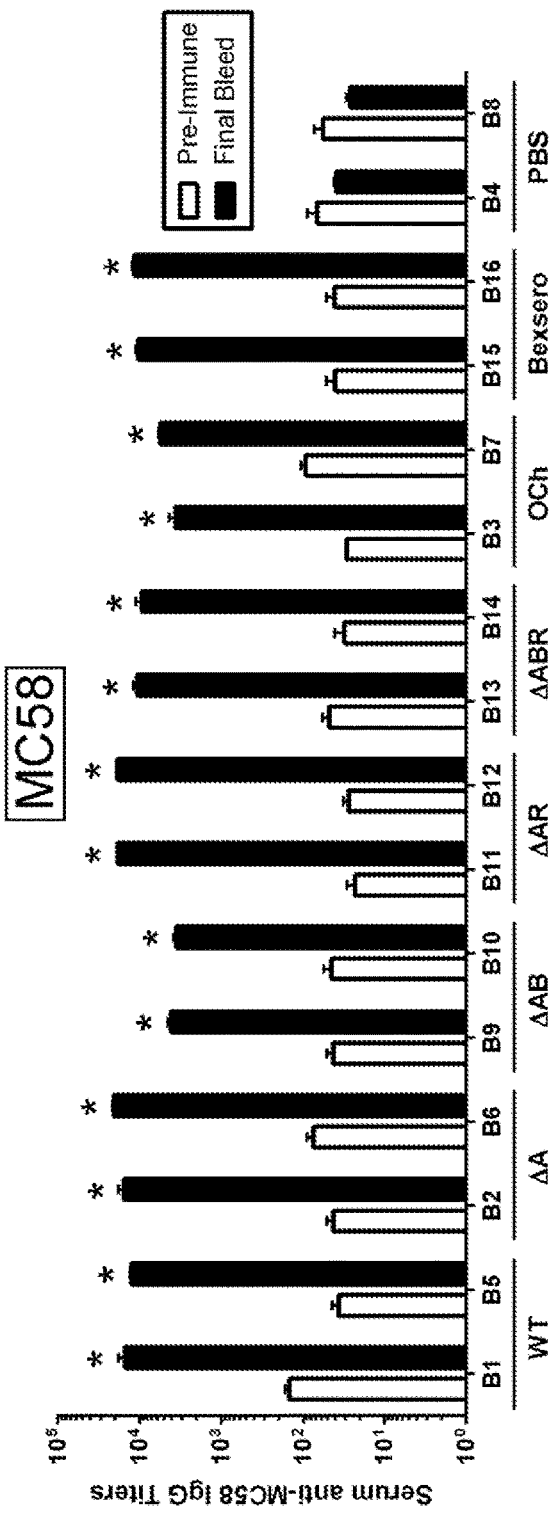
Figure 5C:
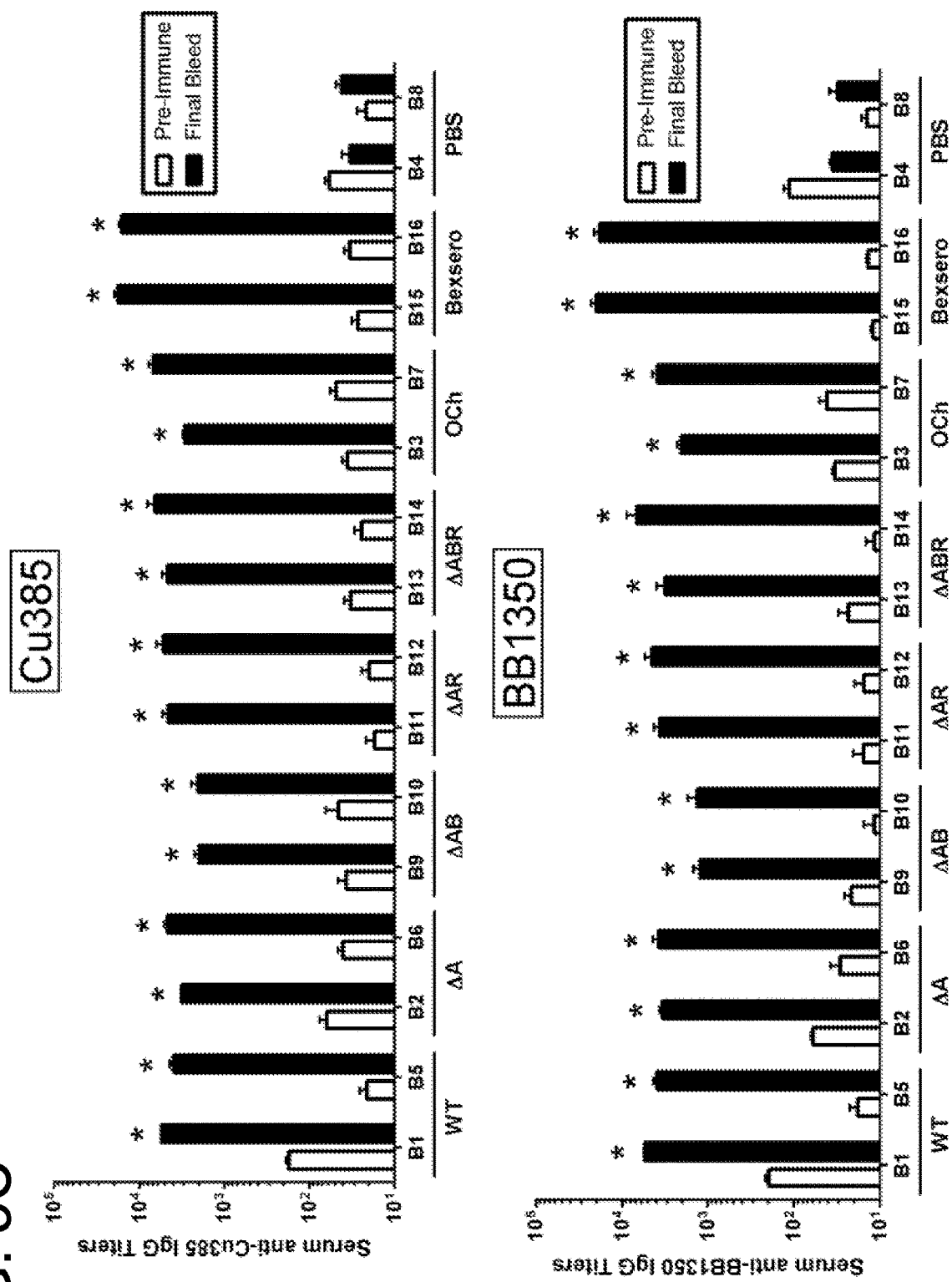
Figure 5D:
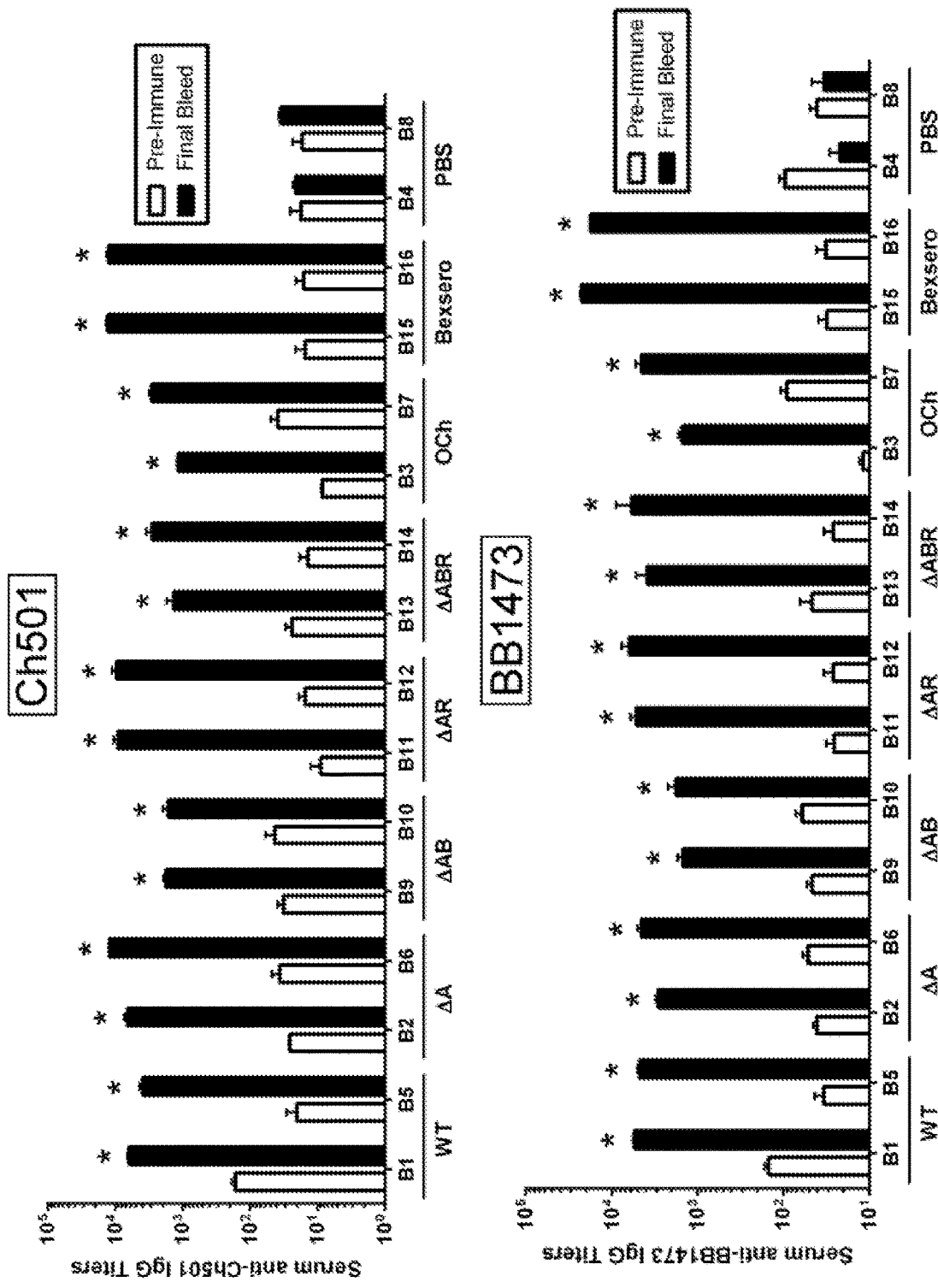

Whole cell ELISAs demonstrated the ability of all OMV antigens except the negative PBS control to induce antibody responses specific to the parental MC58 strain (FIG. 5B) and four heterogeneous serogroup B strains (FIGS. 5C and 5D). Antisera obtained from animals immunized with $\Delta AB$ or OCh OMV antigens, exhibited concentrations of antibodies binding to whole cells of *N. meningitidis* that were high but diminished relative to the other OMV antigens (FIGS. 5B-5D). Despite similarities in total antibody binding to whole cells, the sera exhibited differing bactericidal activity. Both the B1 and B5 sera obtained from rabbits immunized with WT OMVs were able to mediate killing of the homologous MC58 strain and the heterologous Cu385 strain in human serum bactericidal assays (hSBAs) (FIG. 6). B1 antibodies were also bactericidal against strain BB1350. A single deletion of PorA resulted in enhanced heterologous killing activity, as B2 serum antibodies were able to kill all strains tested and B6 serum antibodies were able to kill all but one (Cu385) (FIG. 6). Antibodies from both of the sera obtained from animals immunized with either $\Delta AB$ or $\Delta ABR$ OMVs exhibited the capacity to kill all five strains tested (FIG. 6), indicating that deletion of PorA and PorB in concert enhances immunogenicity of cross-protective OMPs.

The capacity of serum antibodies from $\Delta AB$ OMV- and $\Delta ABR$ OMV-immunized rabbits to kill heterologous meningococcal strains in hSBAs suggested the possibility that host immune responses were being directed against antigens that were distinct from those induced by immunization with PorA- and PorB-sufficient OMV types. To address this possibility, immunoblots were performed, probing whole cell lysates of the five strains tested in the hSBAs with serum antibodies from each of the six immunized rabbits. Antibodies from B1 and B5 sera, immunized with WT OMVs, bound dominant bands at ~17 and ~34 kDa (FIGS. 7A-7B). Bands of similar size were also bound by antibodies present in sera from animals immunized with $\Delta A$ (B2, B6) and OCh (B3, B7) OMVs, as well as BEXSERO® (B15, B16) (FIGS. 7A-7B). Sera from rabbits immunized with $\Delta AB$ (B9, B10) and $\Delta ABR$ (B13, B14) OMVs lacked antibodies capable of binding the same bands, but contained antibodies that bound higher MW bands of ~72 and ~95 kDa (FIGS. 7A-7B). The presence of antibodies capable of binding high molecular weight bands correlated with the ability to kill heterologous strains (≥4) in hSBAs, as demonstrated by the banding profiles of sera B2, B3, B6, B11, B15, and B16 (FIGS. 7A-7B).

TABLE 4

Description of OMV antigens.

| Antigen Name | Antigen Description |
|---|---|
| WT | OMVs from parental MC58 PorA+ PorB+ RmpM+ strain |
| $\Delta A$ | OMVs from WT strain deleted for PorA expression |
| $\Delta AB$ | OMVs from WT strain deleted for PorA and PorB expression |
| $\Delta AR$ | OMVs from WT strain deleted for PorA and RmpM expression |
| $\Delta ABR$ | OMVs from WT strain deleted for PorA, PorB, and RmpM expression |
| OCh | OMVs from WT strain deleted for PorA expression and containing a genetically mutated PorB loop 4 - loop 8 amino acid sequence relative to MC58 |
| BEXSERO® | Vaccine from GSK Pharmaceuticals containing OMVs from strain NZ98/254 exhibiting different PorA and PorB amino acid sequence types relative to MC58 |
| PBS | Negative control containing equimolar amounts of PBS and aluminum hydroxide given to experimental animals |

Example 10

Gonococcal Vaccine from N. meningitidis Triple Deletion Mutant Lacking PorA, PorB, and Reduction Modifiable Protein (RmpM) Proteins An in vivo gonococcal colonization study was conducted. In this study, mice (n=20 per group) were immunized at three fourteen day intervals with 12.5 µg outer membrane vesicles (OMVs)/aluminum hydroxide derived from (A) a wild type N. meningitidis MC58 strain containing PorA, PorB, and RmpM outer membrane proteins (OMPs), (B) strain ΔABR, in which strain MC58 has been deleted for PorA, PorB, and RmpM expression, or (C) strain OCh, in which strain MC58 has been deleted for PorA expression and the amino acid sequence of PorB is genetically altered in surface-expressed loops 4-8. Mice were also immunized with equimolar volumes of PBS/aluminum hydroxide or were unimmunized as negative controls. Following immunization, mice were intravaginally inoculated with N. gonorrhoeae strain F62 and colonization/antibody levels monitored over seven days (FIG. 8).

Mice immunized with MC58 OMVs began to clear gonococcal infection by 3 days post-infection (d.p.i.), with 39% of animals cleared by day 7 d.p.i. (FIG. 9A). These gross levels of clearance were greater than those of animals immunized with aluminum hydroxide (Alum) only or unimmunized (Unimm.) negative controls (17% and 19%, respectively), though the trend did not reach statistical significance when assessed by 2-way ANOVA (FIG. 9A). In contrast, significantly more mice immunized with either OCh or ΔABR OMVs cleared gonococci than both negative control groups, with only 23% of ΔABR OMV-immunized animals remaining colonized by 7 d.p.i. (FIG. 9A). OCh OMV- and ΔABR OMV-immunized animals also exhibited a corresponding median density of colonization equivalent to 0 CFU/ml by 7 d.p.i. (FIG. 9B).

The enhanced gonococcal clearance observed when mice were immunized with PorA-deficient OMV antigens suggested that other OMPs induced the production of antibodies that contributed to host protection. To identify those antigens, western blots were performed, probing whole cells lysates of gonococcal strains F62, FA19, FA1090, and MS11, with pooled antisera obtained from animals following the third immunization. Antibodies from sera of animals immunized with MC58, OCh, and ΔABR OMVs all bound a ~70 kDa protein present in all four gonococcal strains tested as well as the MC58 N. meningitidis strain from which the OMVs were derived (FIG. 10). Antibodies from OCh OMV- and ΔABR OMV-immunized mice also bound a ~75 kDa protein that was not bound by serum antibodies from MC58 OMV-immunized mice (FIG. 10). Polyclonal antibodies present in the ΔABR pooled sera bound a ~95 kDa protein that was not bound by MC58 or OCh pooled sera (FIG. 10). These data suggest unique antigens in OMV from deletion mutants contribute to the protective effect of the OCh and ΔABR OMVs observed in the in vivo clearance model.

Example 11

Additional Protocols

Construction of Additional Strains: To construct a triple deletion mutant strain of N. meningitidis in which the outer membrane proteins PorA, PorB, and RmpM are removed from the genome without replacement of a selectable marker, a plasmid is constructed incorporating ~1 kb homologous upstream (5') and downstream (3') intergenic sequence of the gene from the strain to be deleted. Following incorporation of the 5' and 3' sequences into a vector backbone, a counterselectable cassette derived from plasmid pJJ260 (Johnston, Gene 492: 325-328, 2012) bearing a kanamycin-resistance gene (nptII) and a levansucrase gene (sacB) expressed under the control of a tetracycline-inducible promoter (tetA) is inserted at the 5'/3' sequence junction. This allows for screening of clones by both a positive and negative selection mechanism; transformed strains that incorporate the plasmid into the genome via a double homologous recombination event will exhibit resistance to the antibiotic kanamycin but will be sensitive to the presence of sucrose, which is converted to the toxic product levan in the presence of induced levansucrase. The complete plasmid is transformed into N. meningitidis and deletion of the gene of interest is confirmed by (1) growth on selective media containing kanamycin and (2) the absence of growth on selective media containing sucrose and chlortetracycline. To remove the counterselectable cassette, the resulting deletion strain is transformed with the plasmid bearing the 5'/3' homologous sequence alone (without the counterselectable cassette). Absence of the cassette is confirmed by (1) growth on selective media containing sucrose and chlortetracycline, (2) the absence of growth on selective media containing kanamycin, and (3) genetic sequencing. The process is repeated for the remaining two genes until a PorA/PorB/RmpM triple deletion strain is constructed.

Construction of Strains and Compositions including Outer Membrane Microvesicles and Heterologous Proteins: Proteins identified through proteomics or bioinformatics screening that are suggestive of OMV-mediated protection against Neisseria species will be either (1) up-regulated in the ΔABR strain via genetic manipulation or (2) produced recombinantly and added as an additional antigen to the ΔABR OMVs. The following protocols are of use.

To construct a ΔABR OMV vaccine containing highly expressed protein antigens of interest, the endogenous promoter region of the corresponding gene is genetically deleted utilizing the same methods detailed for the clean triple deletion mutant and is replaced with an inducible promoter. The regions immediately upstream (5') and downstream (3') of the promoter are cloned into a plasmid, with a counterselectable cassette bearing the kanamycin-resistance gene nptII and the levansucrase gene sacB inserted at the 5'/3' junction. The counterselectable plasmid is transformed into strain ΔABR and the promoter deletion mutant isolated via screening with kanamycin. A second plasmid is constructed from the vector bearing the 5'/3' promoter-flanking regions. An isopropyl β-D-1-thiogalactopyranoside (IPTG)-inducible promoter (e.g. T5) is inserted directly upstream of the 3' region (encoding the open reading frame of the gene of interest) with two sequential genetic sequences encoding the lactose operator (lacO) and the ribosomal binding site sequence. Sequence encoding the lactose repressor gene (lacI), which binds to the lactose operator to control gene expression, is inserted directly downstream of the 5' region in the opposite orientation to the T5 promoter. The complete vector is transformed into the ΔABR strain containing the genomically-inserted counterselectable plasmid and replacement of the plasmid with the inducible T5 promoter is confirmed via selection on sucrose plates. Detoxified OMVs are obtained as per the protocol for the ΔABR strain except that IPTG is added to the medium to induce expression of T5-controlled genes during growth in culture.

To obtain recombinant antigens of specific *Neisseria* proteins, genes encoding the protein of interest are inserted in-frame into an expression vector containing a His-tag gene sequence (e.g. pET-28a(+)) downstream of the inducible T7 promoter. The vector is transformed into an *Escherichia coli* expression strain (e.g. BL21(DE3)); expression of the gene of interest is induced via growth in Luria Bertani medium in the presence of IPTG. Bacteria are lysed and His-tagged protein is purified by running the lysate over a nickel agarose column (Qiagen). Further purification is achieved by FPLC if necessary. Recombinant proteins are added to the ΔABR OMVs to produce a multi-component vaccine.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method of inducing an immune response to *Neisseria gonorrhoeae* in a mammalian subject, comprising administering to the mammalian subject an immunogenic composition comprising an effective amount of isolated $PorA^-PorB^-RmpM^-$ *N. meningitidis* outer membrane microvesicles, thereby inducing the immune response to the *Neisseria gonorrhoeae*.

2. The method of claim 1, wherein the immune response is a protective immune response.

3. The method of claim 1, wherein the mammalian subject has a *Neisseria gonorrhoeae* infection and the immune response is a therapeutic response.

4. The method of claim 3, wherein the subject has a *Neisseria gonorrhoeae* infection, and the administration of the immunogenic composition induces clearance of the *Neisseria gonorrhoeae*.

5. The method of claim 2, wherein the mammalian subject is a healthy subject.

6. The method of claim 1, wherein the mammalian subject is a human and the outer membrane microvesicles are purified.

7. A method of inducing antibodies that bind *Neisseria gonorrhoeae* in a mammalian subject, comprising selecting a mammalian subject with a *Neisseria gonorrhoeae* infection; and administering to the mammalian subject an immunogenic composition comprising an effective amount of isolate $PorA^-PorB^-RmpM^-$ *N. meningitidis* microvesicles and a pharmaceutically acceptable carrier, thereby inducing the antibodies that bind *Neisseria gonorrhoeae* in the mammalian subject.

8. The method of claim 7, wherein the microvesicles are outer membrane vesicles, blebs, or a combination thereof.

9. The method of claim 7, wherein the *N. meningitidis* is serogroup A, B or C.

10. The method of claim 7, wherein the immunogenic composition further comprises an adjuvant.

11. The method of claim 7, wherein the immune response is a protective immune response.

12. The method of claim 7, wherein the immune response is a therapeutic response.

13. The method of claim 12, wherein the subject has a *Neisseria gonorrhoeae* infection, and the administration of the immunogenic composition induces clearance of the *Neisseria gonorrhoeae*.

14. The method of claim 7, wherein the mammalian subject is a human and the outer membrane microvesicles are purified.

15. The method of claim 7, wherein the microvesicles are outer membrane vesicles or blebs.

16. The method of claim 1, wherein the isolated $PorA^-$ $PorB^-RmpM^-$ *N. meningitidis* is serogroup A, B or C.

17. The method of claim 1, wherein the microvesicles are outer membrane vesicles, blebs, or a combination thereof.

18. The method of claim 1, wherein the immunogenic composition comprises an adjuvant.

* * * * *

SEQUENCE LISTING

```
<160> NUMBER OF SEQ ID NOS: 51

<210> SEQ ID NO 1
<211> LENGTH: 28
<212> TYPE: DNA
<213> ORGANISM: Artificial Sequence
<220> FEATURE:
<223> OTHER INFORMATION: Primer

<400> SEQUENCE: 1
gactcatatg ttcagacatg gaatcgcc                                        28

<210> SEQ ID NO 2
<211> LENGTH: 31
<212> TYPE: DNA
<213> ORGANISM: Artificial Sequence
<220> FEATURE:
<223> OTHER INFORMATION: Primer

<400> SEQUENCE: 2
atatggatcc ttcagacggc gcatttttat g                                    31

<210> SEQ ID NO 3
<211> LENGTH: 28
<212> TYPE: DNA
<213> ORGANISM: Artificial Sequence
<220> FEATURE:
<223> OTHER INFORMATION: Primer

<400> SEQUENCE: 3
atatggatcc tgcaatgccc tccaatac                                        28

<210> SEQ ID NO 4
<211> LENGTH: 33
<212> TYPE: DNA
<213> ORGANISM: Artificial Sequence
<220> FEATURE:
<223> OTHER INFORMATION: Primer

<400> SEQUENCE: 4
cgcgtctaga tgctgtattc ctttttggt taa                                   33

<210> SEQ ID NO 5
<211> LENGTH: 32
<212> TYPE: DNA
<213> ORGANISM: Artificial Sequence
<220> FEATURE:
<223> OTHER INFORMATION: Primer

<400> SEQUENCE: 5
atatgcatgc tctgcaaaga ttggtatcaa ca                                   32

<210> SEQ ID NO 6
<211> LENGTH: 30
<212> TYPE: DNA
```

<213> ORGANISM: Artificial Sequence
<220> FEATURE:
<223> OTHER INFORMATION: Primer

<400> SEQUENCE: 6
atataagctt cagacggctg aaactcaacg                                    30

<210> SEQ ID NO 7
<211> LENGTH: 41
<212> TYPE: DNA
<213> ORGANISM: Artificial Sequence
<220> FEATURE:
<223> OTHER INFORMATION: Primer

<400> SEQUENCE: 7
atattctaga caccataggc tttagagaag tatttgaatg c                       41

<210> SEQ ID NO 8
<211> LENGTH: 40
<212> TYPE: DNA
<213> ORGANISM: Artificial Sequence
<220> FEATURE:
<223> OTHER INFORMATION: Primer

<400> SEQUENCE: 8
ccgagcatgc ttattattat ttcctcccgt taaataatag                         40

<210> SEQ ID NO 9
<211> LENGTH: 26
<212> TYPE: DNA
<213> ORGANISM: Artificial Sequence
<220> FEATURE:
<223> OTHER INFORMATION: Primer

<400> SEQUENCE: 9
atatggatcc aagccgagac tgcatc                                        26

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
cgcgtctaga atcggcttcc ttttgtaaat                                    30

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
atatgcatgc atatcggggc gg                                            22

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
atataagctt cagacggcgc attttttatgc                                   30

<210> SEQ ID NO 13
<211> LENGTH: 32
<212> TYPE: DNA
<213> ORGANISM: Artificial Sequence
<220> FEATURE:
<223> OTHER INFORMATION: Primer

<400> SEQUENCE: 13
atattctaga gggaaagcca ctttgtgtct ca                                  32

<210> SEQ ID NO 14
<211> LENGTH: 38
<212> TYPE: DNA
<213> ORGANISM: Artificial Sequence
<220> FEATURE:
<223> OTHER INFORMATION: Primer

<400> SEQUENCE: 14
gtatgcatgc ttattattag aaaaactcat cgagcatc                            38

<210> SEQ ID NO 15
<211> LENGTH: 27
<212> TYPE: DNA
<213> ORGANISM: Artificial Sequence
<220> FEATURE:
<223> OTHER INFORMATION: Primer

<400> SEQUENCE: 15
tagtggatcc aatcgtgcga tatggaa                                        27

<210> SEQ ID NO 16
<211> LENGTH: 37
<212> TYPE: DNA
<213> ORGANISM: Artificial Sequence
<220> FEATURE:
<223> OTHER INFORMATION: Primer

<400> SEQUENCE: 16
cgcgtctaga tttattccct cattaaattt gtacagc                             37

<210> SEQ ID NO 17
<211> LENGTH: 27
<212> TYPE: DNA
<213> ORGANISM: Artificial Sequence
<220> FEATURE:
<223> OTHER INFORMATION: Primer

<400> SEQUENCE: 17
gtatgcatgc ggctaggcaa tatcttg                                        27

<210> SEQ ID NO 18
<211> LENGTH: 36
<212> TYPE: DNA
<213> ORGANISM: Artificial Sequence
<220> FEATURE:
<223> OTHER INFORMATION: Primer

<400> SEQUENCE: 18
atataagctt cagacggcgt taatccacta taaagc                              36

<210> SEQ ID NO 19
<211> LENGTH: 33
<212> TYPE: DNA
<213> ORGANISM: Artificial Sequence
<220> FEATURE:

<223> OTHER INFORMATION: Primer

<400> SEQUENCE: 19
gtattctaga cgccgaataa atacctgtga cgg                            33

<210> SEQ ID NO 20
<211> LENGTH: 28
<212> TYPE: DNA
<213> ORGANISM: Artificial Sequence
<220> FEATURE:
<223> OTHER INFORMATION: Primer

<400> SEQUENCE: 20
atatgcatgc ttattattac gccccgcc                                  28

<210> SEQ ID NO 21
<211> LENGTH: 36
<212> TYPE: DNA
<213> ORGANISM: Artificial Sequence
<220> FEATURE:
<223> OTHER INFORMATION: Primer

<400> SEQUENCE: 21
atattctaga atgaaaaaat ccctgattgc cctgac                         36

<210> SEQ ID NO 22
<211> LENGTH: 29
<212> TYPE: DNA
<213> ORGANISM: Artificial Sequence
<220> FEATURE:
<223> OTHER INFORMATION: Primer

<400> SEQUENCE: 22
gaagaagcca ccgtttttgt agttgaagc                                 29

<210> SEQ ID NO 23
<211> LENGTH: 25
<212> TYPE: DNA
<213> ORGANISM: Artificial Sequence
<220> FEATURE:
<223> OTHER INFORMATION: Primer

<400> SEQUENCE: 23
aacggtggct tcttcgtgca atatg                                     25

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
agaaactcgg ggcgttacgt tg                                        22

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
acgccccgag tttcttacgc                                           20

```
<210> SEQ ID NO 26
<211> LENGTH: 28
<212> TYPE: DNA
<213> ORGANISM: Artificial Sequence
<220> FEATURE:
<223> OTHER INFORMATION: Primer

<400> SEQUENCE: 26
atatgcatgc ttagaatttg tggcgcag                                    28

<210> SEQ ID NO 27
<211> LENGTH: 28
<212> TYPE: DNA
<213> ORGANISM: Artificial Sequence
<220> FEATURE:
<223> OTHER INFORMATION: Primer

<400> SEQUENCE: 27
atatgcatgc gaaagccact ttgtgtct                                    28

<210> SEQ ID NO 28
<211> LENGTH: 29
<212> TYPE: DNA
<213> ORGANISM: Artificial Sequence
<220> FEATURE:
<223> OTHER INFORMATION: Primer

<400> SEQUENCE: 28
atatcatatg gacgttaccc tgtacggca                                   29

<210> SEQ ID NO 29
<211> LENGTH: 27
<212> TYPE: DNA
<213> ORGANISM: Artificial Sequence
<220> FEATURE:
<223> OTHER INFORMATION: Primer

<400> SEQUENCE: 29
atatgctcag cttagaattt gtggcgc                                     27

<210> SEQ ID NO 30
<211> LENGTH: 30
<212> TYPE: DNA
<213> ORGANISM: Artificial Sequence
<220> FEATURE:
<223> OTHER INFORMATION: Primer

<400> SEQUENCE: 30
atatcatatg gatgtcagcc tatacggcga                                  30

<210> SEQ ID NO 31
<211> LENGTH: 27
<212> TYPE: DNA
<213> ORGANISM: Artificial Sequence
<220> FEATURE:
<223> OTHER INFORMATION: Primer

<400> SEQUENCE: 31
atatctcgag gaatttgtgg cgcaaac                                     27

<210> SEQ ID NO 32
<211> LENGTH: 20
<212> TYPE: DNA
<213> ORGANISM: Artificial Sequence
<220> FEATURE:
<223> OTHER INFORMATION: Primer
```

<400> SEQUENCE: 32
tgtcggacgt aatgcttttg                                                                                   20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
ggcaatttcg gtcgtactgt                                                                                   20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
caatacgcgc ttaacgacaa                                                                                   20

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
gaagcgtaca gggcatcatt                                                                                   20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
gcgcaaccct tgtcattagt                                                                                   20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
cggactacga tcggttttgt                                                                                   20

<210> SEQ ID NO 38
<211> LENGTH: 331
<212> TYPE: PRT
<213> ORGANISM: Artificial Sequence
<220> FEATURE:
<223> OTHER INFORMATION: Chimeric PorB Protein

<400> SEQUENCE: 38

Met Lys Lys Ser Leu Ile Ala Leu Thr Leu Ala Ala Leu Pro Val Ala
1               5                   10                  15

Ala Met Ala Asp Val Thr Leu Tyr Gly Thr Ile Lys Ala Gly Val Glu
            20                  25                  30

```
Thr Ser Arg Ser Val Phe His Gln Asn Gly Gln Val Thr Glu Val Thr
        35                  40                  45

Thr Ala Thr Gly Ile Val Asp Leu Gly Ser Lys Ile Gly Phe Lys Gly
 50                  55                  60

Gln Glu Asp Leu Gly Asn Gly Leu Lys Ala Ile Trp Gln Val Glu Gln
 65                  70                  75                  80

Lys Ala Ser Ile Ala Gly Thr Asp Ser Gly Trp Gly Asn Arg Gln Ser
                 85                  90                  95

Phe Ile Gly Leu Lys Gly Gly Phe Gly Lys Leu Arg Val Gly Arg Leu
                100                 105                 110

Asn Ser Val Leu Lys Asp Thr Gly Asp Ile Asn Pro Trp Asp Ser Lys
                115                 120                 125

Ser Asp Tyr Leu Gly Val Asn Lys Ile Ala Glu Pro Glu Ala Arg Leu
    130                 135                 140

Ile Ser Val Arg Tyr Asp Ser Pro Glu Phe Ala Gly Leu Ser Gly Ser
145                 150                 155                 160

Val Gln Tyr Ala Leu Asn Asp Asn Ala Gly Arg His Asn Ser Glu Ser
                165                 170                 175

Tyr His Ala Gly Phe Asn Tyr Lys Asn Gly Phe Phe Val Gln Tyr
                180                 185                 190

Gly Gly Ala Tyr Lys Arg His His Gln Val Gln Glu Gly Leu Asn Ile
                195                 200                 205

Glu Lys Tyr Gln Ile His Arg Leu Val Ser Gly Tyr Asp Asn Asp Ala
210                 215                 220

Leu Tyr Ala Ser Val Ala Val Gln Gln Gln Asp Ala Lys Leu Thr Asp
225                 230                 235                 240

Ala Ser Asn Ser His Asn Ser Gln Thr Glu Val Ala Ala Thr Leu Ala
                245                 250                 255

Tyr Arg Phe Gly Asn Val Thr Pro Arg Val Ser Tyr Ala His Gly Phe
                260                 265                 270

Lys Gly Leu Val Asp Asp Ala Asp Ile Gly Asn Glu Tyr Asp Gln Val
                275                 280                 285

Val Val Gly Ala Glu Tyr Asp Phe Ser Lys Arg Thr Ser Ala Leu Val
                290                 295                 300

Ser Ala Gly Trp Leu Gln Glu Gly Lys Gly Glu Asn Lys Phe Val Ala
305                 310                 315                 320

Thr Ala Gly Gly Val Gly Leu Arg His Lys Phe
                325                 330

<210> SEQ ID NO 39
<211> LENGTH: 331
<212> TYPE: PRT
<213> ORGANISM: Artificial Sequence
<220> FEATURE:
<223> OTHER INFORMATION: Chimeric PorB Protein

<400> SEQUENCE: 39

Met Lys Lys Ser Leu Ile Ala Leu Thr Leu Ala Ala Leu Pro Val Ala
  1               5                  10                  15

Ala Met Ala Asp Val Thr Leu Tyr Gly Thr Ile Lys Ala Gly Val Glu
                 20                  25                  30

Thr Ser Arg Ser Val Phe His Gln Asn Gly Gln Val Thr Glu Val Thr
                 35                  40                  45

Thr Ala Thr Gly Ile Val Asp Leu Gly Ser Lys Ile Gly Phe Lys Gly
 50                  55                  60
```

```
Gln Glu Asp Leu Gly Asn Gly Leu Lys Ala Ile Trp Gln Val Glu Gln
 65                  70                  75                  80

Lys Ala Ser Ile Ala Gly Thr Asp Ser Gly Trp Gly Asn Arg Gln Ser
             85                  90                  95

Phe Ile Gly Leu Lys Gly Phe Gly Lys Leu Arg Val Gly Arg Leu
        100                 105                 110

Asn Ser Val Leu Lys Asp Thr Gly Asp Ile Asn Pro Trp Asp Ser Lys
            115                 120                 125

Ser Asp Tyr Leu Gly Val Asn Lys Ile Ala Glu Pro Glu Ala Arg Leu
        130                 135                 140

Ile Ser Val Arg Tyr Asp Ser Pro Glu Phe Ala Gly Leu Ser Gly Ser
145                 150                 155                 160

Val Gln Tyr Ala Leu Asn Asp Asn Ala Gly Lys Tyr Asn Ser Glu Ser
                165                 170                 175

Tyr His Ala Gly Phe Asn Tyr Lys Asn Gly Phe Phe Val Gln Tyr
            180                 185                 190

Gly Gly Ala Tyr Lys Arg His Val Arg Val Asp Glu Asn Val Asn Ile
            195                 200                 205

Glu Lys Tyr Gln Ile His Arg Leu Val Ser Gly Tyr Asp Asn Asp Ala
210                 215                 220

Leu His Ala Ser Val Ala Val Gln Gln Gln Asp Ala Lys Leu Val Glu
225                 230                 235                 240

Asp Asn Tyr Ser His Asn Ser Gln Thr Glu Val Ala Ala Thr Leu Ala
                245                 250                 255

Tyr Arg Phe Gly Asn Val Thr Pro Arg Val Ser Tyr Ala His Gly Phe
            260                 265                 270

Lys Gly Ser Phe Asp Asp Ala Asp Leu Ser Asn Asp Tyr Asp Gln Val
        275                 280                 285

Val Val Gly Ala Glu Tyr Asp Phe Ser Lys Arg Thr Ser Ala Leu Val
    290                 295                 300

Ser Ala Gly Trp Leu Gln Glu Gly Lys Gly Glu Asn Lys Phe Val Ser
305                 310                 315                 320

Thr Ala Gly Gly Val Gly Leu Arg His Lys Phe
            325                 330
```

<210> SEQ ID NO 40
<211> LENGTH: 331
<212> TYPE: PRT
<213> ORGANISM: Artificial Sequence
<220> FEATURE:
<223> OTHER INFORMATION: Chimeric PorB Protein

<400> SEQUENCE: 40

```
Met Lys Lys Ser Leu Ile Ala Leu Thr Leu Ala Ala Leu Pro Val Ala
1               5                   10                  15

Ala Met Ala Asp Val Thr Leu Tyr Gly Thr Ile Lys Ala Gly Val Glu
            20                  25                  30

Thr Ser Arg Ser Val Phe His Gln Asn Gly Gln Val Thr Glu Val Thr
        35                  40                  45

Thr Ala Thr Gly Ile Val Asp Leu Gly Ser Lys Ile Gly Phe Lys Gly
    50                  55                  60

Gln Glu Asp Leu Gly Asn Gly Leu Lys Ala Ile Trp Gln Val Glu Gln
65                  70                  75                  80

Lys Ala Ser Ile Ala Gly Thr Asp Ser Gly Trp Gly Asn Arg Gln Ser
                85                  90                  95
```

```
Phe Ile Gly Leu Lys Gly Gly Phe Gly Lys Leu Arg Val Gly Arg Leu
            100                 105                 110

Asn Ser Val Leu Lys Asp Thr Gly Asp Ile Asn Pro Trp Asp Ser Lys
            115                 120                 125

Ser Asp Tyr Leu Gly Val Asn Lys Ile Ala Glu Pro Glu Ala Arg Leu
            130                 135                 140

Ile Ser Val Arg Tyr Asp Ser Pro Glu Phe Ala Gly Leu Ser Gly Ser
145                 150                 155                 160

Val Gln Tyr Ala Leu Asn Asp Asn Ala Gly Arg His Asn Ser Glu Ser
                165                 170                 175

Tyr His Ala Gly Phe Asn Tyr Lys Asn Gly Gly Phe Phe Val Gln Tyr
                180                 185                 190

Gly Gly Ala Tyr Lys Arg His Val Arg Val Asp Glu Asn Val Asn Ile
                195                 200                 205

Glu Lys Tyr Gln Ile His Arg Leu Val Ser Gly Tyr Asp Asn Asp Ala
                210                 215                 220

Leu His Ala Ser Val Ala Val Gln Gln Gln Asp Ala Lys Leu Val Glu
225                 230                 235                 240

Asp Asn Tyr Ser His Asn Ser Gln Thr Glu Val Ala Ala Thr Leu Ala
                245                 250                 255

Tyr Arg Phe Gly Asn Val Thr Pro Arg Val Ser Tyr Ala His Gly Phe
                260                 265                 270

Lys Gly Ser Phe Asp Asp Ala Asp Leu Ser Asn Asp Tyr Asp Gln Val
                275                 280                 285

Val Val Gly Ala Glu Tyr Asp Phe Ser Lys Arg Thr Ser Ala Leu Val
                290                 295                 300

Ser Ala Gly Trp Leu Gln Glu Gly Lys Gly Glu Asn Lys Phe Val Ser
305                 310                 315                 320

Thr Ala Gly Gly Val Gly Leu Arg His Lys Phe
                325                 330

<210> SEQ ID NO 41
<211> LENGTH: 331
<212> TYPE: PRT
<213> ORGANISM: Artificial Sequence
<220> FEATURE:
<223> OTHER INFORMATION: Chimeric PorB Protein

<400> SEQUENCE: 41

Met Lys Lys Ser Leu Ile Ala Leu Thr Leu Ala Ala Leu Pro Val Ala
1               5                   10                  15

Ala Met Ala Asp Val Thr Leu Tyr Gly Thr Ile Lys Ala Gly Val Glu
                20                  25                  30

Thr Ser Arg Ser Val Phe His Gln Asn Gly Gln Val Thr Glu Val Thr
            35                  40                  45

Thr Ala Thr Gly Ile Val Asp Leu Gly Ser Lys Ile Gly Phe Lys Gly
        50                  55                  60

Gln Glu Asp Leu Gly Asn Gly Leu Lys Ala Ile Trp Gln Val Glu Gln
65                  70                  75                  80

Lys Ala Ser Ile Ala Gly Thr Asp Ser Gly Trp Gly Asn Arg Gln Ser
                85                  90                  95

Phe Ile Gly Leu Lys Gly Gly Phe Gly Lys Leu Arg Val Gly Arg Leu
            100                 105                 110

Asn Ser Val Leu Lys Asp Thr Gly Asp Ile Asn Pro Trp Asp Ser Lys
            115                 120                 125
```

```
Ser Asp Tyr Leu Gly Val Asn Lys Ile Ala Glu Pro Glu Ala Arg Leu
    130                 135                 140

Ile Ser Val Arg Tyr Asp Ser Pro Glu Phe Ala Gly Leu Ser Gly Ser
145                 150                 155                 160

Val Gln Tyr Ala Leu Asn Asp Asn Ala Gly Arg His Asn Ser Glu Ser
                165                 170                 175

Tyr His Ala Gly Phe Asn Tyr Lys Asn Gly Phe Phe Val Gln Tyr
                180                 185                 190

Gly Gly Ala Tyr Lys Arg His His Gln Val Gln Gly Leu Asn Ile
            195                 200                 205

Glu Lys Tyr Gln Ile His Arg Leu Val Ser Gly Tyr Asp Asn Asp Ala
    210                 215                 220

Leu Tyr Ala Ser Val Ala Val Gln Gln Gln Asp Ala Lys Leu Thr Asp
225                 230                 235                 240

Ala Ser Asn Ser His Asn Ser Gln Thr Glu Val Ala Ala Thr Leu Ala
                245                 250                 255

Tyr Arg Phe Gly Asn Val Thr Pro Arg Val Ser Tyr Ala His Gly Phe
                260                 265                 270

Lys Gly Ser Phe Asp Asp Ala Asp Leu Ser Asn Asp Tyr Asp Gln Val
                275                 280                 285

Val Val Gly Ala Glu Tyr Asp Phe Ser Lys Arg Thr Ser Ala Leu Val
290                 295                 300

Ser Ala Gly Trp Leu Gln Glu Gly Lys Gly Glu Asn Lys Phe Val Ser
305                 310                 315                 320

Thr Ala Gly Gly Val Gly Leu Arg His Lys Phe
                325                 330

<210> SEQ ID NO 42
<211> LENGTH: 331
<212> TYPE: PRT
<213> ORGANISM: Artificial Sequence
<220> FEATURE:
<223> OTHER INFORMATION: Chimeric PorB protein

<400> SEQUENCE: 42

Met Lys Lys Ser Leu Ile Ala Leu Thr Leu Ala Ala Leu Pro Val Ala
1               5                   10                  15

Ala Met Ala Asp Val Thr Leu Tyr Gly Thr Ile Lys Ala Gly Val Glu
                20                  25                  30

Thr Ser Arg Ser Val Phe His Gln Asn Gly Gln Val Thr Glu Val Thr
            35                  40                  45

Thr Ala Thr Gly Ile Val Asp Leu Gly Ser Lys Ile Gly Phe Lys Gly
50                  55                  60

Gln Glu Asp Leu Gly Asn Gly Leu Lys Ala Ile Trp Gln Val Glu Gln
65                  70                  75                  80

Lys Ala Ser Ile Ala Gly Thr Asp Ser Gly Trp Gly Asn Arg Gln Ser
                85                  90                  95

Phe Ile Gly Leu Lys Gly Gly Phe Gly Lys Leu Arg Val Gly Arg Leu
                100                 105                 110

Asn Ser Val Leu Lys Asp Thr Gly Asp Ile Asn Pro Trp Asp Ser Lys
            115                 120                 125

Ser Asp Tyr Leu Gly Val Asn Lys Ile Ala Glu Pro Glu Ala Arg Leu
    130                 135                 140

Ile Ser Val Arg Tyr Asp Ser Pro Glu Phe Ala Gly Leu Ser Gly Ser
145                 150                 155                 160
```

```
Val Gln Tyr Ala Leu Asn Asp Asn Ala Gly Arg His Asn Ser Glu Ser
                165                 170                 175

Tyr His Ala Gly Phe Asn Tyr Lys Asn Gly Gly Phe Phe Val Gln Tyr
            180                 185                 190

Gly Gly Ala Tyr Lys Arg His Val Arg Val Asp Glu Asn Val Asn Ile
        195                 200                 205

Glu Lys Tyr Gln Ile His Arg Leu Val Ser Gly Tyr Asp Asn Asp Ala
    210                 215                 220

Leu His Ala Ser Val Ala Val Gln Gln Gln Asp Ala Lys Leu Val Glu
225                 230                 235                 240

Asp Asn Tyr Ser His Asn Ser Gln Thr Glu Val Ala Ala Thr Leu Ala
                245                 250                 255

Tyr Arg Phe Gly Asn Val Thr Pro Arg Val Ser Tyr Ala His Gly Phe
            260                 265                 270

Lys Gly Leu Val Asp Asp Ala Asp Ile Gly Asn Glu Tyr Asp Gln Val
        275                 280                 285

Val Val Gly Ala Glu Tyr Asp Phe Ser Lys Arg Thr Ser Ala Leu Val
    290                 295                 300

Ser Ala Gly Trp Leu Gln Glu Gly Lys Gly Glu Asn Lys Phe Val Ala
305                 310                 315                 320

Thr Ala Gly Gly Val Gly Leu Arg His Lys Phe
                325                 330
```

<210> SEQ ID NO 43
<211> LENGTH: 331
<212> TYPE: PRT
<213> ORGANISM: Artificial Sequence
<220> FEATURE:
<223> OTHER INFORMATION: Chimeric PorB Protein
<400> SEQUENCE: 43

```
Met Lys Lys Ser Leu Ile Ala Leu Thr Leu Ala Ala Leu Pro Val Ala
1               5                   10                  15

Ala Met Ala Asp Val Thr Leu Tyr Gly Thr Ile Lys Ala Gly Val Glu
            20                  25                  30

Thr Ser Arg Ser Val Glu His Asn Gly Gly Gln Val Val Ser Val Glu
        35                  40                  45

Thr Gly Thr Gly Ile Val Asp Leu Gly Ser Lys Ile Gly Phe Lys Gly
    50                  55                  60

Gln Glu Asp Leu Gly Asn Gly Leu Lys Ala Ile Trp Gln Val Glu Gln
65                  70                  75                  80

Lys Ala Ser Ile Ala Gly Thr Asp Ser Gly Trp Gly Asn Arg Gln Ser
                85                  90                  95

Phe Ile Gly Leu Lys Gly Gly Phe Gly Lys Leu Arg Val Gly Arg Leu
            100                 105                 110

Asn Ser Val Leu Lys Asp Thr Gly Asp Ile Asn Pro Trp Asp Ser Lys
        115                 120                 125

Ser Asp Tyr Leu Gly Val Asn Lys Ile Ala Glu Pro Glu Ala Arg Leu
    130                 135                 140

Ile Ser Val Arg Tyr Asp Ser Pro Glu Phe Ala Gly Leu Ser Gly Ser
145                 150                 155                 160

Val Gln Tyr Ala Leu Asn Asp Asn Ala Gly Lys Tyr Asn Ser Glu Ser
                165                 170                 175

Tyr His Ala Gly Phe Asn Tyr Lys Asn Gly Gly Phe Phe Val Gln Tyr
            180                 185                 190
```

```
Gly Gly Ala Tyr Lys Arg His His Gln Val Gln Glu Gly Leu Asn Ile
            195                 200                 205

Glu Lys Tyr Gln Ile His Arg Leu Val Ser Gly Tyr Asp Asn Asp Ala
210                 215                 220

Leu Tyr Ala Ser Val Ala Val Gln Gln Gln Asp Ala Lys Leu Thr Asp
225                 230                 235                 240

Ala Ser Asn Ser His Asn Ser Gln Thr Glu Val Ala Ala Thr Leu Ala
            245                 250                 255

Tyr Arg Phe Gly Asn Val Thr Pro Arg Val Ser Tyr Ala His Gly Phe
            260                 265                 270

Lys Gly Leu Val Asp Asp Ala Asp Ile Gly Asn Glu Tyr Asp Gln Val
            275                 280                 285

Val Val Gly Ala Glu Tyr Asp Phe Ser Lys Arg Thr Ser Ala Leu Val
            290                 295                 300

Ser Ala Gly Trp Leu Gln Glu Gly Lys Gly Glu Asn Lys Phe Val Ala
305                 310                 315                 320

Thr Ala Gly Gly Val Gly Leu Arg His Lys Phe
            325                 330

<210> SEQ ID NO 44
<211> LENGTH: 331
<212> TYPE: PRT
<213> ORGANISM: Artificial Sequence
<220> FEATURE:
<223> OTHER INFORMATION: Chimeric PorB Protein

<400> SEQUENCE: 44

Met Lys Lys Ser Leu Ile Ala Leu Thr Leu Ala Ala Leu Pro Val Ala
1               5                   10                  15

Ala Met Ala Asp Val Thr Leu Tyr Gly Thr Ile Lys Ala Gly Val Glu
            20                  25                  30

Thr Ser Arg Ser Val Glu His Asn Gly Gly Gln Val Val Ser Val Glu
        35                  40                  45

Thr Gly Thr Gly Ile Val Asp Leu Gly Ser Lys Ile Gly Phe Lys Gly
    50                  55                  60

Gln Glu Asp Leu Gly Asn Gly Leu Lys Ala Ile Trp Gln Val Glu Gln
65                  70                  75                  80

Lys Ala Ser Ile Ala Gly Thr Asp Ser Gly Trp Gly Asn Arg Gln Ser
                85                  90                  95

Phe Ile Gly Leu Lys Gly Gly Phe Gly Lys Leu Arg Val Gly Arg Leu
            100                 105                 110

Asn Ser Val Leu Lys Asp Thr Gly Asp Ile Asn Pro Trp Asp Ser Lys
        115                 120                 125

Ser Asp Tyr Leu Gly Val Asn Lys Ile Ala Glu Pro Glu Ala Arg Leu
    130                 135                 140

Ile Ser Val Arg Tyr Asp Ser Pro Glu Phe Ala Gly Leu Ser Gly Ser
145                 150                 155                 160

Val Gln Tyr Ala Leu Asn Asp Asn Ala Gly Lys Tyr Asn Ser Glu Ser
                165                 170                 175

Tyr His Ala Gly Phe Asn Tyr Lys Asn Gly Gly Phe Phe Val Gln Tyr
            180                 185                 190

Gly Gly Ala Tyr Lys Arg His Val Arg Val Asp Glu Asn Val Asn Ile
            195                 200                 205

Glu Lys Tyr Gln Ile His Arg Leu Val Ser Gly Tyr Asp Asn Asp Ala
210                 215                 220
```

```
Leu His Ala Ser Val Ala Val Gln Gln Gln Asp Ala Lys Leu Val Glu
225                 230                 235                 240

Asp Asn Tyr Ser His Asn Ser Gln Thr Glu Val Ala Ala Thr Leu Ala
            245                 250                 255

Tyr Arg Phe Gly Asn Val Thr Pro Arg Val Ser Tyr Ala His Gly Phe
        260                 265                 270

Lys Gly Leu Val Asp Asp Ala Asp Ile Gly Asn Glu Tyr Asp Gln Val
    275                 280                 285

Val Val Gly Ala Glu Tyr Asp Phe Ser Lys Arg Thr Ser Ala Leu Val
290                 295                 300

Ser Ala Gly Trp Leu Gln Glu Gly Lys Gly Glu Asn Lys Phe Val Ala
305                 310                 315                 320

Thr Ala Gly Gly Val Gly Leu Arg His Lys Phe
                325                 330
```

<210> SEQ ID NO 45
<211> LENGTH: 331
<212> TYPE: PRT
<213> ORGANISM: Artificial Sequence
<220> FEATURE:
<223> OTHER INFORMATION: Chimeric PorB Protein

<400> SEQUENCE: 45

```
Met Lys Lys Ser Leu Ile Ala Leu Thr Leu Ala Leu Pro Val Ala
1               5                   10                  15

Ala Met Ala Asp Val Thr Leu Tyr Gly Thr Ile Lys Ala Gly Val Glu
            20                  25                  30

Thr Ser Arg Ser Val Glu His Asn Gly Gly Gln Val Val Ser Val Glu
        35                  40                  45

Thr Gly Thr Gly Ile Val Asp Leu Gly Ser Lys Ile Gly Phe Lys Gly
    50                  55                  60

Gln Glu Asp Leu Gly Asn Gly Leu Lys Ala Ile Trp Gln Val Glu Gln
65                  70                  75                  80

Lys Ala Ser Ile Ala Gly Thr Asp Ser Gly Trp Gly Asn Arg Gln Ser
                85                  90                  95

Phe Ile Gly Leu Lys Gly Gly Phe Gly Lys Leu Arg Val Gly Arg Leu
            100                 105                 110

Asn Ser Val Leu Lys Asp Thr Gly Asp Ile Asn Pro Trp Asp Ser Lys
        115                 120                 125

Ser Asp Tyr Leu Gly Val Asn Lys Ile Ala Glu Pro Glu Ala Arg Leu
    130                 135                 140

Ile Ser Val Arg Tyr Asp Ser Pro Glu Phe Ala Gly Leu Ser Gly Ser
145                 150                 155                 160

Val Gln Tyr Ala Leu Asn Asp Asn Ala Gly Lys Tyr Asn Ser Glu Ser
                165                 170                 175

Tyr His Ala Gly Phe Asn Tyr Lys Asn Gly Gly Phe Phe Val Gln Tyr
            180                 185                 190

Gly Gly Ala Tyr Lys Arg His His Gln Val Gln Glu Gly Leu Asn Ile
        195                 200                 205

Glu Lys Tyr Gln Ile His Arg Leu Val Ser Gly Tyr Asp Asn Asp Ala
    210                 215                 220

Leu Tyr Ala Ser Val Ala Val Gln Gln Gln Asp Ala Lys Leu Thr Asp
225                 230                 235                 240

Ala Ser Asn Ser His Asn Ser Gln Thr Glu Val Ala Ala Thr Leu Ala
                245                 250                 255
```

```
Tyr Arg Phe Gly Asn Val Thr Pro Arg Val Ser Tyr Ala His Gly Phe
            260                 265                 270

Lys Gly Ser Phe Asp Asp Ala Asp Leu Ser Asn Asp Tyr Asp Gln Val
            275                 280                 285

Val Val Gly Ala Glu Tyr Asp Phe Ser Lys Arg Thr Ser Ala Leu Val
    290                 295                 300

Ser Ala Gly Trp Leu Gln Glu Gly Lys Gly Glu Asn Lys Phe Val Ser
305                 310                 315                 320

Thr Ala Gly Gly Val Gly Leu Arg His Lys Phe
                    325                 330

<210> SEQ ID NO 46
<211> LENGTH: 330
<212> TYPE: PRT
<213> ORGANISM: Artificial Sequence
<220> FEATURE:
<223> OTHER INFORMATION: Chimeric PorB Protein

<400> SEQUENCE: 46

Met Lys Lys Ser Leu Ile Ala Leu Thr Leu Ala Ala Leu Pro Val Ala
1               5                   10                  15

Ala Met Ala Asp Val Thr Leu Tyr Gly Thr Ile Lys Ala Gly Val Glu
            20                  25                  30

Thr Ser Arg Ser Val Phe His Gln Asn Gly Gln Val Thr Glu Val Thr
        35                  40                  45

Thr Ala Thr Gly Ile Val Asp Leu Gly Ser Lys Ile Gly Phe Lys Gly
    50                  55                  60

Gln Glu Asp Leu Gly Asn Gly Leu Lys Ala Ile Trp Gln Val Glu Gln
65                  70                  75                  80

Lys Ala Ser Ile Ala Gly Thr Asp Ser Gly Trp Gly Asn Arg Gln Ser
                85                  90                  95

Phe Ile Gly Leu Lys Gly Gly Phe Gly Lys Leu Arg Val Gly Arg Leu
            100                 105                 110

Asn Ser Val Leu Lys Asp Thr Gly Asp Ile Asn Pro Trp Asp Ser Lys
        115                 120                 125

Ser Asp Tyr Leu Gly Val Asn Lys Ile Ala Glu Pro Glu Ala Arg Leu
    130                 135                 140

Ile Ser Val Arg Tyr Asp Ser Pro Glu Phe Ala Gly Leu Ser Gly Ser
145                 150                 155                 160

Val Gln Tyr Ala Leu Asn Asp Asn Ala Gly Arg His Asn Ser Glu Ser
                165                 170                 175

Tyr His Ala Gly Phe Asn Tyr Lys Asn Gly Gly Phe Phe Val Gln Tyr
            180                 185                 190

Gly Gly Ala Tyr Lys Arg His Gln Asp Val Asp Val Lys Ile Glu
            195                 200                 205

Lys Tyr Gln Ile His Arg Leu Val Ser Gly Tyr Asp Asn Asp Ala Leu
    210                 215                 220

His Ala Ser Val Ala Val Gln Gln Gln Asp Ala Lys Leu Val Glu Asp
225                 230                 235                 240

Asn Tyr Ser His Asn Ser Gln Thr Glu Val Ala Ala Thr Leu Ala Tyr
                245                 250                 255

Arg Phe Gly Asn Val Thr Pro Arg Val Ser Tyr Ala His Gly Phe Lys
            260                 265                 270

Gly Ser Phe Asp Asp Ala Asp Leu Ser Asn Asp Tyr Asp Gln Val Val
        275                 280                 285
```

Val Gly Ala Glu Tyr Asp Phe Ser Lys Arg Thr Ser Ala Leu Val Ser
            290                 295                 300

Ala Gly Trp Leu Gln Glu Gly Lys Gly Glu Asn Lys Phe Val Ser Thr
305                 310                 315                 320

Ala Gly Gly Val Gly Leu Arg His Lys Phe
                325                 330

<210> SEQ ID NO 47
<211> LENGTH: 331
<212> TYPE: PRT
<213> ORGANISM: Artificial Sequence
<220> FEATURE:
<223> OTHER INFORMATION: Chimeric PorB Protein

<400> SEQUENCE: 47

Met Lys Lys Ser Leu Ile Ala Leu Thr Leu Ala Ala Leu Pro Val Ala
1               5                   10                  15

Ala Met Ala Asp Val Thr Leu Tyr Gly Thr Ile Lys Ala Gly Val Glu
            20                  25                  30

Thr Ser Arg Ser Val Phe His Gln Asn Gly Gln Val Thr Glu Val Thr
        35                  40                  45

Thr Ala Thr Gly Ile Val Asp Leu Gly Ser Lys Ile Gly Phe Lys Gly
    50                  55                  60

Gln Glu Asp Leu Gly Asn Gly Leu Lys Ala Ile Trp Gln Val Glu Gln
65                  70                  75                  80

Lys Ala Ser Ile Ala Gly Thr Asp Ser Gly Trp Gly Asn Arg Gln Ser
                85                  90                  95

Phe Ile Gly Leu Lys Gly Gly Phe Gly Lys Leu Arg Val Gly Arg Leu
            100                 105                 110

Asn Ser Val Leu Lys Asp Thr Gly Asp Ile Asn Pro Trp Asp Ser Lys
        115                 120                 125

Ser Asp Tyr Leu Gly Val Asn Lys Ile Ala Glu Pro Glu Ala Arg Leu
    130                 135                 140

Ile Ser Val Arg Tyr Asp Ser Pro Glu Phe Ala Gly Leu Ser Gly Ser
145                 150                 155                 160

Val Gln Tyr Ala Leu Asn Asp Asn Ala Gly Arg His Asn Ser Glu Ser
                165                 170                 175

Tyr His Ala Gly Phe Asn Tyr Lys Asn Gly Gly Phe Phe Val Gln Tyr
            180                 185                 190

Gly Gly Ala Tyr Lys Arg His His Gln Val Gln Glu Gly Leu Asn Ile
        195                 200                 205

Glu Lys Tyr Gln Ile His Arg Leu Val Ser Gly Tyr Asp Asn Asp Ala
    210                 215                 220

Leu Tyr Ala Ser Val Ala Val Gln Gln Gln Asp Ala Lys Leu Thr Asp
225                 230                 235                 240

Ala Ser Asn Ser His Asn Ser Gln Thr Glu Val Ala Ala Thr Leu Ala
                245                 250                 255

Tyr Arg Phe Gly Asn Val Thr Pro Arg Val Ser Tyr Ala His Gly Phe
            260                 265                 270

Lys Gly Ser Phe Asp Asp Ala Asp Leu Ser Asn Asp Tyr Asp Gln Val
        275                 280                 285

Val Val Gly Ala Glu Tyr Asp Phe Ser Lys Arg Thr Ser Ala Leu Val
    290                 295                 300

Ser Ala Gly Trp Leu Gln Glu Gly Lys Gly Glu Asn Lys Phe Val Ser
305                 310                 315                 320

```
Thr Ala Gly Gly Val Gly Leu Arg His Lys Phe
            325                 330

<210> SEQ ID NO 48
<211> LENGTH: 330
<212> TYPE: PRT
<213> ORGANISM: Artificial Sequence
<220> FEATURE:
<223> OTHER INFORMATION: Chimeric PorB Protein

<400> SEQUENCE: 48

Met Lys Lys Ser Leu Ile Ala Leu Thr Leu Ala Ala Leu Pro Val Ala
1               5                   10                  15

Ala Met Ala Asp Val Thr Leu Tyr Gly Thr Ile Lys Ala Gly Val Glu
            20                  25                  30

Thr Ser Arg Ser Val Phe His Gln Asn Gly Gln Val Thr Glu Val Thr
        35                  40                  45

Thr Ala Thr Gly Ile Val Asp Leu Gly Ser Lys Ile Gly Phe Lys Gly
    50                  55                  60

Gln Glu Asp Leu Gly Asn Gly Leu Lys Ala Ile Trp Gln Val Glu Gln
65                  70                  75                  80

Lys Ala Ser Ile Ala Gly Thr Asp Ser Gly Trp Gly Asn Arg Gln Ser
                85                  90                  95

Phe Ile Gly Leu Lys Gly Phe Gly Lys Leu Arg Val Gly Arg Leu
            100                 105                 110

Asn Ser Val Leu Lys Asp Thr Gly Asp Ile Asn Pro Trp Asp Ser Lys
        115                 120                 125

Ser Asp Tyr Leu Gly Val Asn Lys Ile Ala Glu Pro Glu Ala Arg Leu
    130                 135                 140

Ile Ser Val Arg Tyr Asp Ser Pro Glu Phe Ala Gly Leu Ser Gly Ser
145                 150                 155                 160

Val Gln Tyr Ala Leu Asn Asp Asn Ala Gly Arg His Asn Ser Glu Ser
                165                 170                 175

Tyr His Ala Gly Phe Asn Tyr Lys Asn Gly Gly Phe Phe Val Gln Tyr
            180                 185                 190

Gly Gly Ala Tyr Lys Arg His Gln Asp Val Asp Val Lys Ile Glu
        195                 200                 205

Lys Tyr Gln Ile His Arg Leu Val Ser Gly Tyr Asp Asn Asp Ala Leu
    210                 215                 220

His Ala Ser Val Ala Val Gln Gln Asp Ala Lys Leu Val Glu Asp
225                 230                 235                 240

Asn Tyr Ser His Asn Ser Gln Thr Glu Val Ala Ala Thr Leu Ala Tyr
                245                 250                 255

Arg Phe Gly Asn Val Thr Pro Arg Val Ser Tyr Ala His Gly Phe Lys
            260                 265                 270

Gly Leu Val Asp Asp Ala Asp Ile Gly Asn Glu Tyr Asp Gln Val Val
        275                 280                 285

Val Gly Ala Glu Tyr Asp Phe Ser Lys Arg Thr Ser Ala Leu Val Ser
    290                 295                 300

Ala Gly Trp Leu Gln Glu Gly Lys Gly Glu Asn Lys Phe Val Ala Thr
305                 310                 315                 320

Ala Gly Gly Val Gly Leu Arg His Lys Phe
            325                 330

<210> SEQ ID NO 49
```

```
<211> LENGTH: 331
<212> TYPE: PRT
<213> ORGANISM: Artificial Sequence
<220> FEATURE:
<223> OTHER INFORMATION: Chimeric PorB Protein

<400> SEQUENCE: 49

Met Lys Lys Ser Leu Ile Ala Leu Thr Leu Ala Ala Leu Pro Val Ala
1               5                   10                  15

Ala Met Ala Asp Val Thr Leu Tyr Gly Thr Ile Lys Ala Gly Val Glu
            20                  25                  30

Thr Ser Arg Ser Val Glu His Asn Gly Gly Gln Val Val Ser Val Glu
        35                  40                  45

Thr Gly Thr Gly Ile Val Asp Leu Gly Ser Lys Ile Gly Phe Lys Gly
    50                  55                  60

Gln Glu Asp Leu Gly Asn Gly Leu Lys Ala Ile Trp Gln Val Glu Gln
65                  70                  75                  80

Lys Ala Ser Ile Ala Gly Thr Asp Ser Gly Trp Gly Asn Arg Gln Ser
                85                  90                  95

Phe Ile Gly Leu Lys Gly Gly Phe Gly Lys Leu Arg Val Gly Arg Leu
            100                 105                 110

Asn Ser Val Leu Lys Asp Thr Gly Asp Ile Asn Pro Trp Asp Ser Lys
        115                 120                 125

Ser Asp Tyr Leu Gly Val Asn Lys Ile Ala Glu Pro Glu Ala Arg Leu
    130                 135                 140

Ile Ser Val Arg Tyr Asp Ser Pro Glu Phe Ala Gly Leu Ser Gly Ser
145                 150                 155                 160

Val Gln Tyr Ala Leu Asn Asp Asn Ala Gly Arg His Asn Ser Glu Ser
                165                 170                 175

Tyr His Ala Gly Phe Asn Tyr Lys Asn Gly Gly Phe Phe Val Gln Tyr
            180                 185                 190

Gly Gly Ala Tyr Lys Arg His His Gln Val Gln Glu Gly Leu Asn Ile
        195                 200                 205

Glu Lys Tyr Gln Ile His Arg Leu Val Ser Gly Tyr Asp Asn Asp Ala
    210                 215                 220

Leu Tyr Ala Ser Val Ala Val Gln Gln Gln Asp Ala Lys Leu Thr Asp
225                 230                 235                 240

Ala Ser Asn Ser His Asn Ser Gln Thr Glu Val Ala Ala Thr Leu Ala
                245                 250                 255

Tyr Arg Phe Gly Asn Val Thr Pro Arg Val Ser Tyr Ala His Gly Phe
            260                 265                 270

Lys Gly Leu Val Asp Asp Ala Asp Ile Gly Asn Glu Tyr Asp Gln Val
        275                 280                 285

Val Val Gly Ala Glu Tyr Asp Phe Ser Lys Arg Thr Ser Ala Leu Val
    290                 295                 300

Ser Ala Gly Trp Leu Gln Glu Gly Lys Gly Glu Asn Lys Phe Val Ala
305                 310                 315                 320

Thr Ala Gly Gly Val Gly Leu Arg His Lys Phe
                325                 330

<210> SEQ ID NO 50
<211> LENGTH: 330
<212> TYPE: PRT
<213> ORGANISM: Artificial Sequence
<220> FEATURE:
<223> OTHER INFORMATION: Chimeric PorB Protein
```

```
<400> SEQUENCE: 50

Met Lys Lys Ser Leu Ile Ala Leu Thr Leu Ala Ala Leu Pro Val Ala
1               5                   10                  15

Ala Met Ala Asp Val Thr Leu Tyr Gly Thr Ile Lys Ala Gly Val Glu
            20                  25                  30

Thr Ser Arg Ser Val Glu His Asn Gly Gly Gln Val Val Ser Val Glu
        35                  40                  45

Thr Gly Thr Gly Ile Val Asp Leu Gly Ser Lys Ile Gly Phe Lys Gly
    50                  55                  60

Gln Glu Asp Leu Gly Asn Gly Leu Lys Ala Ile Trp Gln Val Glu Gln
65                  70                  75                  80

Lys Ala Ser Ile Ala Gly Thr Asp Ser Gly Trp Gly Asn Arg Gln Ser
                85                  90                  95

Phe Ile Gly Leu Lys Gly Gly Phe Gly Lys Leu Arg Val Gly Arg Leu
            100                 105                 110

Asn Ser Val Leu Lys Asp Thr Gly Asp Ile Asn Pro Trp Asp Ser Lys
        115                 120                 125

Ser Asp Tyr Leu Gly Val Asn Lys Ile Ala Glu Pro Glu Ala Arg Leu
    130                 135                 140

Ile Ser Val Arg Tyr Asp Ser Pro Glu Phe Ala Gly Leu Ser Gly Ser
145                 150                 155                 160

Val Gln Tyr Ala Leu Asn Asp Asn Ala Gly Arg His Asn Ser Glu Ser
                165                 170                 175

Tyr His Ala Gly Phe Asn Tyr Lys Asn Gly Gly Phe Phe Val Gln Tyr
            180                 185                 190

Gly Gly Ala Tyr Lys Arg His Gln Asp Val Asp Val Lys Ile Glu
        195                 200                 205

Lys Tyr Gln Ile His Arg Leu Val Ser Gly Tyr Asp Asn Asp Ala Leu
    210                 215                 220

His Ala Ser Val Ala Val Gln Gln Gln Asp Ala Lys Leu Val Glu Asp
225                 230                 235                 240

Asn Tyr Ser His Asn Ser Gln Thr Glu Val Ala Ala Thr Leu Ala Tyr
                245                 250                 255

Arg Phe Gly Asn Val Thr Pro Arg Val Ser Tyr Ala His Gly Phe Lys
            260                 265                 270

Gly Leu Val Asp Asp Ala Asp Ile Gly Asn Glu Tyr Asp Gln Val Val
        275                 280                 285

Val Gly Ala Glu Tyr Asp Phe Ser Lys Arg Thr Ser Ala Leu Val Ser
    290                 295                 300

Ala Gly Trp Leu Gln Glu Gly Lys Gly Glu Asn Lys Phe Val Ala Thr
305                 310                 315                 320

Ala Gly Gly Val Gly Leu Arg His Lys Phe
                325                 330

<210> SEQ ID NO 51
<211> LENGTH: 331
<212> TYPE: PRT
<213> ORGANISM: Artificial Sequence
<220> FEATURE:
<223> OTHER INFORMATION: Chimeric PorB Protein

<400> SEQUENCE: 51

Met Lys Lys Ser Leu Ile Ala Leu Thr Leu Ala Ala Leu Pro Val Ala
1               5                   10                  15

Ala Met Ala Asp Val Thr Leu Tyr Gly Thr Ile Lys Ala Gly Val Glu
```

```
                        20                      25                      30
Thr Ser Arg Ser Val Glu His Asn Gly Gly Gln Val Val Ser Val Glu
            35                      40                      45
Thr Gly Thr Gly Ile Val Asp Leu Gly Ser Lys Ile Gly Phe Lys Gly
            50                      55                      60
Gln Glu Asp Leu Gly Asn Gly Leu Lys Ala Ile Trp Gln Val Glu Gln
 65                      70                      75                      80
Lys Ala Ser Ile Ala Gly Thr Asp Ser Gly Trp Gly Asn Arg Gln Ser
                    85                      90                      95
Phe Ile Gly Leu Lys Gly Gly Phe Gly Lys Leu Arg Val Gly Arg Leu
                    100                     105                     110
Asn Ser Val Leu Lys Asp Thr Gly Asp Ile Asn Pro Trp Asp Ser Lys
                115                     120                     125
Ser Asp Tyr Leu Gly Val Asn Lys Ile Ala Glu Pro Glu Ala Arg Leu
            130                     135                     140
Ile Ser Val Arg Tyr Asp Ser Pro Glu Phe Ala Gly Leu Ser Gly Ser
145                     150                     155                     160
Val Gln Tyr Ala Leu Asn Asp Asn Ala Gly Arg His Asn Ser Glu Ser
                165                     170                     175
Tyr His Ala Gly Phe Asn Tyr Lys Asn Gly Gly Phe Phe Val Gln Tyr
                180                     185                     190
Gly Gly Ala Tyr Lys Arg His His Gln Val Gln Glu Gly Leu Asn Ile
                195                     200                     205
Glu Lys Tyr Gln Ile His Arg Leu Val Ser Gly Tyr Asp Asn Asp Ala
            210                     215                     220
Leu Tyr Ala Ser Val Ala Val Gln Gln Gln Asp Ala Lys Leu Thr Asp
225                     230                     235                     240
Ala Ser Asn Ser His Asn Ser Gln Thr Glu Val Ala Ala Thr Leu Ala
                245                     250                     255
Tyr Arg Phe Gly Asn Val Thr Pro Arg Val Ser Tyr Ala His Gly Phe
                260                     265                     270
Lys Gly Ser Phe Asp Asp Ala Asp Leu Ser Asn Asp Tyr Asp Gln Val
            275                     280                     285
Val Val Gly Ala Glu Tyr Asp Phe Ser Lys Arg Thr Ser Ala Leu Val
            290                     295                     300
Ser Ala Gly Trp Leu Gln Glu Gly Lys Gly Glu Asn Lys Phe Val Ser
305                     310                     315                     320
Thr Ala Gly Gly Val Gly Leu Arg His Lys Phe
                325                     330
```